US008425919B2

(12) United States Patent
Goto et al.

(10) Patent No.: US 8,425,919 B2
(45) Date of Patent: Apr. 23, 2013

(54) RECOMBINANT POLYPROTEIN VACCINES FOR THE TREATMENT AND DIAGNOSIS OF LEISHMANIASIS

(75) Inventors: Yasuyuki Goto, Seattle, WA (US); Steven G. Reed, Bellevue, WA (US)

(73) Assignee: Infectious Disease Research Institute, Seattle, WA (US)

( * ) Notice: Subject to any disclaimer, the term of this patent is extended or adjusted under 35 U.S.C. 154(b) by 0 days.

(21) Appl. No.: 12/466,580

(22) Filed: May 15, 2009

(65) Prior Publication Data
US 2009/0291099 A1 Nov. 26, 2009

Related U.S. Application Data

(60) Provisional application No. 61/055,079, filed on May 21, 2008.

(51) Int. Cl.
*A61K 39/008* (2006.01)
*C07H 21/04* (2006.01)

(52) U.S. Cl.
USPC .... 424/269.1; 536/23.4; 536/23.7; 424/192.1

(58) Field of Classification Search .................. None
See application file for complete search history.

(56) References Cited

U.S. PATENT DOCUMENTS

| 5,827,671 | A * | 10/1998 | Matlashewski et al. ..... 435/7.22 |
| 8,231,881 | B2 | 7/2012 | Bhatia et al. |
| 2003/0138451 | A1 | 7/2003 | Bedate et al. |
| 2004/0170636 | A1 | 9/2004 | Matlashewski |
| 2008/0131466 | A1 | 6/2008 | Reed et al. |
| 2008/0241193 | A1 | 10/2008 | Fischer |
| 2009/0041798 | A1 | 2/2009 | Reed et al. |
| 2010/0136046 | A1 | 6/2010 | Goto et al. |

FOREIGN PATENT DOCUMENTS

| WO | 0179276 A2 | 10/2001 |
| WO | 2005025614 A2 | 3/2005 |
| WO | 2005039633 A1 | 5/2005 |

OTHER PUBLICATIONS

Bowie et al (Science, 1990, 257:1306-1310).*
Greenspan et al. (Nature Biotechnology 7: 936-937, 1999).*
Afonso et al., "The Adjuvant Effect of Interleukin-12 in a Vaccine Against *Leishmania major*," Science 263: 235-237, Jan. 14, 1994.
Aguilar-Be et al., "Cross-Protective Efficacy of a Prophylactic *Leishmania donovani* DNA Vaccine against Visceral and Cutaneous Murine Leishmaniasis," Infection and Immunity 73(2): 812-819, Feb. 2005.
Basu et al., "Kinetoplastid Membrane Protein-11 DNA Vaccination Induces Complete Protection against Both Pentavalent Antimonial-Sensitive and -Resistant Strains of *Leishmania donovani* That Correlates with Inducible Nitric Oxide Synthase Activity and IL-4 Generation: Evidence for Mixed Th1- and Th2-Like Responses in Visceral Leishmaniasis," The Journal of Immunology 174: 7160-7171, 2005.
Coler et al., "Immunization with a Polyprotein Vaccine Consisting of the T-Cell Antigens Thiol-Specific Antioxidant, *Leishmania major* Stress-Inducible Protein 1, and Leishmania Elongation Initiation Factor Protects against Leishmaniasis," Infection and Immunity 70(8): 4215-4225, Aug. 2002.
Engwerda et al., "Neutralization of IL-12 demonstrates the existence of discrete organ-specific phases in the control of *Leishmania donovani*," European Journal of Immunology 28: 669-680, 1998.
Ghosh et al., "Immunization with A2 protein results in a mixed Th1/Th2 and a humoral response which protects mice against *Leishmania donovani* infections," Vaccine 20(1-2): 59-66, Oct. 12, 2001.
Gurunathan et al., "Vaccination with DNA Encoding the Immunodominant LACK Parasite Antigen Confers Protective Immunity to Mice Infected with *Leishmania major*," The Journal of Experimental Medicine 186(7): 1137-1147, Oct. 6, 1997.
Kaye et al., "Leishmania donovani Infection in scid Mice: Lack of Tissue Response and In Vivo Macrophage Activation Correlates with Failure to Trigger Natural Killer Cell-Derived Gamma Interferon Production In Vitro," Infection and Immunity 60(10): 4335-4342, Oct. 1992.
Kenney et al., "Protective Immunity Using Recombinant Human IL-12 and Alum as Adjuvants in a Primate Model of Cutaneous Leishmaniasis," The Journal of Immunology 163: 4481-4488, 1999.
Mendez et al., "The Potency and Durability of DNA- and Protein-Based Vaccines Against *Leishmania major* Evaluated Using Low-Dose, Intradermal Challenge, "The Journal of Immunology 166: 5122-5128, 2001.
Murphy et al., "IL-10 mediates susceptibility to *Leishmania donovani* infection," European Journal of Immunology 31: 2848-2856, 2001.
Murray et al., "Macrophage Microbicidal Mechanisms In Vivo: Reactive Nitrogen versus Oxygen Intermediates in the Killing of Intracellular Visceral *Leishmania donovani*," Journal of Experimental Medicine 189(4): 741-746, Feb. 15, 1999.
Murray et al., "Visceral Leishmaniasis in Mice Devoid of Tumor Necrosis Factor and Response to Treatment," Infection and Immunity 68(11): 6289-6293, Nov. 2000.
Piedrafita et al., "Protective Immune Responses Induced by Vaccination with an Expression Genomic Library of *Leishmania major*," The Journal of Immunology 163: 1467-1472, 1999.
Rafati et al., "Prime-boost vaccination using cysteine proteinases type I and II of *Leishmania infantum* confers protective immunity in murine visceral leishmaniasis," Vaccine 24: 2169-2175, 2006.
Rhee et al., "Vaccination with Heat-killed Leishmania Antigen or Recombinant Leishmanial Protein and CpG Oligodeoxynucleotides Induces Long-Term Memory CD4+ and CD8+ T Cell Responses and Protection Against *Leishmania major* Infection," The Journal of Experimental Medicine 195(12): 1565-1573, Jun. 17, 2002.
Skeiky et al., "Protective efficacy of a tandemly linked, multi-subunit recombinant leishmanial vaccine (Leish-111f) formulated in MPL® adjuvant," Vaccine 20: 3292-3303, 2002.

(Continued)

*Primary Examiner* — Padma V Baskar
(74) *Attorney, Agent, or Firm* — Judy Jarecki-Black; Chad Kitchen; Merial Limited

(57) ABSTRACT

Compositions and methods for preventing, treating and detecting leishmaniasis are disclosed. The compositions generally comprise fusion polypeptides comprising multiple *Leishmania* antigens, in particular, KMP11, SMT, A2 and/or CBP, or immunogenic portions or variants thereof, as well as polynucleotides encoding such fusion polypeptides.

12 Claims, 6 Drawing Sheets

OTHER PUBLICATIONS

Squires et al., "Experimental Visceral Leishmaniasis: Role of Endogenous IFN-γ in Host Defense and Tissue Granulomatous Response," The Journal of Immunology 143(12): 4244-4249, Dec. 15, 1989.

Stacey et al., "Immunostimulatory DNA as an Adjuvant in Vaccination against *Leishmania major*," Infection and Immunity 67(8): 3719-3726, Aug. 1999.

Stäger et al., "Immunization with a Recombinant Stage-Regulated Surface Protein from *Leishmania donovani* Induces Protection Against Visceral Leishmaniasis," The Journal of Immunology 165: 7064-7071, 2000.

Stern et al., "Role of L3T4+ and LYT-2+ Cells in Experimental Visceral Leishmaniasis," The Journal of Immunology 140(11): 3971-3977, Jun. 1, 1988.

Stobie et al., "The role of antigen and IL-12 in sustaining Th1 memory cells in vivo: IL-12 is required to maintain memory/effector TH1 cells sufficient to mediate protection to an infectious parasite challenge," Proceedings of the National Academy of Sciences 97(15): 8427-8432, Jul. 18, 2000.

Taylor et al., "Intracellular Antimicrobial Activity in the Absence of Interferon-γ: Effect of Interleukin-12 in Experimental Visceral Leishmaniasis in Interferon-γ Gene-disrupted Mice," Journal of Experimental Medicine 185(7): 1231-1239, Apr. 7, 1997.

Tewary et al., "A Heterologous Prime-Boost Vaccination Regimen Using ORFF DNA and Recombinant ORFF Protein Confers Protective Immunity against Experimental Visceral Leishmaniasis," The Journal of Infectious Diseases 191: 2130-2137, Jun. 15, 2005.

Walker et al., "Immunostimulatory oligodeoxynucleotides promote protective immunity and provide systemic therapy for leishmaniasis via IL-12- and IFN-γ-dependent mechanisms," Proceedings of the National Academy of Sciences USA 96: 6970-6975, Jun. 1999.

Wilson et al., "A Recombinant *Leishmania chagasi* Antigen That Stimulates Cellular Immune Responses in Infected Mice," Infection and Immunity 63(5): 2062-2069, May 1995.

Wilson et al., "The Importance of TGF-β in Murine Visceral Leishmaniasis," The Journal of Immunology 161: 6148-6155, 1998.

Aebischer et al., "Subunit Vaccination of Mice Against New World Cutaneous Leishmaniasis: Comparison of Three Proteins Expressed in Amastigotes and Six Adjuvants," Infection and Immunity 68(3): 1328-1336, Mar. 1, 2000.

Coler et al., "Second-generation vaccines against leishmaniasis," Trends in Parasitology 21(5): 244-249, May 1, 2005.

Goto et al., "Protective immunization against visceral leishmaniasis using Leishmania sterol 24-c-methyltransferase formulated in adjuvant," Vaccine 25(42): 7450-7458, Sep. 28, 2007.

Jensen et al., "Humoral and Cellular Immune Responses to Synthetic Peptides of the *Leishmania donovani* Kinetoplastid Membrane Protein-11," Scandinavian Journal of Immunology 48(1): 103-109, Jul. 1998.

Rafati et al., "Identification of *Leishmania major* cysteine proteinases as targets of the immune response in humans," Molecular and Biochemical Parasitology 113(1): 35-43, Mar. 2001.

U.S. Appl. No. 13/560,565, filed on Jul. 27, 2012 by Bhatia et al.

Zadeh-Vakili, A. et al. (2004). "Immunization with the Hybrid Protein Vaccine, Consisting of *Leishmania Major* Cysteine Proteinases Type I (CPB) and Type II (CPA), Partially Protects Against Leishmaniasis," *Vaccine* 22:1930-1940.

\* cited by examiner

*ATGGCCACCACGTACGAGGAGTTTTCGGCGAAGCTGGACCGCCTGGATGAG*
*GAGTTCAACAGGAAGATGCAGGAGCAGAACGCCAAGTTCTTTGCGGACAAG*
*CCGGATGAGTCGACGCTGTCGCCCGAGATGAAGGAGCACTACGAGAAGTTC*
*GAGCGCATGATCAAGGAACACACAGAGAAGTTCAACAAGAAGATGCACGAG*
*CACTCGGAGCACTTCAAGCAGAAGTTCGCCGAGCTGCTCGAGCAGCAGAAG*
*GCTGCGCAGTACCCGTCCAAG*(ACTAGT)<ins>TCCGCCGGTGGCCGTGAGACCGC
GCCGACGAACCTGATTCGTCGCCGCAACAAGGACGAGACAAACGGGGATGT
CAGCGCCGCCGCCGACCGCTTCCGCGACCGCTTCGAGAAGGCAACCCTCGA
GGAGCGCAAGGCCGCCACCACGACGATGGTCAACGAGTACTACGACCTGGT
GACGGACTTCTACGAGTACGGCTGGGGCCAGAACTTCCATTTCGCGCCGCG
CTACGCCGGCGAGACCTTCTTCGAGTCCCTCGCGCGCCACGAGTACTTCCT
GGCCGCTCGCGGCGGCTTCATGGAGGGCGACCACATCGTCGACGTGGGCT
GCGGCGTCGGCGGTCCGGCGCGCAACATGGTTCGCCTCACGCGCTGCAAC
GTCATCGGCGTCAACAACAACGATTACCAGATCAGCCGCGCTCGCCGTCATG
ACGCGCTCGCCGGTATGAGCTCCAAGATCGACTACGTCAAGACCGACTTCTG
CAACATGAGCTTAGCCGACAACACCTTCGACGGCGCCTACGCCATCGAGGC
CACCTGCCACGCAAAGGACAAGGTCAAGTGCTATAGCGAGGTCTTCCGTGTC
ATCAAGCCCGGCACCTGCTTTGTCCTGTACGAGTGGTGCATGACCGACAAGT
ACAACCCCAATGACGAGTACCACCGCACAATCAAGCACCGCATCGAGCTGG
GCGACGGCCTGCCGGAGATGGAGACGTGCAAACAGGTGATCGAGTACATGA
AGCAGGCCGGCTTCGTGGTGGAGGAGGCCATAGACGTCATCAGTCAGTTCG
AGTCCAGCCCCATCAAGAGTATCCCGTGGTACCAGCCGCTGGTCGGCGACT
ATTCGTCCTGCAGGGCCTGCGCTCTACCCCGATTGGCCGCATCCTCACGAA
CGTCATGTGTCGCGTGCTGGAGTTCGTGCGCCTAGCTCCGAAGGGCACGTA
CAAGGCGACGGAGATTTTGGAGGAGGCTGCGGAAAGCCTGGTGGTGGGCG
GTCAGCTCGGCATCTTCACGCCGTCCTTCTACATCCGCGCTCGCAAGCCGTC
CAAGCAGGCT</ins>(GGATCC)**GAGCCGCACAAGGCGGCCGTTGACGTCGGCCCG
CTCTCCGTTGGCCCGCAGTCCGTCGGCCCGCTCTCTGTTGGCCCGCAGGCT
GTTGGCCCGCTCTCCGTTGGCCCGCAGTCCGTCGGCCCGCTCTCTGTTGGC
CCGCAGGCTGTTGGCCCGCTCTCTGTTGGCCCGCAGTCCGTTGGCCCGCTC
TCCGTTGGCCCGCTCTCCGTTGGCCCGCAGTCTGTTGGCCCGCTCTCCGTT
GGCTCGCAGTCCGTCGGCCCGCTCTCTGTTGGTCCGCAGTCCGTCGGCCCG
CTCTCCGTTGGCCCGCAGGCTGTTGGCCCGCTCTCCGTTGGCCCGCAGTCC
GTCGGCCCGCTCTCTGTTGGCCCGCAGGCTGTTGGCCCGCTCTCTGTTGGC
CCGCAGTCCGTTGGCCCGCTCTCCGTTGGCCCGCAGTCTGTTGGCCCGCTC
TCCGTTGGCTCGCAGTCCGTCGGCCCGCTCTCTGTTGGTCCGCAGTCCGTC
GGCCCGCTCTCCGTTGGCCCGCAGTCTGTCGGCCCGCTCTCCGTTGGCCCG
CAGTCCGTCGGCCCGCTCTCCGTTGGTCCGCAGTCCGTTGGCCCGCTCTCC
GTTGGCCCGCAGTCCGTTGACGTTTCTCCGGTGTCT**(GGATCCGAATTC)TAA

Fig. 4

ATGGCCACCACGTACGAGGAGTTTTCGGCGAAGCTGGACCGCCTGGATG
AGGAGTTCAACAGGAAGATGCAGGAGCAGAACGCCAAGTTCTTTGCGGAC
AAGCCGGATGAGTCGACGCTGTCGCCCGAGATGAAGGAGCACTACGAGA
AGTTCGAGCGCATGATCAAGGAACACACAGAGAAGTTCAACAAGAAGATG
CACGAGCACTCGGAGCACTTCAAGCAGAAGTTCGCCGAGCTGCTCGAGCA
GCAGAAGGCTGCGCAGTACCCGTCCAAG(ACTAGT)<u>TCCGCCGGTGGCCG
TGAGACCGCGCCGACGAACCTGATTCGTCGCCGCAACAAGGACGAGACA
AACGGGGATGTCAGCGCCGCCGCCGACCGCTTCCGCGACCGCTTCGAGA
AGGCAACCCTCGAGGAGCGCAAGGCCGCCACCACGACGATGGTCAACGA
GTACTACGACCTGGTGACGGACTTCTACGAGTACGGCTGGGGCCAGAACT
TCCATTTCGCGCCGCGCTACGCCGGCGAGACCTTCTTCGAGTCCCTCGCG
CGCCACGAGTACTTCCTGGCCGCTCGCGGCGGCTTCATGGAGGGCGACC
ACATCGTCGACGTGGGCTGCGGCGTCGGCGGTCCGGCGCGCAACATGGT
TCGCCTCACGCGCTGCAACGTCATCGGCGTCAACAACAACGATTACCAGA
TCAGCCGCGCTCGCCGTCATGACGCGCTCGCCGGTATGAGCTCCAAGAT
CGACTACGTCAAGACCGACTTCTGCAACATGAGCTTAGCCGACAACACCTT
CGACGGCGCCTACGCCATCGAGGCCACCTGCCACGCAAAGGACAAGGTC
AAGTGCTATAGCGAGGTCTTCCGTGTCATCAAGCCCGGCACCTGCTTTGT
CCTGTACGAGTGGTGCATGACCGACAAGTACAACCCCAATGACGAGTACC
ACCGCACAATCAAGCACCGCATCGAGCTGGGCGACGGCCTGCCGGAGAT
GGAGACGTGCAAACAGGTGATCGAGTACATGAAGCAGGCCGGCTTCGTG
GTGGAGGAGGCCATAGACGTCATCAGTCAGTTCGAGTCCAGCCCCATCAA
GAGTATCCCGTGGTACCAGCCGCTGGTCGGCGACTATTCGTCCCTGCAGG
GCCTGCGCTCTACCCCGATTGGCCGCATCCTCACGAACGTCATGTGTCGC
GTGCTGGAGTTCGTGCGCCTAGCTCCGAAGGGCACGTACAAGGCGACGG
AGATTTTGGAGGAGGCTGCGGAAAGCCTGGTGGTGGGCGGTCAGCTCGG
CATCTTCACGCCGTCCTTCTACATCCGCGCTCGCAAGCCGTCCAAGCAGG
CT(GGATCC)</u>**GAGCCGCACAAGGCGGCCGTTGACGTCGGCCCGCTCTCCG
TTGGCCCGCAGTCCGTCGGCCCGCTCTCTGTTGGCCCGCAGGCTGTTGG
CCCGCTCTCCGTTGGCCCGCAGTCCGTCGGCCCGCTCTCTGTTGGCCCG
CAGGCTGTTGGCCCGCTCTCTGTTGGCCCGCAGTCCGTTGGCCCGCTCT
CCGTTGGCCCGCTCTCCGTTGGCCCGCAGTCTGTTGGCCCGCTCTCCGTT
GGCTCGCAGTCCGTCGGCCCGCTCTCTGTTGGTCCGCAGTCCGTCGGCC
CGCTCTCCGTTGGCCCGCAGGCTGTTGGCCCGCTCTCCGTTGGCCCGCA
GTCCGTCGGCCCGCTCTCTGTTGGCCCGCAGGCTGTTGGCCCGCTCTCT
GTTGGCCCGCAGTCCGTTGGCCCGCTCTCCGTTGGCCCGCAGTCTGTTG
GCCCGCTCTCCGTTGGCTCGCAGTCCGTCGGCCCGCTCTCTGTTGGTCC
GCAGTCCGTCGGCCCGCTCTCCGTTGGCCCGCAGTCTGTCGGCCCGCTC
TCCGTTGGCCCGCAGTCCGTCGGCCCGCTCTCCGTTGGTCCGCAGTCCG
TTGGCCCGCTCTCCGTTGGCCCGCAGTCCGTTGACGTTTCTCCGGTGTCT
(GGATCCGAATTC)GATGCGGTGGACTGGCGCGAGAAGGGCGCCGTGACG
CCGGTGAAGAATCAAGGCGCGTGCGGGTCGTGCTGGGCGTTCTCGGCGG

Fig. 5A

```
TCGGCAACATCGAGTCGCAGTGGGCCCGTGCCGGCCACGGCTTGGTGAG
CCTGTCGGAGCAGCAGCTGGTGAGCTGCGATGACAAAGACAATGGCTGC
AACGGCGGGCTGATGCTGCAGGCGTTCGAGTGGCTGCTGCGACACATGT
ACGGGATCGTGTTCACGGAGAAGAGCTACCCCTACACGTCCGGCAACGGT
GATGTGGCCGAGTGCTTGAACAGCAGTAAACTCGTTCCCGGCGCGCAAAT
CGACGGCTACGTGATGATCCCGAGCAACGAAACGGTTATGGCTGCGTGG
CTTGCGGAGAATGGCCCCATCGCGATTGCGGTCGACGCCAGCTCCTTCAT
GTCTTACCAGAGCGGCGTGCTGACCAGCTGCGCTGGCGATGCACTGAAC
CACGGCGTGCTGCTCGTCGGGTACAACAAGACCGGTGGGGTTCCGTACT
GGGTGATCAAGAACTCGTGGGGTGAGGACTGGGGCGAGAAGGGCTACGT
GCGCGTGGTCATGGGGCTGAACGCGTGCCTGCTCAGTGAATACCCCGTG
TCCGCGCATGTGCCGCGGAGTCTCACCCCTGGCCCGGGCACGGAGAGCG
AGGAGCGCGCCCCTAAACGGGTGACGGTGGAGCAGATGATGTGCACCGA
TATGTACTGCAGGGAGGGGTGCAAGAAGAGTCTTCTCACCGCGAACGTGT
GCTACAAGAACGGGGGAGGCGGCTCCTCTATGACGAAGTGCGGTCCGCA
GAAGGTGCTGATGTGCTCGTACTCGAACCCTCATTGCTTTGGTCCTGGGC
TGTGCCTCGAGACTCCTGATGGCAAGTGCGCGCCGTACTTCTTGGGCTCG
ATCATGAACACCTGCCAGTACACGTAA
```

*Fig. 5B*

*MATTYEEFSAKLDRLDEEFNRKMQEQNAKFFADKPDESTLSPEMKEHYEKFE
RMIKEHTEKFNKKMHEHSEHFKQKFAELLEQQKAAQYPSK*(TS)<u>SAGGRETAPT
NLIRRRNKDETNGDVSAAADRFRDRFEKATLEERKAATTTMVNEYYDLVTDFY
EYGWGQNFHFAPRYAGETFFESLARHEYFLAARGGFMEGDHIVDVGCGVGG
PARNMVRLTRCNVIGVNNNDYQISRARRHDALAGMSSKIDYVKTDFCNMSLAD
NTFDGAYAIEATCHAKDKVKCYSEVFRVIKPGTCFVLYEWCMTDKYNPNDEYH
RTIKHRIELGDGLPEMETCKQVIEYMKQAGFVVEEAIDVISQFESSPIKSIPWYQ
PLVGDYSSLQGLRSTPIGRILTNVMCRVLEFVRLAPKGTYKATEILEEAAESLVV
GGQLGIFTPSFYIRARKPSKQA</u>(GS)**EPHKAAVDVGPLSVGPQSVGPLSVGPQ
AVGPLSVGPQSVGPLSVGPQAVGPLSVGPQSVGPLSVGPLSVGPQSVGPLS
VGSQSVGPLSVGPQSVGPLSVGPQAVGPLSVGPQSVGPLSVGPQAVGPLSV
GPQSVGPLSVGPQSVGPLSVGSQSVGPLSVGPQSVGPLSVGPQSVGPLSVG
PQSVGPLSVGPQSVGPLSVGPQSVDVSPVS**(GSEF)

Fig. 6

*MATTYEEFSAKLDRLDEEFNRKMQEQNAKFFADKPDESTLSPEMKEHYEKFERMI
KEHTEKFNKKMHEHSEHFKQKFAELLEQQKAAQYPSK*(TS)<u>SAGGRETAPTNLIRR
RNKDETNGDVSAAADRFRDRFEKATLEERKAATTTMVNEYYDLVTDFYEYGWGQ
NFHFAPRYAGETFFESLARHEYFLAARGGFMEGDHIVDVGCGVGGPARNMVRLT
RCNVIGVNNNDYQISRARRHDALAGMSSKIDYVKTDFCNMSLADNTFDGAYAIEAT
CHAKDKVKCYSEVFRVIKPGTCFVLYEWCMTDKYNPNDEYHRTIKHRIELGDGLPE
METCKQVIEYMKQAGFVVEEAIDVISQFESSPIKSIPWYQPLVGDYSSLQGLRSTPI
GRILTNVMCRVLEFVRLAPKGTYKATEILEEAAESLVVGGQLGIFTPSFYIRARKPSK
QA</u>(GS)**EPHKAAVDVGPLSVGPQSVGPLSVGPQAVGPLSVGPQSVGPLSVGPQA
VGPLSVGPQSVGPLSVGPLSVGPQSVGPLSVGSQSVGPLSVGPQSVGPLSVGP
QAVGPLSVGPQSVGPLSVGPQAVGPLSVGPQSVGPLSVGPQSVGPLSVGSQSV
GPLSVGPQSVGPLSVGPQSVGPLSVGPQSVGPLSVGPQSVGPLSVGPQSVDVS
PVS**(GSEF)DAVDWREKGAVTPVKNQGACGSCWAFSAVGNIESQWARAGHGLVS
LSEQQLVSCDDKDNGCNGGLMLQAFEWLLRHMYGIVFTEKSYPYTSGNGDVAEC
LNSSKLVPGAQIDGYVMIPSNETVMAAWLAENGPIAIAVDASSFMSYQSGVLTSCA
GDALNHGVLLVGYNKTGGVPYWVIKNSWGEDWGEKGYVRVVMGLNACLLSEYP
VSAHVPRSLTPGPGTESEERAPKRVTVEQMMCTDMYCREGCKKSLLTANVCYKN
GGGGSSMTKCGPQKVLMCSYSNPHCFGPGLCLETPDGKCAPYFLGSIMNTCQYT

Fig. 7

RECOMBINANT POLYPROTEIN VACCINES FOR THE TREATMENT AND DIAGNOSIS OF LEISHMANIASIS

CROSS-REFERENCE TO RELATED APPLICATION

This application claims the benefit under 35 U.S.C. §119(e) of U.S. Provisional Patent Application No. 61/055,079, filed May 21, 2008, where this provisional application is incorporated herein by reference in its entirety.

STATEMENT OF GOVERNMENT INTEREST

This invention was made with government support under Grant No. AI-025038 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480239_407_SEQUENCE_LISTING.txt. The text file is 99 KB, was created on May 15, 2009 and is being submitted electronically via EFS-Web, concurrent with the filing of the specification.

BACKGROUND

1. Technical Field

The present invention relates generally to compositions and methods for preventing, treating and detecting leishmaniasis in patients. More particularly, the invention relates to compositions and methods comprising *Leishmania* fusion polypeptides, as well as polynucleotides encoding such fusion polypeptides.

2. Description of the Related Art

*Leishmania* organisms are obligate intracellular parasites that cause a large clinical spectrum of diseases named leishmaniasis. *Leishmania* organisms are intracellular protozoan parasites of the genus *Leishmania*. *Leishmania* organisms target host macrophages; thus causing a wide spectrum of clinical diseases in humans and domestic animals, primarily dogs. In some infections, the parasite may lie dormant for many years. In other cases, the host may develop one of a variety of forms of leishmaniasis. Leishmaniases are roughly classified into three types of diseases, cutaneous leishmaniasis (CL), mucosal leishmaniasis (ML) and visceral leishmaniasis (VL), according to the clinical manifestations.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis.

Visceral leishmaniasis (VL) has been reported in 88 countries, but roughly 90% of VL cases occur in Brazil, India, Sudan, Bangladesh, and Nepal (Mendez et al. *J Immunol* 2001; 166(8): pp. 5122-8). The annual incidence is estimated to be approximately 500,000 cases of VL, and the population at risk is 350 million (Engwerda et al. *Eur J Immunol* 1998; 28(2): pp. 669-80; Squires et al. *Immunol* 1989; 143(12): pp. 4244-9). Visceral leishmaniasis, generally caused by species of the *L. donovani* complex, i.e. *L. donovani* and *L. infantum* (*chagasi*). *L. donovani* is the causative agent of visceral leishmaniasis in Africa and Asia, *L. infantum/chagasi* in Mediterranean countries and in the New World (Piedrafita et al. *J Immunol* 1999; 163(3): pp. 1467-72). VL is a severe debilitating disease that evolves with visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia. Active VL is generally fatal unless properly treated.

*Leishmania* parasites are transmitted by the bite of sandflies and the infecting promastigotes differentiate into and replicate as amastigotes within macrophages in the mammalian host. In common with other intracellular pathogens, cellular immune responses are critical for protection against leishmaniasis. Th1 immune responses play an important role in mediating protection against *Leishmania*, including roles for $CD4^+$ and $CD8^+$ T cells, IFN-γ, IL-12, TNF-α and NO, whereas inhibitory effects have been reported for IL-10 and TGF-β (Engwerda et al. *Eur J Immunol* 1998; 28(2): pp. 669-80; Murphy et al. *Eur J. Immunol.* 2001; 31 (10): pp. 2848-56; Murray et al. *J Exp Med.* 1999; 189(4): pp. 741-6; Murray et al. *Infect Immun.* 2000; 68(11): pp. 6289-93; Squires et al. *J Immunol* 1989; 143(12): pp. 4244-9 6; Taylor and Murray. *J Exp Med.* 1997; 185(7): pp. 1231-9; Kaye and Bancroft. *Infect Immun.* 1992; 60(10): pp. 4335-42; Stern et al. *J. Immunol.* 1988; 140(11): pp. 3971-7; Wilson et al. *J. Immunol.* 1998; 161(11): pp. 6148-55).

Immunization against leishmaniasis in animal models can be effected by delivery of antigen-encoding DNA vectors (Gurunathan et al. *J Exp Med.* 1997; 186(7): pp. 1137-47; Piedrafita et al. *J. Immunol.* 1999; 163(3):1467-72; Mendez et al. *J. Immunol.* 2001; 166(8): pp. 5122-8) or by administration of proteins formulated with Th1-inducing adjuvants including IL-12 (Afonso et al. *Science.* 1994; 263(5144): pp. 235-7; Stobie et al. *Proc Natl Acad Sci USA.* 2000; 97(15): pp. 8427-32; Kenney et al. *J. Immunol.* 1999; 163(8): pp. 4481-8) or TLR ligands such as CpG oligonucleotides (Rhee et al. *J Exp Med.* 2002; 195(12): pp. 1565-73; Stacey and Blackwell. *Infect Immun.* 1999; 67(8): pp. 3719-26; Walker et al. *Proc Natl Acad Sci USA.* 1999; 96(12): pp. 6970-5) and monophosphoryl lipid A (Coler et al. *Infect Immun.* 2002; 70(8): pp. 4215-25; Skeiky et al. *Vaccine.* 2002; 20(2728): pp. 3292-303).

In spite of some evidence that sub-unit vaccines may be effective in certain models of VL (Basu et al. *J. Immunol.* 2005; 174(11): pp. 7160-71; Stager et al. *J. Immunol.* 2000; 165(12): pp. 7064-71; Ghosh et al. *Vaccine.* 2001; 20(12): pp. 59-66; Wilson et al. *Infect Immun.* 1995; 63(5): pp. 2062-9; Tewary et al. *J Infect Dis.* 2005; 191(12): pp. 2130-7; Aguilar-Be et al. *Infect Immun.* 2005; 73(2): pp. 812-9. Rafati et al. *Vaccine.* 2006; 24(12):2169-75), progress toward defining antigen candidates effective against VL in vivo has been lacking.

Strategies employing vaccines consisting of whole organisms for preventing or treating leishmaniasis have not been effective in humans. Accordingly, there remains a significant need for immunogenic compositions and vaccines that can effectively prevent and/or treat leishmaniasis in humans and other mammals (e.g., canines). The present invention fulfills these needs and offers other related advantages

BRIEF SUMMARY

Briefly stated, the present invention provides compositions and methods for preventing, treating and detecting leishmaniasis. In one aspect, fusion polypeptides of the invention are provided which comprise an immunogenic portion of at least two *Leishmania* antigens selected from the group consisting of KMP11, SMT, A2 and/or CPB, or sequences having at least 90% identity thereto. In a more particular embodiment, the *Leishmania* KMP11, SMT, A2 and/or CPB polypeptide, or immunogenic portion or variant thereof, comprises an amino acid sequence of a KMP11, SMT, A2 and/or CPB sequence from *L. donovani, L. infantum* or *L. major*, or a sequence having at least 90% identity thereto.

In a more specific embodiment, a fusion polypeptide of the invention comprises an amino acid sequence set forth in SEQ ID NO: 21 (e.g., KSA fusion polypeptide) or SEQ ID NO: 23 (e.g., KSAC fusion polypeptide) or SEQ ID NO: 33 (e.g., $KSA_{FL}C$, wherein a full length A2 sequence is used).

In another embodiment of the invention, a fusion polypeptide herein is modified by replacing one or more of the cysteine residues of the polypeptide with alternative residues, such as serine or alanine, or any other residue not capable of interchain or intrachain disulfide bond formation, to produce a cysteine-modified fusion polypeptide. In a more specific embodiment, the cysteine-modified fusion polypeptide comprises an amino acid sequence set forth in any one of SEQ ID NO: 33 (e.g. cysteine-modified KSAC fusion polypeptide) or SEQ ID NO: 35 (e.g. cysteine-modified KSA fusion polypeptide).

In other embodiments, compositions comprising fusion polypeptides in combination with immunostimulants are provided. In still other embodiments, compositions comprising polynucleotides encoding the fusion polypeptides are also provided. Such compositions of the invention are preferably capable of providing protection against leishmaniasis, such as that caused by *L. major, L. infantum*, or *L. donovani* infection, in an in vivo assay.

Also provided by the invention are recombinant expression and delivery vectors comprising polynucleotide sequences of the invention and host cells transformed or transfected with such expression vectors.

In other embodiments, the present invention provides methods for stimulating an immune response against leishmaniasis in a mammal comprising administering a composition as described herein.

In yet other embodiments, the present invention provides methods to induce protective immunity against leishmaniasis in a mammal comprising administering a composition as described herein.

In still other embodiments, the present invention contemplates methods for detecting *Leishmania* infection in a biological sample, e.g., sera, blood, saliva, etc., comprising contacting the biological sample with a fusion polypeptide of the invention and detecting in the biological sample the presence of antibodies that bind to the fusion polypeptide, thereby detecting *Leishmania* infection in a biological sample. In related embodiments, the fusion polypeptide may be optionally bound to a solid support.

Various embodiments of the present invention also provide kits for use in the detection of *Leishmania* infection in a biological sample comprising a fusion polypeptide or polynucleotide of the invention and a detection reagent.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIG. 4 shows the polynucleotide sequence encoding a KSA fusion polypeptide (SEQ ID NO: 22) comprising a polynucleotide sequence of an immunogenic portion of KMP11 represented by polynucleotides 1-276 of SEQ ID NO: 1 (italicized), which is fused to an immunogenic portion of SMT represented by polynucleotides 4-1059 of SEQ ID NO: 4 (underlined), which is further fused to an immunogenic portion of A2 represented by polynucleotides 79-708 of SEQ ID NO: 7 (bolded). Linker polynucleotide sequences are in plaintext and delimited by parentheses. The terminal TAA stop codon is also plaintext.

FIGS. 5A-5B show the polynucleotide sequence encoding a KSAC fusion polypeptide (SEQ ID NO: 24) comprising a polynucleotide sequence of an immunogenic portion of KMP11 represented by polynucleotides 1-276 of SEQ ID NO: 1 (italicized), which is fused to an immunogenic portion of SMT represented by polynucleotides 4-1059 of SEQ ID NO: 4 (underlined), which is further fused to an immunogenic portion of A2 represented by polynucleotides 79-708 of SEQ ID NO: 7 (bolded), which is further fused to an immunogenic portion of CBP represented by polynucleotides 382-1329 of SEQ ID NO: 8 (plaintext). Linker polynucleotide sequences are in plaintext and delimited by parentheses. The terminal TAA stop codon is also plaintext.

FIG. 6 shows the amino acid sequence of a KSA fusion polypeptide (SEQ ID NO: 21) comprising an amino acid sequence of an immunogenic portion of KMP11 represented by amino acids 1-92 of SEQ ID NO: 11 (italicized), which is fused to an immunogenic portion of SMT represented by amino acids 2-353 of SEQ ID NO: 14 (underlined), which is further fused to an immunogenic portion of A2 represented by amino acids 29-236 of SEQ ID NO: 17 (bolded). Linker amino acids are in plaintext and delimited by parentheses.

FIG. 7 shows the polynucleotide sequence encoding a KSAC fusion polypeptide (SEQ ID NO: 23) comprising the amino acid sequence of an immunogenic portion of KMP11 represented by amino acids 1-92 of SEQ ID NO: 11 (italicized), which is fused to an immunogenic portion of SMT represented by amino acids 2-353 of SEQ ID NO: 14 (underlined), which is further fused to an immunogenic portion of A2 represented by amino acids 29-236 of SEQ ID NO: 17 (bolded), which is further fused to an immunogenic portion of CBP represented by amino acids 127-443 of SEQ ID NO: 18 (plaintext). Linker amino acids are in plaintext and delimited by parentheses.

BRIEF DESCRIPTION OF THE SEQUENCE IDENTIFIERS

Figure 1:
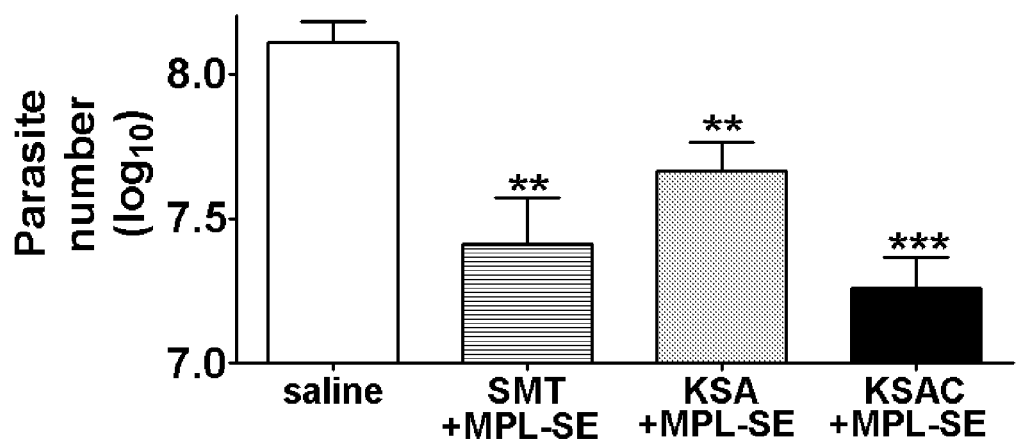
FIG. 1 shows protection against *L. infantum* infection by immunization with KSA or KSAC fusion polypeptides. C57BL/6 mice inoculated with saline alone, SMT+MPL-SE, KSA+MPL-SE or KSAC+MPL-SE were challenged with *L. infantum*, and the numbers of parasites in the liver were measured by limiting dilution four weeks after the infection. Mean and SEM of five mice in each group are shown. P<0.01 and *P<0.001 by unpaired t-test compared with the saline group.

SEQ ID NO: 1 is an amino acid sequence for a *L. infantum* full-length KMP11 polypeptide.

SEQ ID NO: 2 is an amino acid sequence for a *L. donovani* full-length KMP11 polypeptide.

SEQ ID NO: 3 is an amino acid sequence for a *L. major* full-length KMP11 polypeptide.

SEQ ID NO: 4 is an amino acid sequence for a *L. infantum* full-length sterol 24-c-methyltransferase (SMT) polypeptide.

SEQ ID NO: 5 is an amino acid sequence for a *L. donovani* full-length sterol 24-c-methyltransferase (SMT) polypeptide.

SEQ ID NO: 6 is an amino acid sequence for a *L. major* full-length sterol 24-c-methyltransferase (SMT) polypeptide.

SEQ ID NO: 7 is an amino acid sequence for a *L. infantum* full-length A2 polypeptide.

SEQ ID NO: 8 is an amino acid sequence for a *L. infantum* full-length CBP polypeptide.

SEQ ID NO: 9 is an amino acid sequence for a *L. donovani* full-length CBP polypeptide.

SEQ ID NO: 10 is an amino acid sequence for a *L. major* full-length CBP polypeptide.

SEQ ID NO: 11 is a nucleic acid sequence encoding the polypeptide of SEQ ID NO: 1.

SEQ ID NO: 12 is a nucleic acid sequence encoding the polypeptide of SEQ ID NO: 2.

SEQ ID NO: 13 is a nucleic acid sequence encoding the polypeptide of SEQ ID NO: 3.

SEQ ID NO: 14 is a nucleic acid sequence encoding the polypeptide of SEQ ID NO: 4.

SEQ ID NO: 15 is a nucleic acid sequence encoding the polypeptide of SEQ ID NO: 5.

SEQ ID NO: 16 is a nucleic acid sequence encoding the polypeptide of SEQ ID NO: 6.

SEQ ID NO: 17 is a nucleic acid sequence encoding the polypeptide of SEQ ID NO: 7.

SEQ ID NO: 18 is a nucleic acid sequence encoding the polypeptide of SEQ ID NO: 8.

SEQ ID NO: 19 is a nucleic acid sequence encoding the polypeptide of SEQ ID NO:9.

SEQ ID NO: 20 is a nucleic acid sequence encoding the polypeptide of SEQ ID NO: 10.

SEQ ID NO: 21 is an amino acid sequence for a KSA fusion polypeptide (KMP11, SMT, A2).

SEQ ID NO: 22 is a nucleic acid sequence encoding the polypeptide of SEQ ID NO: 21.

SEQ ID NO: 23 is an amino acid sequence for a KSAC fusion polypeptide (KMP11, SMT, A2, CPB).

SEQ ID NO: 24 is a nucleic acid sequence encoding the polypeptide of SEQ ID NO: 23.

SEQ ID NO: 25 is the amino acid sequence for an immunogenic portion of a KMP11 polypeptide.

SEQ ID NO: 26 is the amino acid sequence for an immunogenic portion of a SMP polypeptide.

SEQ ID NO: 27 is the amino acid sequence for an immunogenic portion of an A2 polypeptide.

SEQ ID NO: 28 is the amino acid sequence for an immunogenic portion of a CBP polypeptide.

SEQ ID NO: 29 is a nucleic acid sequence encoding the polypeptide of SEQ ID NO: 25.

SEQ ID NO: 30 is a nucleic acid sequence encoding the polypeptide of SEQ ID NO: 26.

SEQ ID NO: 31 is a nucleic acid sequence encoding the polypeptide of SEQ ID NO: 27.

SEQ ID NO: 32 is a nucleic acid sequence encoding the polypeptide of SEQ ID NO: 28.

SEQ ID NO: 33 is an amino acid sequence for an alternative version of a KSAC fusion polypeptide (KMP11, SMT, A2, CPB), wherein the full length A2 sequence is used.

SEQ ID NO: 34 is a nucleic acid sequence encoding the polypeptide of SEQ ID NO: 33.

SEQ ID NO: 35 is an amino acid sequence for an alternative version of a KSA fusion polypeptide (KMP11, SMT, A2), wherein the cysteine residues present in the fusion polypeptide have been replaced with serines or alanines.

SEQ ID NO: 36 is a nucleic acid sequence encoding the polypeptide of SEQ ID NO: 35.

SEQ ID NO: 37 is an amino acid sequence for an alternative version of a KSAC fusion polypeptide (KMP11, SMT, A2, CPB), wherein the cysteine residues present in the fusion polypeptide have been replaced with serines or alanines.

SEQ ID NO: 38 is a nucleic acid sequence encoding the polypeptide of SEQ ID NO: 37.

DETAILED DESCRIPTION

As noted above, the present invention is generally directed to compositions and methods for preventing, treating and detecting leishmaniasis. The compositions of the invention include, for example, fusion polypeptides and polypeptide combinations that comprise at least two immunogenic/antigenic portions or fragments of *Leishmania* KMP11, SMT, A2 and/or CPB polypeptides, or a variant of such a polypeptide, wherein the portion or variant retain substantially the same or similar immunogenic properties as a corresponding full length polypeptide. As further demonstrated herein, immunization strategies using compositions of the invention provide significant in vivo protection against *L. infantum, L. donovani*, and *L. major*, which are causative agents of VL in humans and dogs. Further, the prophylactic effect achieved using compositions of the present invention shows substantial improvements and advantages relative to previously reported vaccine strategies. The present invention also contemplates, in other embodiments, using the fusion polypeptides described herein in diagnostic applications, including, but not limited to, serodiagnosis and whole blood assay in patients and dogs.

As used herein, the term "polypeptide" encompasses amino acid chains of any length, including full length proteins, wherein the amino acid residues are linked by covalent bonds. A polypeptide comprising an immunogenic portion of a *Leishmania* polypeptide may consist solely of an immunogenic portion, may contain two or more immunogenic portions and/or may contain additional sequences. The additional sequences may be derived from a native *Leishmania* polypeptide or may be heterologous, and such heterologous sequences may (but need not) be immunogenic.

In various embodiments, compositions and methods of the present invention provide a fusion polypeptide comprising two or more immunogenic/antigenic portions or fragments of *Leishmania* KMP11, SMT, A2 and/or CPB polypeptides, or a variant thereof. In particular embodiments, a fusion polypeptide comprises two or more *Leishmania* antigen fragments as recited in SEQ ID NOs: 1-10 and 25-28. In related embodiments, the fusion polypeptide comprises the amino acid sequence set forth in any one of SEQ ID NOs: 21 or 35 (e.g., KSA) or in SEQ ID NOs: 23 or 33 or 37 (e.g., KSAC).

In other embodiments, the fusion polypeptides and polypeptide combinations are modified to replace the cysteine residues contained therein with serine residues, wherein the cysteine-modified polypeptides retain substantially the same or similar immunogenic properties as the corresponding unmodified polypeptides. For example, a cysteine-modified fusion polypeptide, in certain specific embodiments, comprises an amino acid sequence set forth in SEQ ID NOs: 35 (KSA) or 37 (KSAC)

Leishmania Fusion Polypeptides and Uses Therefor

In one aspect, the present invention provides isolated Leishmania polypeptides, as described herein, including fusion polypeptides, and compositions containing the same. Generally, a polypeptide of the present invention will be an isolated polypeptide and may comprise a polypeptide fragment (e.g., an antigenic/immunogenic portion), multiple polypeptide fragments, or a full-length polypeptide of an amino acid sequence from two or more of the Leishmania genes, including, but not limited to KMP11, SMT, A2 and/or CPB. An "isolated polypeptide" is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. One of ordinary skill in the art would appreciate that antigenic polypeptide fragments could also be obtained from those already available in the art. Polypeptides of the invention, antigenic/immunogenic fragments thereof, and other variants may be prepared using conventional recombinant and/or synthetic techniques.

An immunogenic portion of a Leishmania KMP11, SMT, A2 and/or CPB polypeptide is a portion that is capable of eliciting an immune response (i.e., cellular and/or humoral) in a presently or previously Leishmania-infected patient (such as a human or a dog) and/or in cultures of lymph node cells or peripheral blood mononuclear cells (PBMC) isolated from presently or previously Leishmania-infected individuals. The cells in which a response is elicited may comprise a mixture of cell types or may contain isolated component cells (including, but not limited to, T-cells, NK cells, macrophages, monocytes and/or B cells). In a particular embodiment, immunogenic portions of a fusion polypeptide comprising at least two Leishmania antigenic polypeptides selected from KMP11, SMT, A2, and/or CBP, are capable of inducing T-cell proliferation and/or a predominantly Th1-type cytokine response (e.g., IL-2, IFN-γ, and/or TNF-α production by T-cells and/or NK cells, and/or IL-12 production by monocytes, macrophages and/or B cells). Immunogenic portions of the antigens described herein may generally be identified using techniques known to those of ordinary skill in the art, including the representative methods summarized in Paul, *Fundamental Immunology,* 5th ed., Lippincott Williams & Wilkins, 2003 and references cited therein. Such techniques include screening fusion polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein and using well-known techniques.

Immunogenic portions of a Leishmania KMP11, SMT, A2 and/or CPB polypeptide can be essentially any length; provided they retain one or more of the immunogenic regions of KMP11, SMT, A2 and/or CPB that are responsible for and/or contribute to the in vivo protection provided against leishmaniasis by one or more fusion polypeptides of the invention, as disclosed herein. In one embodiment, the ability of an immunogenic portion to react with antigen-specific antisera may be enhanced or unchanged, relative to the native protein, or may be diminished by less than 50%, and preferably less than 20%, relative to the native protein. Illustrative portions will generally be at least 10, 15, 25, 50, 150, 200, 250, 300, or 350 amino acids in length, or more, up to and including full length KMP11, SMT, A2 and/or CPB polypeptide. In a particular embodiment, an immunogenic portion of a Leishmania KMP11, SMT, A2 and/or CPB polypeptide is one, which when used in combination, are capable of providing protection against, for example in an in vivo assay as described herein, or serodiagnosis of Leishmania species such as L. donovani, L. major and/or L. infantum, which are believed to be causative agents of VL in humans and dogs. In addition, compositions of the invention may also be useful in blocking transmission of the causative agent of VL from dogs to humans, e.g., by reducing or eliminating the number of parasites in the blood and skin of infected dogs.

As would be recognized by the skilled artisan, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof. In particular embodiments, the polypeptide is a fusion polypeptide as described herein.

In various embodiments of the present invention, fusion polypeptides of the present invention may comprise at least 2 antigenic or immunogenic portions or fragments of the Leishmania KMP11, SMT, A2 and/or CPB polypeptides, or a variant disclosed herein. In some instances, preferred immunogenic portions will be identified that have a level of immunogenic activity greater than that of the corresponding full-length polypeptide, e.g., having greater than about 100% or 150% or more immunogenic activity. In particular embodiments, the immunogenicity of the full-length fusion polypeptide will have additive, or greater than additive immunogenicity contributed by of each of the antigenic/immunogenic portions contained therein.

In another embodiment of the invention, fusion polypeptides are provided that comprise two or more immunogenic portions of Leishmania polypeptides selected from KMP11, SMT, A2, and/or CBP that are capable of eliciting T cells and/or antibodies that are immunologically reactive with two or more polypeptides described herein, or two or more polypeptides encoded by contiguous polynucleotide sequences contained in the polynucleotide sequences disclosed herein, or immunogenic fragments or variants thereof, or to two or more polynucleotide sequences which hybridize to two or more of these sequences under conditions of moderate to high stringency.

In particular embodiments, a fusion polypeptide of the present invention may comprise at least 2, at least 3 at least 4, at least 5, at least 6, at least 7, at least 8, at least 9, or at least 10 immunogenic/antigenic portions or fragments of Leishmania KMP11, SMT, A2 and/or CPB polypeptides, or a variant of such polypeptides, wherein the portions or fragments retain substantially the same or similar immunogenic properties as a corresponding full length polypeptide.

In another aspect, fusion polypeptides of the present invention contain multiple copies of polypeptide fragments, repeats of polypeptide fragments, or multimeric polypeptide fragments, including antigenic/immunogenic fragments such as Leishmania KMP11, SMT, A2 and/or CPB polypeptides, comprising at least about 1, 2, 3, 4, 5, 6, 7, 8, 9, 10 or more contiguous fragments, in any order, and including all lengths of a polypeptide composition set forth herein, or those encoded by a polynucleotide sequence set forth herein. In another aspect, fusion polypeptides of the present invention may comprise two or more *Leishmania* antigen fragments as recited in SEQ ID NOs: 1-10, and 25-28 or immunogenic portion thereof. In a particular embodiment, the fusion polypeptide comprises an amino acid sequence set forth in any one of SEQ ID NOs: 21, 23, 33, 35 or 37.

In yet another aspect, the present invention provides fusion polypeptides comprising two or more, three or more, or four or more variants of the *Leishmania* KMP11, SMT, A2 and/or CPB polypeptides described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

The compositions and methods of the present invention also encompass variants of the above polypeptides. Certain polypeptide "variants," include polypeptides that differ from a native KMP11, SMT, A2 and/or CPB protein in one or more substitutions, deletions, additions and/or insertions, such that the desired immunogenicity of the variant polypeptide is not substantially diminished relative to a native KMP11, SMT, A2 and/or CPB polypeptide.

For example, certain variants of the invention include polypeptides of the invention that have been modified to replace one or more cysteine residues with alternative residues. Such polypeptides are referred to hereinafter as cysteine-modified polypeptides or cysteine-modified fusion polypeptides. In a more specific embodiment, cysteine residues are replaced with serine residues because of the similarity in the spatial arrangement of their respective side chains. However, it will be apparent to one skilled in the art that any amino acid that is incapable of interchain or intrachain disulfide bond formation can be used as a replacement for cysteine. When all or substantially all of the cysteine residues in a polypeptide or fusion polypeptide of this invention are replaced, the resulting cysteine-modified variant may be less prone to aggregation and thus easier to purify, more homogeneous, and/or obtainable in higher yields following purification.

In one embodiment, the ability of a variant to react with antigen-specific antisera may be enhanced or unchanged, relative to the native protein, or may be diminished by less than 50%, and preferably less than 20%, relative to the native protein. In a particular embodiment, a variant of an KMP11, SMT, A2 and/or CPB polypeptide is one capable of providing protection, for example in an in vivo assay as described herein, against a *Leishmania* species such as *L. donovani*, *L. infantum* and/or *L. major*.

In particular embodiments, a fusion polypeptide of the present invention comprises at least 2, at least 3, at least 4, at least 5, at least 6, at least 7, at least 8, at least 9, or at least 10 or more variants of a *Leishmania* KMP11, SMT, A2 and/or CPB polypeptide that is capable of providing protection against, for example in an in vivo assay as described herein, or serodiagnosis of *Leishmania* species such as *L. donovani*, *L. major* and/or *L. infantum*.

A fusion polypeptide of the present invention comprises two or more, three or more, four or more, five or more, six or more, seven or more, eight or more, nine or more, or ten or more variants of a *Leishmania* KMP11, SMT, A2 and/or CPB polypeptide that is capable of serodiagnosis of *Leishmania* species such as *L. donovani*, *L. major* and/or *L. infantum*.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-Histidine tag (6×His), GST, MBP, TAP/TAG, FLAG epitope, MYC epitope, V5 epitope, VSV-G epitope, etc.), or to enhance binding of the polypeptide to a solid support. For example, a polypeptide may be conjugated to an immunoglobulin Fc region.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted using, for example, the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology vol.* 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, alignment of sequences for comparison may be conducted by the local identity algorithm of Smith and Waterman (1981) *Add. APL. Math* 2:482, by the identity alignment algorithm of Needleman and Wunsch (1970) J. Mol. Biol. 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, as noted above, the present invention encompasses polynucleotide and polypeptide sequences having substantial identity to the sequences disclosed herein, for example those comprising at least 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like. Furthermore, it would be understood by of ordinary skill in the art that fusion polypeptides of the present invention may comprise at least 2, at least 3, or at least 4 or more antigenic/immunogenic portions or fragments of a polypeptide comprising at least 70%, 75%, 80%, 85%, 90%, 95%, 96%, 97%, 98%, or 99% or higher, sequence identity to a *Leishmania* KMP11, SMT, A2 and/or CPB polypeptide that is capable of providing protection against, for example in an in vivo assay as described herein, or serodiagnosis of *Leishmania* species such as *L. donovani, L. major* and/or *L. infantum.*

In another aspect of the invention, fusion polypeptides are provided that comprise at least an immunogenic portion of a *Leishmania* KMP11, SMT, A2 and/or CPB polypeptide and further comprise a heterologous fusion partner, as well as polynucleotides encoding such fusion polypeptides. For example, in one embodiment, a fusion polypeptide comprises one or more immunogenic portions or fragments of a *Leishmania* KMP11, SMT, A2 and/or CPB polypeptide and one or more additional immunogenic *Leishmania* sequences, which are joined via a peptide linkage into a single amino acid chain. In another embodiment, a fusion polypeptide may comprise multiple *Leishmania* antigenic epitopes wherein at least one of the epitopes is from a *Leishmania* KMP11, SMT, A2 and/or CPB polypeptide. As used herein an "epitope" is a portion of an antigen that reacts with blood samples from *Leishmania*-infected individuals (i.e. an epitope is specifically bound by one or more antibodies and/or T-cells present in such blood samples.

In another embodiment, a fusion polypeptide may comprise multiple *Leishmania* antigenic epitopes wherein at least one of the epitopes is from a *Leishmania* KMP11, SMT, A2 and/or CPB polypeptide and at least one heterologous fusion partner comprises a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners include both immunological and expression-enhancing fusion partners. Other fusion partners may be selected so as to increase the solubility of the protein or to enable the protein to be targeted to desired intracellular compartments. Still further fusion partners include affinity tags, such as V5, 6XHIS, MYC, FLAG, and GST, which facilitate purification of the protein. It would be understood by one having ordinary skill in the art that those unrelated sequences may, but need not, be present in a fusion polypeptide used in accordance with the present invention. Within a particular embodiment, an immunological fusion partner comprises sequence derived from protein D, a surface protein of the gram-negative bacterium *Haemophilus influenza* B (WO 91/18926). For example, one protein D derivative comprises approximately the first third of the protein (e.g., the first N-terminal 100 110 amino acids), and a protein D derivative may be lipidated. Within certain embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other illustrative fusion partners include the non-structural protein from influenzae virus, NS1 (hemaglutinin). Typically, the N-terminal 81 amino acids are used, although different fragments that include T-helper epitopes may also be used.

In another particular embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LYTA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a particular embodiment, a repeat portion of LYTA may be incorporated into a fusion protein. A repeat portion is found in the C-terminal region starting at residue 178. A more particular repeat portion incorporates residues 188-305.

Fusion sequences may be joined directly (i.e., with no intervening amino acids) or may be joined by way of a linker sequence (e.g., Gly-Cys-Gly) that does not significantly diminish the immunogenic properties of the component polypeptides. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein.

Fusion polypeptides may generally be prepared using standard techniques, including recombinant technology, chemical conjugation and the like. For example, DNA sequences encoding the polypeptide components of a fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion polypeptide that retains or in some cases exceeds the biological activity of the component polypeptides.

A peptide linker sequence may be employed to separate the fusion components by a distance sufficient to ensure that each polypeptide folds into its desired secondary and/or tertiary structures. Such a peptide linker sequence may be incorporated into the fusion polypeptide using standard techniques well known in the art. Suitable peptide linker sequences may be chosen, for example, based on one or more of the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Certain preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In addition to recombinant fusion polypeptide expression, *Leishmania* KMP11, SMT, A2 and/or CPB polypeptides, immunogenic portions and variants thereof may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, *J. Am. Chem. Soc.* 85:2149-2146, 1963). Equipment for automated synthesis of polypeptides is commercially available from suppliers such as Perkin Elmer/Applied BioSystems Division, Foster City, Calif., and may be operated according to the manufacturer's instructions. Thus, for example, *Leishmania* KMP11, SMT, A2 and/or CPB antigens, or portions thereof, may be synthesized by this method.

Recombinant polypeptides containing portions and/or variants of a native KMP11, SMT, A2 and/or CPB polypeptide may be readily prepared from a DNA sequence encoding the antigen, using well known and established techniques. In particular embodiments, a fusion polypeptide comprising at least 2 immunogenic/antigenic portions or fragments of *Leishmania* KMP11, SMT, A2 and/or CPB antigens may be readily prepared from a DNA sequence encoding the cloned fused antigens. For example, supernatants from suitable host/vector systems which secrete recombinant protein into culture media may be first concentrated using a commercially available filter. Following concentration, the concentrate may be applied to a suitable purification matrix such as an affinity matrix, a size exclusion chromatography matrix or an ion exchange resin.

Alternatively, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Preferably, the host cells are *E. coli*, yeast, an insect cell line (such as *Spodoptera* or *Trichoplusia*) or a mammalian cell line, including (but not limited to) CHO, COS, HEK-293T and NS-1. The DNA sequences expressed in this manner may encode naturally occurring proteins, and fusion proteins comprising *Leishmania* antigens such as KMP11, SMT, A2 and/or CPB, portions thereof, and repeats or other variants of such proteins. Expressed fusion polypeptides of this invention are generally isolated in substantially pure form. Preferably, the fusion polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

*Leishmania* KMP11, SMT, A2 and/or CPB polypeptides and polynucleotides of the invention may be prepared or isolated using any of a variety of procedures and using any of a variety of *Leishmania* species including, but not limited to, *L. donovani, L. chagasi, L. infantum, L. major, L. amazonensis, L. braziliensis, L. panamensis, L. mexicana, L. tropica*, and *L. guyanensis*. Such species are available, for example, from the American Type Culture Collection (ATCC), Rockville, Md.

Regardless of the method of preparation, the KMP11, SMT, A2 and/or CPB polypeptides or fusion polypeptides produced as described above are preferably immunogenic. In other words, the polypeptides (and immunogenic portions thereof) are capable of eliciting an immune response in cultures of lymph node cells and/or peripheral blood mononuclear cells (PBMC) isolated from presently or previously *Leishmania*-infected individuals. More specifically, the antigens, and immunogenic portions thereof, have the ability to induce T-cell proliferation and/or to elicit a dominantly Th1-type cytokine response (e.g., IL-2, IFN-γ, and/or TNF-α production by T-cells and/or NK cells; and/or IL-12 production by monocytes, macrophages and/or B cells) in cells isolated from presently or previously *Leishmania*-infected individuals. A *Leishmania*-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with, for example, at least one of the following: isolation of parasite from lesions, a positive skin test with *Leishmania* lysate or a positive serodiagnostic test. Asymptomatic individuals are infected individuals who have no signs or symptoms of the disease. Such individuals can be identified, for example, based on a positive serological test and/or skin test with *Leishmania* lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, FICOLL™ solution (Winthrop Laboratories, New York). Lymph node cultures may generally be prepared by immunizing BALB/c mice (e.g., in the rear foot pad) with *Leishmania* promastigotes emulsified in complete Freünd's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a fusion polypeptide of the invention to induce a response in PBMC or lymph node cell cultures may be evaluated, for example, by contacting the cells with the polypeptide and measuring a suitable response. In general, the amount of polypeptide that is sufficient for the evaluation of about $2 \times 10^5$ cells ranges from about 10 ng to about 100 μg or 100 ng to about 50 μg, and preferably is about 1 μg, to 10 μg. The incubation of polypeptide (e.g., a fusion polypeptide) with cells is typically performed at 37° C. for about 1-3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-γ (IFN-γ), interleukin-4 (IL-4), interleukin-12 (p70 and/or p40), interleukin-2 (IL-2) and/or tumor necrosis factor-α (TNF-α)) or the change in the level of mRNA encoding one or more specific cytokines. For example, the secretion of interferon-γ, interleukin-2, tumor necrosis factor-α and/or interleukin-12 is indicative of a Th1 response, which contributes to the protective effect against *Leishmania*. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3 \times 10^5$ cells, the production of 30 pg/mL of IL-12, IL-4, IFN-γ, TNF-α or IL-12 p40, or 10 μg/mL of IL-12 p70, is considered able to stimulate production of a cytokine.

Polynucleotide Compositions

The present invention also provides isolated polynucleotides, particularly those encoding the fusion polypeptides of the invention, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, fusion polypeptides, peptides and the like. Such segments may be naturally isolated, recombinant, or modified synthetically by the hand of man.

As will be recognized by the skilled artisan, polynucleotides may be single-stranded (coding or antisense) or double-stranded, and may be DNA (genomic, cDNA or synthetic) or RNA molecules. Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Leishmania* antigen or a portion thereof) or may comprise a variant, or a biological or antigenic functional equivalent of such a sequence. In particular embodiments, polynucleotides may encode for two or more antigenic/immunogenic portions, fragments, or variants derived from the *Leishmania* KMP11, SMT, A2 and/or CPB antigens. In certain embodiments, polynucleotides encoding fusion polypeptides of the present invention comprise two or more *Leishmania* antigen sequences as recited in SEQ ID NOs: 11-20 and 29-32 or a fragment thereof encoding an immunogenic portion. In a related aspect, polynucleotides as set forth in SEQ ID NOs: 22 or 24 are provided, which encode particular fusion polypeptides of the present invention.

Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein.

For example, in certain embodiments, variants of the invention include cysteine-modified polynucleotides in which the cysteine-encoding codons are replaced with codons encoding other amino acids not capable of forming intrachain or interchain disulfide bonds. In more specific embodiments, some or all of the replacement codons encode serine because of the spatial similarity of the serine sidechain to the cysteine sidechain in the resulting polypeptide. In another specific embodiment, some or all of the replacement codons encode alanine. Illustrative methods of replacing cysteine and other codons within a polynucleotide are well known (e.g., U.S. Pat. No. 4,816,566, the contents of which are incorporated herein by reference, and Proc Natl Acad Sci 97 (15): 8530, 2000).

The term "variants" also encompasses homologous genes of xenogenic origin.

In additional embodiments, isolated polynucleotides of the present invention comprise various lengths of contiguous stretches of sequence identical to or complementary to two or more KMP11, SMT, A2 and/or CPB, such as those sequences disclosed herein. For example, polynucleotides are provided by this invention that comprise at least about 15, 20, 30, 40, 50, 75, 100, 150, 200, 300, 400, 500 or 1000 or more contiguous nucleotides of two or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage dare specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Leishmania* polynucleotides and fusions thereof may be prepared, manipulated and/or expressed using any of a variety of well established techniques known and available in the art. In particular embodiments, fusions comprise two or more polynucleotide sequences encoding *Leishmania* KMP11, SMT, A2 and/or CPB antigens.

For example, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide of the present invention.

As will be understood by those of skill in the art, it may be advantageous in some instances to produce fusion polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter fusion polypeptide encoding sequences for a variety of reasons, including but not limited to, alterations which modify the cloning, processing, expression and/or immunogenicity of the gene product.

In order to express a desired fusion polypeptide comprising two or more antigenic/immunogenic fragments or portions of KMP11, SMT, A2 and/or CPB polypeptides, a nucleotide sequence encoding the fusion polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (January 2008, updated edition).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast (such as *Saccharomyces* or *Pichia*) transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as PBLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. PGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a fusion polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed fusion protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a fusion polynucleotide of the present invention may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. In addition to recombinant production methods, fusion polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments, for example, two or more antigenic/immunogenic fragments from *Leishmania* KMP11, SMT, A2, and/or CBP antigens, may be chemically synthesized separately and combined using chemical methods to produce the full length molecule.

Pharmaceutical and Vaccine Compositions

In certain aspects, the polypeptides, polynucleotides, portions, variants, fusion polypeptides, etc., as described herein, are incorporated into pharmaceutical compositions or vaccines. Pharmaceutical compositions generally comprise one or more polypeptides, polynucleotides, portions, variants, fusion polypeptides, etc., as described herein, in combination with a physiologically acceptable carrier. Vaccines, also referred to as immunogenic compositions, generally comprise one or more of the polypeptides, polynucleotides, portions, variants, fusion proteins, etc., as described herein, in combination with an immunostimulant, such as an adjuvant. In particular embodiments, the pharmaceutical compositions comprise fusion polypeptides further containing at least 2, at least 3, or at least 4 or more *Leishmania* KMP11, SMT, A2 and/or CPB polypeptide antigens that are capable of providing protection against, for example in an in vivo assay as described herein, *Leishmania* species such as *L. donovani, L. major* and/or *L. infantum*.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), Bordatella pertussis or *Mycobacterium* species or *Mycobacterium*-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (GlaxoSmithKline Beecham, Philadelphia, Pa.); CWS, TDM, LeIF, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Certain embodiments of the present invention contemplate vaccine and pharmaceutical compositions that include one or more toll-like receptor agonists (TLR agonist). In more specific embodiments, for example, the compositions of the invention include Toll-like receptor agonists, such as TLR7 agonists and TLR7/8 agonists. In certain embodiments the TLR agonist is capable of delivering a biological signal by interacting with at least one TLR that is selected from TLR-2, TLR-3, TLR-4, TLR-5, TLR-6, TLR-7, TLR-8 and TLR-9.

Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 *Genome Biol.* 3(8):reviews 3011.1-3011.6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335; Takeda et al. 2005 *Int. Immunol.* 17:1; Kaisho et al., 2004 *Microbes Infect.* 6:1388; Datta et al., 2003 *J. Immunol.* 170:4102).

Induction of TLR-mediated signal transduction to potentiate the initiation of immune responses via the innate immune system may be effected by TLR agonists, which engage cell surface TLR or cytoplasmic TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Phsiol.* 286:C739; Lin et al., 2005 *Shock* 24:206); poly(inosine-cytidine) (polyI:C) may be a TLR agonist through TLR3 (Salem et al., 2006 *Vaccine* 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG Bayes et al. *Methods Find Exp Clin Pharmacol* 27:193; Vollmer et al. *Expert Opinion on Biological Therapy* 5:673; Vollmer et al., 2004 *Antimicrob. Agents Chemother.* 48:2314; Deng et al., 2004 *J. Immunol.* 173:5148) may be TLR agonists through TLR9 (Andaloussi et al., 2006 *Glia* 54:526; Chen et al., 2006 *J. Immunol.* 177:2373); peptidoglycans may be TLR2 and/or TLR6 agonists (Soboll et al., 2006 *Biol. Reprod.* 75:131; Nakao et al., 2005 *J. Immunol.* 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 *Hepatol.* 42:724). Other TLR agonists are known (e.g., Schirmbeck et al., 2003 *J. Immunol.* 171:5198) and may be used according to certain of the presently described embodiments.

For example, and by way of background (see, e.g., U.S. Pat. No. 6,544,518) immunostimulatory oligonucleotides containing unmethylated CpG dinucleotides ("CpG") are known as being adjuvants when administered by both systemic and mucosal routes (WO 96/02555, EP 468520, Davis et al., *J. Immunol,* 1998. 160(2):870-876; McCluskie and Davis, *J. Immunol.,* 1998, 161(9):4463-6). CpG is an abbreviation for cytosine-guanosine dinucleotide motifs present in DNA. The central role of the CG motif in immunostimulation was elucidated by Krieg, *Nature* 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., *Proc. Natl. Acad. Sci.,* USA, 1998, 95(26), 15553-8).

Other illustrative oligonucleotides for use in compositions of the present invention will often contain two or more dinucleotide CpG motifs separated by at least three, more preferably at least six or more nucleotides. The oligonucleotides of the present invention are typically deoxynucleotides. In one embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Other examples of oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9.

CpG 10101: Bayes et al., "Gateways to clinical trials." Methods Find. Exp. Clin. Pharmacol. 2005 April; 27(3):193-219.

Vollmer J., "Progress in drug development of immuno-stimula-tory CpG oligodeoxynucleotide ligands for TLR9." Expert Opinion on Biological Therapy. 2005 May; 5(5): 673-682

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilising an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phosphodiesters. Other internucleotide bonds which stabilize the oligonucleotide may also be used.

In certain more specific embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen.

Still other illustrative adjuvants include imiquimod, gardiquimod and resiquimod (all available from Invivogen), and related compounds, which are known to act as TLR7/8 agonists. A compendium of adjuvants that may be useful in vaccines is provided by Vogel et al., Pharm Biotechnol 6:141 (1995), which is herein incorporated by reference.

Compositions of the invention may also employ adjuvant systems designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine comprising a fusion polypeptide further comprising at least 2, at least 3, or at least 4 or more *Leishmania* KMP11, SMT, A2 and/or CPB polypeptide antigens, as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, *Ann. Rev. Immunol.* 7:145-173 (1989).

Certain adjuvants for use in eliciting a predominantly Th1-type response include, for example, a combination of monophosphoryl lipid A, preferably 3-de-O-acylated monophosphoryl lipid A (3D-MPL™), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other illustrative formulations include more than one saponin in the adjuvant combinations of the present invention, for example combinations of at least two of the following group comprising QS21, QS7, Quil A, β-escin, or digitonin.

In a particular embodiment, the adjuvant system includes the combination of a monophosphoryl lipid A and a saponin derivative, such as the combination of QS21 and 3D-MPL™ adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL™ adjuvant and tocopherol in an oil-in-water emulsion is described in WO 95/17210.

In certain preferred embodiments, the adjuvant used in the present invention is a glucopyranosyl lipid A (GLA) adjuvant, as described in U.S. Patent Application Publication No. 20080131466, the disclosure of which is incorporated herein by reference in its entirety. For example, in one embodiment, the GLA adjuvant used in the context of the present invention has the following structure:

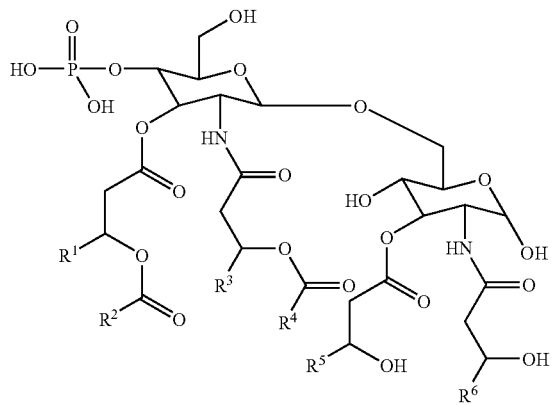

where: $R^1$, $R^3$, $R^5$ and $R^6$ are $C_{11}$-$C_{20}$ alkyl; and $R^2$ and $R^4$ are $C_{12}$-$C_{20}$ alkyl.

In a more specific embodiment, the GLA has the formula set forth above wherein $R^1$, $R^3$, $R^5$ and $R^6$ are $C_{11-14}$ alkyl; and $R^2$ and $R^4$ are $C_{12-15}$ alkyl.

In a more specific embodiment, the GLA has the formula set forth above wherein $R^1$, $R^3$, $R^5$ and $R^6$ are $C_{11-14}$ alkyl; and $R^2$ and $R^4$ are $C_{1-3}$ alkyl.

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

The vaccine and pharmaceutical compositions of the invention may be formulated using any of a variety of well known procedures. In certain embodiments, the vaccine or pharmaceutical compositions are prepared as stable emulsions (e.g., oil-in-water emulsions) or as aqueous solutions.

Compositions of the invention may also, or alternatively, comprise T cells specific for fusion polypeptide comprising at least 2 immunogenic/antigenic portions or fragments of *Leishmania* KMP11, SMT, A2 and/or CPB antigens or variants thereof, described herein. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a fusion polypeptide comprising at least 2 immunogenic/antigenic portions or fragments of *Leishmania* KMP11, SMT, A2 and/or CPB antigens or variants thereof, polynucleotide encoding such a fusion polypeptide, and/or an antigen presenting cell (APC) that expresses such a fusion polypeptide. Such stimulation is performed under conditions and for a time sufficient to permit the generation of T cells that are specific for the polypeptide. In certain embodiments, the polypeptide or polynucleotide is present within a delivery vehicle, such as a microsphere, to facilitate the generation of specific T cells.

T cells are considered to be specific for a fusion polypeptide comprising at least 2 immunogenic/antigenic portions or fragments of *Leishmania* KMP11, SMT, A2 and/or CPB antigens if the T cells specifically proliferate, secrete cytokines or kill target cells coated with the fusion polypeptide or expressing a gene encoding the fusion polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 μg/ml, preferably 200 ng/ml-25 μg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+.

Protein-specific T cells may be expanded using standard techniques. Within preferred embodiments, the T cells are derived from a patient, a related donor or an unrelated donor, and are administered to the patient following stimulation and expansion.

In the compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous and intramuscular administration and formulation.

In certain applications, the compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective for treatment of leishmaniasis. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known to one of ordinary skill in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood to one of ordinary skill in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions of the present invention comprising a fusion polypeptide with at least 2 immunogenic/antigenic portions or fragments of *Leishmania* KMP11, SMT, A2 and/or CPB antigens or variants thereof may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of compositions comprising a fusion polypeptide as describe herein into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

A pharmaceutical or immunogenic composition may, alternatively, contain an immunostimulant and a DNA molecule encoding one or more of the polypeptides or fusion polypeptides comprising two or more *Leishmania* KMP11, SMT, A2 and/or CPB polypeptides or immunogenic portions or variants thereof as described above, such that a desired polypeptide is generated in situ. In such compositions, the DNA encoding the fusion protein may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a particular embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells.

The pharmaceutical compositions and vaccines of the invention, which comprise two or more *Leishmania* KMP11, SMT, A2 and/or CPB polypeptides or immunogenic/antigenic portions, fragments or variants thereof, or polynucleotides encoding such polypeptides, portions, fragments or variants, may be used, for example, to induce protective immunity against *Leishmania* species such as *L. donovani, L. major* and/or *L. infantum* in a patient, such as a human or a dog, to prevent leishmaniasis or diminish its severity. The compositions and vaccines may also be used to stimulate an immune response, which may be cellular and/or humoral, in a patient, for treating an individual already infected. In one embodiment, for *Leishmania*-infected patients, the immune responses generated include a preferential Th1 immune response (i.e., a response characterized by the production of the cytokines interleukin-1, interleukin-2, interleukin-12 and/or interferon-γ, as well as tumor necrosis factor-α). In another embodiment, for uninfected patients, the immune response involves production of interleukin-12 and/or interleukin-2, or the stimulation of gamma delta T-cells. In either category of patient, the response stimulated may include IL-12 production. Such responses may also be elicited in biological samples of PBMC or components thereof derived from *Leishmania*-infected or uninfected individuals. As noted above, assays for any of the above cytokines, as well as other known cytokines, may generally be performed using methods known to those of ordinary skill in the art, such as an enzyme-linked immunosorbent assay (ELISA).

Appropriate doses and methods of fusion polypeptide administration for these purposes can be readily determined by a skilled artisan using available knowledge in the art and/or routine techniques. Routes and frequency of administration, as well as dosage, for the above aspects of the present invention may vary from individual to individual and may parallel those currently being used in immunization against other infections, including protozoan, viral and bacterial infections. For example, in one embodiment, between 1 and 12 doses of composition having a fusion polypeptide, which comprises two or more *Leishmania* KMP11, SMT, A2 and/or CPB polypeptides or immunogenic/antigenic portions, fragments or variants thereof, are administered over a 1 year period. Booster vaccinations may be given periodically thereafter as needed or desired. Of course, alternate protocols may be appropriate for individual patients. In a particular embodiment, a suitable dose is an amount of fusion polypeptide or DNA encoding such a peptide that, when administered as described above, is capable of eliciting an immune response in an immunized patient sufficient to protect the patient from leishmaniasis caused by *Leishmania* species such as *L. donovani, L. major* and/or *L. infantum* for at least 1-2 years. In general, the amount of fusion polypeptide present in a dose (or produced in situ by the DNA in a dose) ranges from about 100 ng to about 1 mg per kg of host, typically from about 10 µg to about 100 µg. Suitable dose sizes will vary with the size of the patient, but will typically range from about 0.1 mL to about 5 mL.

Diagnostic Methods and Kits

In another aspect, this invention provides compounds and methods for detecting leishmaniasis in individuals and in blood supplies. In particular embodiments, the individual is a mammal. In more particular embodiments, the mammal is a human or canine.

The fusion polypeptides and polynucleotides of the present invention are also useful as diagnostic reagents for detecting and/or monitoring *Leishmania* infection in a patient. For example, the compositions, fusion polypeptides, and polynucleotides of the invention may be used in in vitro and in vivo assays for detecting humoral antibodies or cell-mediated immunity against *Leishmania* for diagnosis of infection, monitoring of disease progression or test-of-cure evaluation. In particular embodiments, the fusion polypeptides and polynucleotides are useful diagnostic for serodiagnosis and whole blood assay in patients having leishmaniasis caused by *Leishmania* species such as *L. donovani, L. major* and/or *L. infantum*.

In one aspect, the diagnostic methods and kits preferably employ a fusion polypeptide comprising multiple copies of polypeptide fragments, repeats of polypeptide fragments, or multimeric polypeptide fragments, including antigenic/immunogenic fragments such as *Leishmania* KMP11, SMT, A2 and/or CPB polypeptides, comprising at least about 1, 2, 3, 4, 5, 6, 7, 8, 9, 10 or more contiguous fragments, in any order, and including all lengths of a polypeptide composition set forth herein, or those encoded by a polynucleotide sequence set forth herein. In another aspect, fusion polypeptides of the present invention may comprise two or more *Leishmania* antigen fragments as recited in SEQ ID NOs: 1-10, and 25-28. In a more particular embodiment, the fusion polypeptide comprises the amino acid sequence set forth in SEQ ID NOs: 21 or 23.

In another embodiment, the diagnostic methods and kits preferably employ a fusion polypeptide comprising at least 1, at least 2, at least 3, or at least 4 immunogenic/antigenic portion or fragment of *Leishmania* KMP11, SMT, A2 and/or CPB antigens, variants or the like, optionally in combination with one or more other *Leishmania* antigens as described herein, or obtainable in the art. In certain embodiments, it will be preferred to use a multiple *Leishmania* antigens as described herein, e.g., 3 or more, 4 or more, 5 or more, 6 or more, 7 or more, 8 or more, 9 or more, 10 or more, etc., in a diagnostic method of the invention. The antigens may be used in essentially any assay format desired, e.g., as individual antigens assayed separately, as multiple antigens assays simultaneously (e.g., a fusion polypeptide such as KSA or KSAC), as antigens immobilized on a solid support such as an array, or the like.

In one embodiment, there are provided diagnostic kits for detecting *Leishmania* infection in a biological sample, comprising (a) a fusion polypeptide comprising at least 2 immunogenic/antigenic portions or fragments of *Leishmania* KMP11, SMT, A2 and/or CPB polypeptide or variant thereof described herein, and (b) a detection reagent.

In another embodiment, there are provided diagnostic kits for detecting *Leishmania* infection in a biological sample, comprising (a) at least 2 antibodies or antigen binding fragments thereof that are specific for a fusion polypeptide comprising at least 2 immunogenic/antigenic portions or fragments of *Leishmania* KMP11, SMT, A2 and/or CPB polypeptide or variant thereof described herein, and (b) a detection reagent.

In another embodiment, methods are provided for detecting the presence of *Leishmania* infection in a biological sample, comprising (a) contacting a biological sample with a fusion polypeptide comprising at least 2 immunogenic/antigenic portions or fragments of *Leishmania* KMP11, SMT, A2 and/or CPB polypeptide or variant thereof described herein; and (b) detecting in the biological sample the presence of antibodies that bind to the fusion polypeptide.

In another embodiment, methods are provided for detecting the presence of *Leishmania* infection in a biological sample, comprising (a) contacting a biological sample with at least 2 monoclonal antibodies that bind to a fusion polypeptide comprising at least 2 immunogenic/antigenic portions or fragments of *Leishmania* KMP11, SMT, A2 and/or CPB polypeptide or variant thereof described herein; and (b) detecting in the biological sample the presence of *Leishmania* proteins that bind to the monoclonal antibody.

One of ordinary skill in the art would recognize that the methods and kits described herein may be used to detect all types of leishmaniasis, depending on the particular combination of immunogenic portions of *Leishmania* antigens present in the fusion polypeptide.

There are a variety of assay formats known to those of ordinary skill in the art for using a fusion polypeptide to detect antibodies in a sample. See, e.g., Harlow and Lane, Antibodies. A Laboratory Manual, Cold Spring Harbor Laboratory Press, 1988, which is incorporated herein by reference. In a preferred embodiment, the assay involves the use of fusion polypeptide immobilized on a solid support to bind to and remove the antibody from the sample. The bound antibody may then be detected using a detection reagent that binds to the antibody/peptide complex and contains a detectable reporter group. Suitable detection reagents include, for example, antibodies that bind to the antibody/polypeptide complex and free polypeptide labeled with a reporter group (e.g., in a semi-competitive assay). Suitable reporter groups include, for example, fluorescent labels, enzyme labels, radioisotopes, chemiluminescent labels, electrochemiluminescent labels, bioluminescent labels, polymers, polymer particles, metal particles, haptens, and dyes. Alternatively, a competitive assay may be utilized, in which an antibody that binds to a fusion polypeptide of the present invention labeled with a reporter group and allowed to bind to the immobilized fusion polypeptide after incubation of the fusion polypeptide with the sample. The extent to which components of the sample inhibit the binding of the labeled antibody to the fusion polypeptide is indicative of the reactivity of the sample with the immobilized fusion polypeptide.

The solid support may be any material known to those of ordinary skill in the art to which the fusion polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The fusion polypeptide may be bound to the solid support using a variety of techniques known to those in the art, which are amply described in the patent and scientific literature. In the context of the present invention, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 µg, and preferably about 100 ng, is sufficient to bind an adequate amount of antigen. Nitrocellulose will bind approximately 100 µg of protein per $cm^3$.

Covalent attachment of fusion polypeptide to a solid support may generally be achieved by first reacting the support with a bifunctional reagent that will react with both the support and a functional group, such as a hydroxyl or amino group, on the fusion polypeptide. For example, the fusion polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a fusion polypeptide of the present invention that has been immobilized on a solid support, commonly the well of a microtiter plate, with the sample, such that antibodies to the *Leishmania* antigens of the fusion polypeptide within the sample are allowed to bind to the immobilized fusion polypeptide. Unbound sample is then removed from the immobilized fusion polypeptide and a detection reagent capable of binding to the immobilized antibody-polypeptide complex is added. The amount of detection reagent that remains bound to the solid support is then determined using a method appropriate for the specific detection reagent.

Once the fusion polypeptide is immobilized on the support, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detection of the presence of antibody within a Leishmania-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups, colloidal gold and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Leishmania antibodies in the sample, the signal detected from the reporter group that remains bound to the solid support is generally compared to a signal that corresponds to a predetermined cut-off value. In one embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized fusion polypeptide. Concentration of detection reagent at the fusion polypeptide indicates the presence of Leishmania antibodies in the sample. Typically, the concentration of detection reagent at that site generates a pattern, such as a line, that can be read visually. The absence of such a pattern indicates a negative result. In general, the amount of fusion polypeptide immobilized on the membrane is selected to generate a visually discernible pattern when the biological sample contains a level of antibodies that would be sufficient to generate a positive signal in an ELISA, as discussed above. Preferably, the amount of fusion polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the fusion polypeptides of the present invention. The above descriptions are intended to be exemplary only.

In one aspect of the invention, the assays discussed above may be used to specifically detect visceral leishmaniasis. In this aspect, antibodies in the sample may be detected using a fusion polypeptide of the present invention, e.g., comprising an amino acid sequence of two or more antigenic/immunogenic fragments or epitopes of a Leishmania KMP11, SMT, A2 and/or CPB antigen. In a more particular embodiment, antibodies in the sample may be detected using a fusion polypeptide comprising the amino acid sequence of two or more immunogenic fragments or epitopes as set forth in any of SEQ ID NOs: 1-10 and 25-28. In another aspect, antibodies in the sample may be detected using a fusion polypeptide comprising the amino acid sequence set forth in SEQ ID NOs: 21 and 23. Preferably, the Leishmania antigens are immobilized by adsorption to a solid support such as a well of a microtiter plate or a membrane, as described above, in roughly similar amounts such that the total amount of fusion polypeptide in contact with the support ranges from about 10 ng to about 100 μg. The remainder of the steps in the assay may generally be performed as described above. It will be readily apparent to those of ordinary skill in the art that, by combining polypeptides described herein with other polypeptides that can detect cutaneous and mucosal leishmaniasis, the polypeptides disclosed herein may be used in methods that detect all types of leishmaniasis.

In another aspect of this invention, immobilized fusion polypeptides may be used to purify antibodies that bind thereto. Such antibodies may be prepared by any of a variety of techniques known to those of ordinary skill in the art. See, e.g., Harlow and Land, Antibodies. A Laboratory Manual, Cold Spring Harbor Laboratory Press, 1988. In one such technique, an immunogen comprising a fusion polypeptide of the present invention is initially injected into any of a wide variety of mammals (e.g., mice, rats, rabbits, sheep and goats). In this step, the polypeptide may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic fusion polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more polypeptides may be used in the purification process in, for example, an affinity chromatography step.

Monospecific antibodies that bind to a fusion polypeptide comprising two or more immunogenic portions of *Leishmania* K26, K39, and/or K9 antigens may be used, for example, to detect *Leishmania* infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen and the remainder of the sample and antibody is removed. The level of antibody bound to the solid support is inversely related to the level of antigen in the sample. Thus, a lower level of antibody bound to the solid support indicates the presence of *Leishmania* in the sample. Other formats for using monospecific antibodies to detect *Leishmania* in a sample will be apparent to those of ordinary skill in the art, and the above formats are provided solely for exemplary purposes.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Mice Immunized with KSA or KSAC are Protected Against *L. Infantum* Infection

C57BL/6 mice (Charles River Laboratories, Wilmington, Mass.), were maintained in specific-pathogen-free conditions. Mice were eight to twelve-week-old at the beginning of experiments. Promastigotes of *L. infantum* (MHOM/BR/82/BA-2) were cultured at 25° C. in MEM (Invitrogen, Carlsbad, Calif.) supplemented with 0.5×MEM essential amino acids solution (Invitrogen), 0.1 mM MEM non-essential amino acids (Invitrogen), 1 mM sodium pyruvate, 25 mM HEPES, 8.3 mM glucose, 26 mM sodium bicarbonate, 1 μg/ml para amino benzoic acid, 50 μg/ml gentamicin 10% heat-inactivated fetal bovine serum and 6 μg/ml hemin. Promastigotes in a late log or stationary phase were used for infections or Ag preparations.

Groups of five mice were immunized. The first group was immunized with saline as a negative control. The second group was immunized with 10 μg of SMT (e.g., SEQ ID NO:4) plus 20 μg of MPL®-SE (GlaxoSmithKline Biologicals, Rixensant, Belgium) in a volume of 0.1 ml. The third group was immunized with 10 μg of the KSA fusion polypeptide (e.g., SEQ ID NO:21) containing KMP11, SMT, and A2 plus 20 μg of MPL-SE® in a volume of 0.1 ml. The fourth group was immunized with 10 μg of the KSAC fusion polypeptide (e.g., SEQ ID NO:23) containing KMP11, SMT, A2, and CBP plus 20 μg of MPL-SE® in a volume of 0.1 ml.

Three subcutaneous (s.c.) injections were given at the base of the tail at 3-week intervals. Mice were infected 3 weeks after completion of the immunization protocol. As a challenge, $5 \times 10^6$ *L. infantum* promastigotes were suspended in 100 μl of phosphate buffered saline and injected intravenously into the mouse tail vein.

At four weeks after the challenge, mice were sacrificed to collect livers to determine the numbers of parasites in these tissues by limiting dilution assay. The tissues were homogenated with glass grinders and the suspensions were two-fold serially diluted with complete HOMEM in 96-well microplates with NNN blood agar. Each well was examined for the presence of parasites ten days after plating, and the numbers of parasites in the original tissues were calculated based on dilution factor of the last positive well (FIG. 1).

The results of this experiment demonstrated that mice immunized with KSA or KSAC fusion polypeptides were significantly protected against *L. infantum* infection.

Example 2

Mice Immunized with KSA or KSAC are Protected Against *L. Donovani* Infection

BALB/c mice (Charles River Laboratories) were maintained in specific-pathogen-free conditions. Mice were eight to twelve-week-old at the beginning of experiments. Promastigotes of *L. donovani* were grown at 25° C. in medium 199 supplemented with 20% heat-inactivated fetal bovine serum, 100 U of penicillin per ml, 100 μg of streptomycin per ml, 2 mM L-glutamine, 0.1 mM adenine, 40 mM HEPES, 0.25 mg of hemin per ml, and 0.31 mg of 6-biotin per ml. Promastigotes in a late log or stationary phase were used for infections or Ag preparations.

Groups of five mice were immunized. The first group was immunized with saline as a negative control. The second group was immunized with 10 μg of the KSA fusion polypeptide (e.g., SEQ ID NO: 21) containing KMP11, SMT, and A2 plus 20 μg of MPL-SE® in a volume of 0.1 ml. The third group was immunized with 10 μg of the KSAC fusion polypeptide (e.g., SEQ ID NO: 23) containing KMP11, SMT, A2, and CBP plus 20 μg of MPL-SE® in a volume of 0.1 ml.

Three subcutaneous (s.c.) injections were given at the base of the tail at 3-week intervals. Mice were infected 3 weeks after completion of the immunization protocol. As a challenge, $1 \times 10^7$ *L. donovani* promastigotes were suspended in 100 μl of phosphate buffered saline and injected intravenously into the mouse tail vein.

Figure 2:
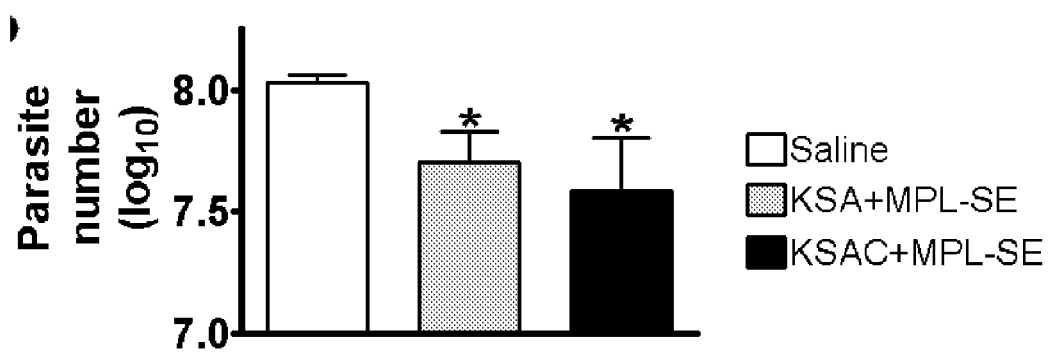
FIG. 2 shows protection against *L. donovani* infection by immunization with KSA or KSAC fusion polypeptides. BALB/c mice inoculated with saline alone, KSA+MPL-SE or KSAC+MPL-SE were challenged with *L. donovani*, and the numbers of parasites in the liver were measured by limiting dilution four weeks after the infection. Mean and SEM of five mice in each group are shown. *P<0.05 by unpaired t-test compared with the saline group.

At four weeks after the challenge, mice were sacrificed to collect livers to determine the numbers of parasites in these tissues by limiting dilution assay. The tissues were homogenated with glass grinders and the suspensions were twofold serially diluted with complete 199 medium in 96-well microplates with NNN blood agar. Each well was examined for the presence of parasites ten days after plating, and the numbers of parasites in the original tissues were calculated based on dilution factor of the last positive well (FIG. 2).

The results of this experiment demonstrated that mice immunized with KSA or KSAC fusion polypeptides were significantly protected against *L. donovani* infection.

Example 3

Mice Immunized with KSAC are Protected Against *L. Major* Infection

BALB/c mice (Charles River Laboratories) were maintained in specific-pathogen-free conditions. Mice were eight to twelve-week-old at the beginning of experiments. Promastigotes of *L. major* (MHOM/IL/80/Friedlin) were grown at 25° C. in medium 199 supplemented with 20% heat-inactivated fetal bovine serum, 100 U of penicillin per ml, 100 μg of streptomycin per ml, 2 mM L-glutamine, 0.1 mM adenine, 40 mM HEPES, 0.25 mg of hemin per ml, and 0.31 mg of 6-biotin per ml. Promastigotes in a late log or stationary phase were used for infections or Ag preparations.

Groups of five mice were immunized. The first group was immunized with saline as a negative control. The second group was immunized with 10 μg of the KSAC fusion polypeptide (e.g., SEQ ID NO: 23) containing KMP11, SMT, A2, and CBP plus 20 μg of MPL-SE® in a volume of 0.1 ml.

As a challenge, 2,000 *L. major* promastigotes were suspended in 10 μl of phosphate buffered saline and injected intradermally into both the left and right ears. Mice were infected 3 weeks after completion of the immunization protocol.

Figure 3:
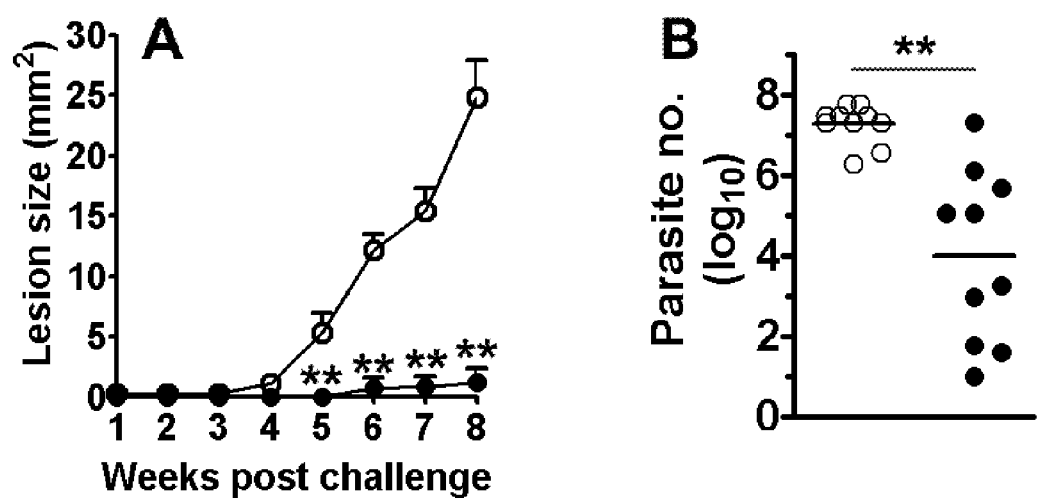
FIG. 3 shows protection against *L. major* infection by immunization with a KSAC fusion polypeptide. BALB/c mice inoculated with saline (open circles/bars) or KSAC+ MPL-SE (closed circles/bars) were challenged with *L. major* intradermally into the both right and left ears. (A) Lesion sizes and were measured every week up to 8 wks. Mean and SEM of five mice in each group are shown. (B) The numbers of parasites in the ear lesions were measured at 8 wks of the infection by limiting dilution.

The progress of infection was monitored every week for eight weeks by measuring the diameter of the induration of the ear lesion with a metric caliper (FIG. 3A).

At eight weeks after the challenge, ear tissue was collected to determine the numbers of parasites by limiting dilution assay. The tissue was homogenated with grinders and the suspensions were twofold serially diluted with complete 199 medium in 96-well microplates with NNN blood agar. Each well was examined for the presence of parasites ten days after plating, and the numbers of parasites in the original tissues were calculated based on dilution factor of the last positive well (FIG. 3B).

The results of this experiment demonstrated that mice immunized with KSAC fusion polypeptides were significantly protected against *L. major* infection.

Example 4

KSAC Immunization of Canines

Dogs with visceral leishmaniasis are vaccinated subcutaneously with KSAC (SEQ ID NO: 21)+adjuvant weekly for 6 weeks. The KSAC is administered at a dose of 25 μg and the adjuvant, MPL-SE (a TLR-4 agonist) is administered at a dose of 25 μg. In some studies the TLR-9 agonist CgG 2395 (500 μg) is administered instead of, or in addition, to the MPL-SE. After a two month pause, 3 additional vaccines are administered subcutaneously at weekly intervals. Dogs entered in the study have clinical scores of 4 to 7 out of a possible 16, where the higher number is indicative of more severe disease. Parasite burden is monitored in the bone marrow, spleen, lymph nodes and skin. Immune responses to the vaccine are monitored in blood.

As would be recognized by the skilled artisan, these and other changes can be made to the embodiments of the invention in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A fusion polypeptide comprising the amino acid sequence set forth as SEQ ID NO:33, or a sequence having at least 90% identity to SEQ ID NO:33.

2. The fusion polypeptide of claim 1, wherein the fusion polypeptide comprises the amino acid sequence set forth as SEQ ID NO:33.

3. The fusion polypeptide of claim 1, wherein the fusion polypeptide comprises a sequence having at least 95% identity to SEQ ID NO: 33.

4. A composition comprising a fusion polypeptide comprising the amino acid sequence set forth as SEQ ID NO:33 or a sequence haying at least 90% identity to SEQ ID NO:33 and at least one immunostimulant.

5. The composition according to claim 4, wherein the immunostimulant is selected from the group consisting of a CpG-containing oligonucleotide, synthetic lipid A, monophosphoryl lipid A, 3-de-O-acylated monophosphoryl lipid A, saponins, saponin mimetics, AGPs, Toll-like receptor agonists, or a combination thereof.

6. The composition according to claim 4, wherein the immunostimulant is selected from the group consisting of a TLR4 agonist, a TLR7/8 agonist and a TLR9 agonist.

7. The composition according to claim 4, wherein the immunostimulant is selected from the group consisting of GLA, CpG-containing oligonucleotide, imiquimod, gardiquimod and resiquimod.

8. The composition of claim 4, wherein the fusion polypeptide comprises the amino acid sequence set forth as SEQ ID NO: 33.

9. The composition of claim 4, wherein the fusion polypeptide comprises a sequence having at least 95% identity to SEQ ID NO: 33.

10. A diagnostic kit for detecting *Leishmania* infection in a biological sample comprising: (a) a fusion polypeptide comprising the amino acid sequence set forth as SEQ ID NO:33 or a sequence haying at least 90% identity to SEQ ID NO:33; and (b) a detection reagent.

11. The diagnostic kit of claim 10, wherein the fusion polypeptide comprises the amino acid sequence set forth as SEQ ID NO: 33.

12. The diagnostic kit of claim 10, wherein the fusion polypeptide comprises a sequence having at least 95% identity to SEQ ID NO: 33.

* * * * *

SEQUENCE LISTING

<160> NUMBER OF SEQ ID NOS: 38

<210> SEQ ID NO 1
<211> LENGTH: 92

```
<212> TYPE: PRT
<213> ORGANISM: Leishmania infantum

<400> SEQUENCE: 1

Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90

<210> SEQ ID NO 2
<211> LENGTH: 92
<212> TYPE: PRT
<213> ORGANISM: Leishmania donovani

<400> SEQUENCE: 2

Met Ala Thr Thr Tyr Glu Glu Phe Ser Ala Lys Leu Asp Arg Leu Asp
 1               5                  10                  15

Gln Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Arg Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90

<210> SEQ ID NO 3
<211> LENGTH: 92
<212> TYPE: PRT
<213> ORGANISM: Leishmania major

<400> SEQUENCE: 3

Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90

<210> SEQ ID NO 4
<211> LENGTH: 353
<212> TYPE: PRT
<213> ORGANISM: Leishmania infantum
```

<400> SEQUENCE: 4

```
Met Ser Ala Gly Gly Arg Glu Thr Ala Pro Thr Asn Leu Ile Arg Arg
 1               5                  10                  15
Arg Asn Lys Asp Glu Thr Asn Gly Asp Val Ser Ala Ala Ala Asp Arg
             20                  25                  30
Phe Arg Asp Arg Phe Glu Lys Ala Thr Leu Glu Glu Arg Lys Ala Ala
         35                  40                  45
Thr Thr Thr Met Val Asn Glu Tyr Tyr Asp Leu Val Thr Asp Phe Tyr
 50                  55                  60
Glu Tyr Gly Trp Gly Gln Asn Phe His Phe Ala Pro Arg Tyr Ala Gly
 65                  70                  75                  80
Glu Thr Phe Phe Glu Ser Leu Ala Arg His Glu Tyr Phe Leu Ala Ala
                 85                  90                  95
Arg Gly Gly Phe Met Glu Gly Asp His Ile Val Asp Val Gly Cys Gly
            100                 105                 110
Val Gly Gly Pro Ala Arg Asn Met Val Arg Leu Thr Arg Cys Asn Val
        115                 120                 125
Ile Gly Val Asn Asn Asn Asp Tyr Gln Ile Ser Arg Ala Arg Arg His
130                 135                 140
Asp Ala Leu Ala Gly Met Ser Ser Lys Ile Asp Tyr Val Lys Thr Asp
145                 150                 155                 160
Phe Cys Asn Met Ser Leu Ala Asp Asn Thr Phe Asp Gly Ala Tyr Ala
                165                 170                 175
Ile Glu Ala Thr Cys His Ala Lys Asp Lys Val Lys Cys Tyr Ser Glu
            180                 185                 190
Val Phe Arg Val Ile Lys Pro Gly Thr Cys Phe Val Leu Tyr Glu Trp
        195                 200                 205
Cys Met Thr Asp Lys Tyr Asn Pro Asn Asp Glu Tyr His Arg Thr Ile
210                 215                 220
Lys His Arg Ile Glu Leu Gly Asp Gly Leu Pro Glu Met Glu Thr Cys
225                 230                 235                 240
Lys Gln Val Ile Glu Tyr Met Lys Gln Ala Gly Phe Val Val Glu Glu
                245                 250                 255
Ala Ile Asp Val Ile Ser Gln Phe Glu Ser Ser Pro Ile Lys Ser Ile
            260                 265                 270
Pro Trp Tyr Gln Pro Leu Val Gly Asp Tyr Ser Ser Leu Gln Gly Leu
        275                 280                 285
Arg Ser Thr Pro Ile Gly Arg Ile Leu Thr Asn Val Met Cys Arg Val
290                 295                 300
Leu Glu Phe Val Arg Leu Ala Pro Lys Gly Thr Tyr Lys Ala Thr Glu
305                 310                 315                 320
Ile Leu Glu Glu Ala Ala Glu Ser Leu Val Val Gly Gln Leu Gly
                325                 330                 335
Ile Phe Thr Pro Ser Phe Tyr Ile Arg Ala Arg Lys Pro Ser Lys Gln
            340                 345                 350
Ala
```

<210> SEQ ID NO 5
<211> LENGTH: 353
<212> TYPE: PRT
<213> ORGANISM: Leishmania donovani

<400> SEQUENCE: 5

```
Met Ser Ala Gly Gly Arg Glu Thr Ala Pro Thr Asn Leu Ile Arg Arg
```

```
                1               5                  10                 15
Arg Asn Lys Asp Glu Thr Asn Gly Asp Val Ser Ala Ala Ala Asp Arg
                20                 25                 30

Phe Arg Asp Arg Phe Glu Lys Ala Thr Leu Glu Glu Arg Lys Ala Ala
                35                 40                 45

Thr Thr Thr Met Val Asn Glu Tyr Tyr Asp Leu Val Thr Asp Phe Tyr
            50                 55                 60

Glu Tyr Gly Trp Gly Gln Asn Phe His Phe Ala Pro Arg Tyr Ala Gly
65                  70                 75                 80

Glu Thr Phe Phe Glu Ser Leu Ala Arg His Glu Tyr Phe Leu Ala Ala
                85                 90                 95

Arg Gly Gly Phe Met Glu Gly Asp His Ile Val Asp Val Gly Cys Gly
                100                105                110

Val Gly Gly Pro Ala Arg Asn Met Val Arg Leu Thr Arg Cys Asn Val
                115                120                125

Ile Gly Val Asn Asn Asp Tyr Gln Ile Ser Arg Ala Arg Arg His
            130                135                140

Asp Ala Leu Ala Gly Met Ser Ser Lys Ile Asp Tyr Val Lys Thr Asp
145                 150                155                160

Phe Cys Asn Met Ser Leu Ala Asp Asn Thr Phe Asp Gly Ala Tyr Ala
                165                170                175

Ile Glu Ala Thr Cys His Ala Lys Asp Lys Val Lys Cys Tyr Ser Glu
                180                185                190

Val Phe Arg Val Ile Lys Pro Gly Thr Cys Phe Val Leu Tyr Glu Trp
                195                200                205

Cys Met Thr Asp Lys Tyr Asn Pro Asn Asp Glu Tyr His Arg Thr Ile
210                 215                220

Lys His Arg Ile Glu Leu Gly Asp Gly Leu Pro Glu Met Glu Thr Cys
225                 230                235                240

Lys Gln Val Ile Glu Tyr Met Lys Gln Ala Gly Phe Val Val Glu Glu
                245                250                255

Ala Ile Asp Val Ile Ser Gln Phe Glu Ser Ser Pro Ile Lys Ser Ile
                260                265                270

Pro Trp Tyr Gln Pro Leu Val Gly Asp Tyr Ser Ser Leu Gln Gly Leu
                275                280                285

Arg Ser Thr Pro Ile Gly Arg Ile Leu Thr Asn Val Met Cys Arg Val
                290                295                300

Leu Glu Phe Val Arg Leu Ala Pro Lys Gly Thr Tyr Lys Ala Thr Glu
305                 310                315                320

Val Leu Glu Glu Ala Ala Glu Ser Leu Val Val Gly Gly Gln Leu Gly
                325                330                335

Ile Phe Thr Pro Ser Phe Tyr Ile Arg Ala Arg Lys Pro Ser Lys Gln
                340                345                350

Ala

<210> SEQ ID NO 6
<211> LENGTH: 353
<212> TYPE: PRT
<213> ORGANISM: Leishmania major

<400> SEQUENCE: 6

Met Ser Ala Gly Gly Arg Glu Thr Ala Pro Met Asn Leu Leu Arg Arg
1               5                  10                 15

Arg Asn Lys Asp Glu Ile Asn Gly Asp Val Asn Ala Ala Ala Asp Arg
                20                 25                 30
```

Phe Arg Asn Arg Phe Glu Lys Ala Thr Leu Glu Glu Arg Lys Ala Ala
            35                  40                  45

Thr Thr Thr Met Val Asn Glu Tyr Tyr Asp Leu Val Thr Asp Phe Tyr
 50                  55                  60

Glu Tyr Gly Trp Gly Gln Asn Phe His Phe Ala Pro Arg Tyr Ala Gly
 65                  70                  75                  80

Glu Thr Phe Phe Glu Ser Leu Ala Arg His Glu Tyr Phe Leu Ala Ala
                85                  90                  95

Arg Gly Gly Phe Met Glu Gly Asp His Ile Val Asp Val Gly Cys Gly
               100                 105                 110

Val Gly Gly Pro Ala Arg Asn Ile Val Arg Leu Thr Arg Cys Asn Val
               115                 120                 125

Thr Gly Val Asn Asn Asn Asp Tyr Gln Ile Ser Arg Ala Arg Arg His
130                 135                 140

Asp Ala Leu Ala Gly Met Ser Cys Lys Ile Asp Tyr Val Lys Thr Asp
145                 150                 155                 160

Phe Cys Asn Met Ser Leu Ala Asp Asn Thr Phe Asp Gly Ala Tyr Ala
                165                 170                 175

Ile Glu Ala Thr Cys His Ala Lys Asp Lys Val Lys Cys Tyr Ser Glu
                180                 185                 190

Val Phe Arg Val Ile Lys Pro Gly Thr Cys Phe Val Leu Tyr Glu Trp
                195                 200                 205

Cys Met Thr Asp Lys Tyr Asn Pro Asn Asp Glu Tyr His Arg Thr Ile
210                 215                 220

Lys His Arg Ile Glu Leu Gly Asp Gly Leu Pro Glu Met Glu Thr Cys
225                 230                 235                 240

Lys Gln Val Ile Glu Tyr Met Lys Glu Ala Gly Phe Val Val Glu Glu
                245                 250                 255

Ala Ile Asp Val Ile Ser Gln Phe Glu Ser Ser Pro Ile Lys Ser Ile
                260                 265                 270

Pro Trp Tyr Gln Pro Leu Val Gly Asp Tyr Ser Ser Leu Gln Gly Leu
                275                 280                 285

Arg Ser Thr Pro Ile Gly Arg Ile Leu Thr Asn Ile Met Cys Arg Val
290                 295                 300

Leu Glu Phe Val His Leu Ala Pro Lys Gly Thr Tyr Lys Ala Thr Glu
305                 310                 315                 320

Val Leu Glu Glu Ala Ala Glu Ser Leu Val Val Gly Gln Leu Gly
                325                 330                 335

Ile Phe Thr Pro Ser Phe Tyr Ile Arg Ala Arg Lys Pro Ser Lys Gln
                340                 345                 350

Ala

<210> SEQ ID NO 7
<211> LENGTH: 236
<212> TYPE: PRT
<213> ORGANISM: Leishmania infantum

<400> SEQUENCE: 7

Met Lys Ile Arg Ser Val Arg Pro Leu Val Leu Leu Val Cys Val
 1               5                  10                  15

Ala Ala Val Leu Ala Leu Ser Ala Ser Ala Glu Pro His Lys Ala Ala
                20                  25                  30

Val Asp Val Gly Pro Leu Ser Val Gly Pro Gln Ser Val Gly Pro Leu
                35                  40                  45

-continued

Ser Val Gly Pro Gln Ala Val Gly Pro Leu Ser Val Gly Pro Gln Ser
    50                  55                  60

Val Gly Pro Leu Ser Val Gly Pro Gln Ala Val Gly Pro Leu Ser Val
65                  70                  75                  80

Gly Pro Gln Ser Val Gly Pro Leu Ser Val Gly Pro Leu Ser Val Gly
                    85                  90                  95

Pro Gln Ser Val Gly Pro Leu Ser Val Gly Ser Gln Ser Val Gly Pro
            100                 105                 110

Leu Ser Val Gly Pro Gln Ser Val Gly Pro Leu Ser Val Gly Pro Gln
        115                 120                 125

Ala Val Gly Pro Leu Ser Val Gly Pro Gln Ser Val Gly Pro Leu Ser
    130                 135                 140

Val Gly Pro Gln Ala Val Gly Pro Leu Ser Val Gly Pro Gln Ser Val
145                 150                 155                 160

Gly Pro Leu Ser Val Gly Pro Gln Ser Val Gly Pro Leu Ser Val Gly
                    165                 170                 175

Ser Gln Ser Val Gly Pro Leu Ser Val Gly Pro Gln Ser Val Gly Pro
            180                 185                 190

Leu Ser Val Gly Pro Gln Ser Val Gly Pro Leu Ser Val Gly Pro Gln
        195                 200                 205

Ser Val Gly Pro Leu Ser Val Gly Pro Gln Ser Val Gly Pro Leu Ser
    210                 215                 220

Val Gly Pro Gln Ser Val Asp Val Ser Pro Val Ser
225                 230                 235

<210> SEQ ID NO 8
<211> LENGTH: 443
<212> TYPE: PRT
<213> ORGANISM: Leishmania infantum

<400> SEQUENCE: 8

Met Ala Thr Ser Arg Ala Ala Leu Cys Ala Val Ala Val Cys Val
1               5                   10                  15

Val Leu Ala Ala Ala Cys Ala Pro Ala Arg Ala Ile Tyr Val Gly Thr
            20                  25                  30

Pro Ala Ala Ala Leu Phe Glu Glu Phe Lys Arg Thr Tyr Arg Arg Ala
        35                  40                  45

Tyr Gly Thr Leu Ala Glu Glu Gln Gln Arg Leu Ala Asn Phe Glu Arg
    50                  55                  60

Asn Leu Glu Leu Met Arg Glu His Gln Ala Arg Asn Pro His Ala Arg
65                  70                  75                  80

Phe Gly Ile Thr Lys Phe Phe Asp Leu Ser Glu Ala Glu Phe Ala Ala
                    85                  90                  95

Arg Tyr Leu Asn Gly Ala Ala Tyr Phe Ala Ala Lys Gln His Ala
            100                 105                 110

Gly Gln His Tyr Arg Lys Ala Arg Ala Asp Leu Ser Ala Val Pro Asp
        115                 120                 125

Ala Val Asp Trp Arg Glu Lys Gly Ala Val Thr Pro Val Lys Asn Gln
    130                 135                 140

Gly Ala Cys Gly Ser Cys Trp Ala Phe Ser Ala Val Gly Asn Ile Glu
145                 150                 155                 160

Ser Gln Trp Ala Arg Ala Gly His Gly Leu Val Ser Leu Ser Glu Gln
                    165                 170                 175

Gln Leu Val Ser Cys Asp Asp Lys Asp Asn Gly Cys Asn Gly Gly Leu
            180                 185                 190

```
Met Leu Gln Ala Phe Glu Trp Leu Leu Arg His Met Tyr Gly Ile Val
        195                 200                 205

Phe Thr Glu Lys Ser Tyr Pro Tyr Thr Ser Gly Asn Gly Asp Val Ala
        210                 215                 220

Glu Cys Leu Asn Ser Ser Lys Leu Val Pro Gly Ala Gln Ile Asp Gly
225                 230                 235                 240

Tyr Val Met Ile Pro Ser Asn Glu Thr Val Met Ala Ala Trp Leu Ala
                245                 250                 255

Glu Asn Gly Pro Ile Ala Ile Ala Val Asp Ala Ser Ser Phe Met Ser
                260                 265                 270

Tyr Gln Ser Gly Val Leu Thr Ser Cys Ala Gly Asp Ala Leu Asn His
        275                 280                 285

Gly Val Leu Leu Val Gly Tyr Asn Lys Thr Gly Val Pro Tyr Trp
        290                 295                 300

Val Ile Lys Asn Ser Trp Gly Glu Asp Trp Gly Glu Lys Gly Tyr Val
305                 310                 315                 320

Arg Val Val Met Gly Leu Asn Ala Cys Leu Leu Ser Glu Tyr Pro Val
                325                 330                 335

Ser Ala His Val Pro Arg Ser Leu Thr Pro Gly Pro Gly Thr Glu Ser
                340                 345                 350

Glu Glu Arg Ala Pro Lys Arg Val Thr Val Glu Gln Met Met Cys Thr
        355                 360                 365

Asp Met Tyr Cys Arg Glu Gly Cys Lys Lys Ser Leu Leu Thr Ala Asn
        370                 375                 380

Val Cys Tyr Lys Asn Gly Gly Gly Ser Ser Met Thr Lys Cys Gly
385                 390                 395                 400

Pro Gln Lys Val Leu Met Cys Ser Tyr Ser Asn Pro His Cys Phe Gly
                405                 410                 415

Pro Gly Leu Cys Leu Glu Thr Pro Asp Gly Lys Cys Ala Pro Tyr Phe
                420                 425                 430

Leu Gly Ser Ile Met Asn Thr Cys Gln Tyr Thr
        435                 440

<210> SEQ ID NO 9
<211> LENGTH: 443
<212> TYPE: PRT
<213> ORGANISM: Leishmania donovani

<400> SEQUENCE: 9

Met Ala Thr Ser Arg Ala Ala Leu Cys Ala Val Ala Val Val Cys Val
1               5                   10                  15

Val Leu Ala Ala Ala Cys Ala Pro Ala Arg Ala Ile Tyr Val Gly Thr
                20                  25                  30

Pro Ala Ala Ala Leu Phe Glu Glu Phe Lys Arg Thr Tyr Arg Arg Ala
        35                  40                  45

Tyr Gly Thr Leu Ala Glu Glu Gln Gln Arg Leu Ala Asn Phe Glu Arg
        50                  55                  60

Asn Leu Glu Leu Met Arg Glu His Gln Ala Arg Asn Pro His Ala Arg
65                  70                  75                  80

Phe Gly Ile Thr Lys Phe Phe Asp Leu Ser Glu Ala Glu Phe Ala Ala
                85                  90                  95

Arg Tyr Leu Asn Gly Ala Ala Tyr Phe Ala Ala Ala Lys Gln His Ala
                100                 105                 110

Gly Gln His Tyr Arg Lys Ala Arg Ala Asp Leu Ser Ala Val Pro Asp
        115                 120                 125
```

```
Ala Val Asp Trp Arg Glu Lys Gly Ala Val Thr Pro Val Lys Asn Gln
        130                 135                 140

Gly Ala Cys Gly Ser Cys Trp Ala Phe Ser Ala Val Gly Asn Ile Glu
145                 150                 155                 160

Ser Gln Trp Ala Arg Val Gly His Gly Leu Val Ser Leu Ser Glu Gln
                165                 170                 175

Gln Leu Val Ser Cys Asp Asp Lys Asp Asn Gly Cys Asn Gly Gly Leu
            180                 185                 190

Met Leu Gln Ala Phe Glu Trp Leu Arg His Met Tyr Gly Ile Val
        195                 200                 205

Phe Thr Glu Lys Ser Tyr Pro Tyr Thr Ser Gly Asn Gly Asp Val Ala
210                 215                 220

Glu Cys Leu Asn Ser Ser Lys Leu Val Pro Gly Ala Gln Ile Asp Gly
225                 230                 235                 240

Tyr Val Met Ile Pro Ser Asn Glu Thr Val Met Ala Ala Trp Leu Ala
                245                 250                 255

Glu Asn Gly Pro Ile Ala Ile Ala Val Asp Ala Ser Ser Phe Met Ser
            260                 265                 270

Tyr Gln Ser Gly Val Leu Thr Ser Cys Ala Gly Asp Ala Leu Asn His
        275                 280                 285

Gly Val Leu Leu Val Gly Tyr Asn Lys Thr Gly Gly Val Pro Tyr Trp
290                 295                 300

Val Ile Lys Asn Ser Trp Gly Glu Asp Trp Gly Glu Lys Gly Tyr Val
305                 310                 315                 320

Arg Val Ala Met Gly Lys Asn Ala Cys Leu Leu Ser Glu Tyr Pro Val
                325                 330                 335

Ser Ala His Val Pro Arg Ser Leu Thr Pro Gly Pro Gly Thr Glu Ser
            340                 345                 350

Glu Glu Arg Ala Pro Lys Arg Val Thr Val Glu Gln Val Met Cys Thr
        355                 360                 365

Asp Met Tyr Cys Arg Glu Gly Cys Lys Lys Ser Leu Leu Thr Ala Asn
370                 375                 380

Val Cys Tyr Lys Asn Gly Gly Gly Ser Ser Met Thr Lys Cys Gly
385                 390                 395                 400

Pro Lys Lys Val Leu Met Cys Ser Tyr Ser Asn Pro His Cys Phe Gly
                405                 410                 415

Pro Gly Leu Cys Leu Glu Thr Pro Asp Gly Lys Cys Ala Pro Tyr Phe
            420                 425                 430

Leu Gly Ser Ile Met Asn Thr Cys Gln Tyr Thr
        435                 440

<210> SEQ ID NO 10
<211> LENGTH: 443
<212> TYPE: PRT
<213> ORGANISM: Leishmania major

<400> SEQUENCE: 10

Met Ala Thr Ser Arg Ala Ala Leu Cys Ala Val Ala Val Cys Val
1               5                   10                  15

Val Leu Ala Ala Ala Cys Ala Pro Ala Arg Ala Ile Tyr Val Gly Thr
                20                  25                  30

Pro Ala Ala Ala Leu Phe Glu Glu Phe Lys Arg Thr Tyr Gln Arg Ala
            35                  40                  45

Tyr Gly Thr Leu Thr Glu Glu Gln Gln Arg Leu Ala Asn Phe Glu Arg
        50                  55                  60
```

```
Asn Leu Glu Leu Met Arg Glu His Gln Ala Arg Asn Pro His Ala Arg
 65                  70                  75                  80

Phe Gly Ile Thr Lys Phe Phe Asp Leu Ser Glu Ala Glu Phe Ala Ala
                 85                  90                  95

Arg Tyr Leu Asn Gly Ala Ala Tyr Phe Ala Ala Lys Gln His Ala
            100                 105                 110

Gly Gln His Tyr Arg Lys Ala Arg Ala Asp Leu Ser Ala Val Pro Asp
        115                 120                 125

Ala Val Asp Trp Arg Glu Lys Gly Ala Val Thr Pro Val Lys Asn Gln
130                 135                 140

Gly Ala Cys Gly Ser Cys Trp Ala Phe Ser Ala Val Gly Asn Ile Glu
145                 150                 155                 160

Ser Gln Trp Ala Val Ala Gly His Lys Leu Val Arg Leu Ser Glu Gln
                165                 170                 175

Gln Leu Val Ser Cys Asp His Val Asp Asn Gly Cys Gly Gly Gly Leu
            180                 185                 190

Met Leu Gln Ala Phe Glu Trp Val Leu Arg Asn Met Asn Gly Thr Val
        195                 200                 205

Phe Thr Glu Lys Ser Tyr Pro Tyr Val Ser Gly Asn Gly Asp Val Pro
210                 215                 220

Glu Cys Ser Asn Ser Ser Glu Leu Ala Pro Gly Ala Arg Ile Asp Gly
225                 230                 235                 240

Tyr Val Ser Met Glu Ser Ser Glu Arg Val Met Ala Ala Trp Leu Ala
                245                 250                 255

Lys Asn Gly Pro Ile Ser Ile Ala Val Asp Ala Ser Ser Phe Met Ser
            260                 265                 270

Tyr His Ser Gly Val Leu Thr Ser Cys Ile Gly Glu Gln Leu Asn His
        275                 280                 285

Gly Val Leu Leu Val Gly Tyr Asn Met Thr Gly Glu Val Pro Tyr Trp
290                 295                 300

Val Ile Lys Asn Ser Trp Gly Glu Asp Trp Gly Glu Lys Gly Tyr Val
305                 310                 315                 320

Arg Val Thr Met Gly Val Asn Ala Cys Leu Leu Thr Gly Tyr Pro Val
                325                 330                 335

Ser Val His Val Ser Gln Ser Pro Thr Pro Gly Pro Asn Thr Thr Thr
            340                 345                 350

Thr Thr His Ala Pro Lys Arg Val Thr Val Lys Gln Ile Thr Cys Thr
        355                 360                 365

Asp Tyr Phe Cys Arg Lys Gly Cys Lys Thr Thr Val Ile Pro Thr Lys
370                 375                 380

Glu Cys Leu Pro Asn Gly Ala Gly Gly Ser Phe Gln Met Glu Cys Gly
385                 390                 395                 400

Asp His Gln Val Leu Lys Leu Thr Tyr Thr Ser Met Asn Cys Thr Gly
                405                 410                 415

Glu Ala Lys Tyr Thr Val Thr Arg Glu Gly Lys Cys Gly Ile Ser Trp
            420                 425                 430

Ser Gly Ser Ser Lys Ser Ile Cys Gln Tyr Val
        435                 440

<210> SEQ ID NO 11
<211> LENGTH: 279
<212> TYPE: DNA
<213> ORGANISM: Leishmania infantum

<400> SEQUENCE: 11
```

-continued

```
atggccacca cgtacgagga gttttcggcg aagctggacc gcctggatga ggagttcaac      60
aggaagatgc aggagcagaa cgccaagttc tttgcggaca agccggatga gtcgacgctg     120
tcgcccgaga tgaaggagca ctacgagaag ttcgagcgca tgatcaagga acacacagag     180
aagttcaaca agaagatgca cgagcactcg gagcacttca agcagaagtt cgccgagctg     240
ctcgagcagc agaaggctgc gcagtacccg tccaagtaa                           279
```

<210> SEQ ID NO 12
<211> LENGTH: 279
<212> TYPE: DNA
<213> ORGANISM: Leishmania donovani

<400> SEQUENCE: 12

```
atggccacca cgtacgagga gttttcggcg aagctggacc gcctggatca ggagttcaac      60
aggaagatgc aggagcagaa cgccaagttc tttgcggaca agccggatga gtcgacgctg     120
tcgcccgaga tgagagagca ctacgagaag ttcgagcgca tgatcaagga acacacagag     180
aagttcaaca agaagatgca cgagcactcg gagcacttca agcagaagtt cgccgagctg     240
ctcgagcagc agaaggctgc gcagtacccg tccaagtaa                           279
```

<210> SEQ ID NO 13
<211> LENGTH: 279
<212> TYPE: DNA
<213> ORGANISM: Leishmania major

<400> SEQUENCE: 13

```
atggccacca cgtacgagga gttctcggcg aagctggacc gcctggatga ggagttcaac      60
aggaagatgc aggaacagaa cgccaagttc tttgcggaca agccggatga gtcgacgctg     120
tcgcccgaga tgaaggagca ctacgagaag ttcgagcgca tgatcaagga gcacacagag     180
aagttcaaca agaagatgca cgagcactcg gagcacttca agcagaagtt cgccgagctg     240
ctcgagcagc agaaggctgc gcagtacccg tccaagtga                           279
```

<210> SEQ ID NO 14
<211> LENGTH: 1062
<212> TYPE: DNA
<213> ORGANISM: Leishmania infantum

<400> SEQUENCE: 14

```
atgtccgccg gtggccgtga gaccgcgccg acgaacctga ttcgtcgccg caacaaggac      60
gagacaaacg gggatgtcag cgccgccgcc gaccgcttcc gcgaccgctt cgagaaggca     120
accctcgagg agcgcaaggc cgccaccacg acgatggtca acgagtacta cgacctggtg     180
acggacttct acgagtacgg ctggggccag aacttccatt tcgcgccgcg ctacgccggc     240
gagaccttct tcgagtccct cgcgcgccac gagtacttcc tggccgctcg cggcggcttc     300
atggagggcg accacatcgt cgacgtgggc tgcggcgtcg gcggtccggc gcgcaacatg     360
gttcgcctca cgcgctgcaa cgtcatcggc gtcaacaaca acgattacca gatcagccgc     420
gctcgccgtc atgacgcgct cgccggtatg agctccaaga tcgactacgt caagaccgac     480
ttctgcaaca tgagcttagc cgacaacacc ttcgacggcg cctacgccat cgaggccacc     540
tgccacgcaa aggacaaggt caagtgctat agcgaggtct tccgtgtcat caagcccggc     600
acctgctttg tcctgtacga gtggtgcatg accgacaagt acaaccccaa tgacgagtac     660
caccgcacaa tcaagcaccg catcgagctg ggcgacggcc tgccggagat ggagacgtgc     720
aaacaggtga tcgagtacat gaagcaggcc ggcttcgtgg tggaggaggc catagacgtc     780
```

| | |
|---|---|
| atcagtcagt tcgagtccag ccccatcaag agtatcccgt ggtaccagcc gctggtcggc | 840 |
| gactattcgt ccctgcaggg cctgcgctct accccgattg ccgcatcct cacgaacgtc | 900 |
| atgtgtcgcg tgctggagtt cgtgcgccta gctccgaagg gcacgtacaa ggcgacggag | 960 |
| attttggagg aggctgcgga aagcctggtg gtgggcggtc agctcggcat cttcacgccg | 1020 |
| tccttctaca tccgcgctcg caagccgtcc aagcaggctt ag | 1062 |

<210> SEQ ID NO 15
<211> LENGTH: 1062
<212> TYPE: DNA
<213> ORGANISM: Leishmania donovani

<400> SEQUENCE: 15

| | |
|---|---|
| atgtccgccg gtggccgtga gaccgcgccg acgaacctga ttcgtcgccg caacaaggac | 60 |
| gagacaaacg gggatgtcag cgccgccgcc gaccgcttcc gcgaccgctt cgagaaggca | 120 |
| accctcgagg agcgcaaggc cgccaccacg acgatggtca acgagtacta cgacctggtg | 180 |
| acggacttct acgagtacgg ctggggccag aacttccatt tcgcgccgcg ctacgccggc | 240 |
| gagaccttct tcgagtccct cgcgcgccac gagtacttcc tggccgctcg cggcggcttc | 300 |
| atggagggcg accacatcgt cgacgtgggc tgcggcgtcg gcggtccggc gcgcaacatg | 360 |
| gttcgcctca cgcgctgcaa cgtcatcggc gtcaacaaca acgattacca gatcagccgc | 420 |
| gctcgccgtc atgacgcgct cgccggtatg agctccaaga tcgactacgt caagaccgac | 480 |
| ttctgcaaca tgagcttagc cgacaacacc ttcgacggcg cctacgccat cgaggccacc | 540 |
| tgccacgcaa aggacaaggt caagtgctat agcgaggtct tccgtgtcat caagcccggc | 600 |
| acctgctttg tcctgtacga gtggtgcatg accgacaagt acaacccccaa tgacgagtac | 660 |
| caccgcacaa tcaagcaccg catcgagctg ggcgacggcc tgccggagat ggagacgtgc | 720 |
| aaacaggtga tcgagtacat gaagcaggcc ggcttcgtgg tggaggaggc catagacgtc | 780 |
| atcagtcagt tcgaatccag ccccatcaag agtatcccgt ggtaccagcc gctggtcggc | 840 |
| gactattcgt ccctgcaggg cctgcgctct accccgattg ccgcatcct cacgaacgtc | 900 |
| atgtgtcgcg tgctggagtt cgtgcgccta gctccgaagg gcacgtacaa ggcgacggag | 960 |
| gttttggagg aggctgcgga aagcctggtg gtgggcggtc agctcggcat cttcacgccg | 1020 |
| tccttctaca tccgcgctcg caagccgtcc aagcaggctt ag | 1062 |

<210> SEQ ID NO 16
<211> LENGTH: 1062
<212> TYPE: DNA
<213> ORGANISM: Leishmania major

<400> SEQUENCE: 16

| | |
|---|---|
| atgtctgccg gtggccgtga gaccgcgccg atgaacctgc ttcgtcgccg caacaaggat | 60 |
| gagataaacg gggatgtcaa cgccgccgcc gaccgcttcc gcaaccgctt cgagaaggca | 120 |
| accctcgagg agcgcaaggc cgccaccacg acgatggtca acgagtacta cgacctggtg | 180 |
| acggacttct acgagtacgg ctggggccag aactttcatt tcgcgccgcg ctacgccggc | 240 |
| gagaccttct tcgagtccct cgcgcgccac gagtacttcc tggccgcccg cggcggcttc | 300 |
| atggagggcg accatatcgt cgacgtgggc tgcggcgtcg gcggtccggc gcgcaacata | 360 |
| gttcgcctca cgcgctgtaa cgtcaccggc gtcaacaaca acgattacca aatcagccgc | 420 |
| gctcgccgtc atgacgcact cgccggtatg agctgcaaaa tcgactacgt caagaccgac | 480 |
| ttctgcaaca tgagcttagc cgacaacacc ttcgacggcg cctacgccat cgaggccaca | 540 |

-continued

```
tgccacgcaa aggacaaggt caagtgctat agcgaggtct tccgtgtcat caagcccggc    600
acctgcttcg tcctgtacga gtggtgcatg accgacaagt acaaccccaa tgacgagtac    660
catcgcacga tcaagcaccg cattgagctg ggcgacggcc tgccggagat ggagacgtgc    720
aagcaggtga tcgagtacat gaaggaggcc ggtttcgtgg tggaggaagc catagatgtc    780
atcagtcagt tcgagtccag ccccatcaag agcatcccgt ggtaccagcc gctggttggc    840
gactactcgt ccctgcaggg cctgcgctct accccgattg gccgcatcct caccaacatc    900
atgtgtcgcg tgctggagtt cgtgcaccta gctccgaagg gcacgtacaa ggcgacggag    960
gttttggagg aggctgcgga aagcctggtg gtgggcggtc agctcggcat cttcacgccg   1020
tccttctaca tccgcgctcg caagccgtcc aagcaggcct ag                      1062
```

<210> SEQ ID NO 17
<211> LENGTH: 711
<212> TYPE: DNA
<213> ORGANISM: Leishmania infantum

<400> SEQUENCE: 17

```
atgaagatcc gcagcgtgcg tccgcttgtg gtgttgctgg tgtgcgtcgc ggcggtgctc     60
gcactcagcg cctccgctga gccgcacaag gcggccgttg acgtcggccc gctctccgtt    120
ggcccgcagt ccgtcggccc gctctctgtt ggcccgcagg ctgttggccc gctctccgtt    180
ggcccgcagt ccgtcggccc gctctctgtt ggcccgcagg ctgttggccc gctctctgtt    240
ggcccgcagt ccgttggccc gctctccgtt ggcccgctct ccgttggccc gcagtctgtt    300
ggcccgctct ccgttggctc gcagtccgtc ggcccgctct ctgttggtcc gcagtccgtc    360
ggcccgctct ccgttggccc gcaggctgtt ggcccgctct ccgttggccc gcagtccgtc    420
ggcccgctct ctgttggccc gcaggctgtt ggcccgctct ctgttggccc gcagtccgtt    480
ggcccgctct ccgttggccc gcagtctgtt ggcccgctct ccgttggctc gcagtccgtc    540
ggcccgctct ctgttggtcc gcagtccgtc ggcccgctct ccgttggccc gcagtctgtc    600
ggcccgctct ccgttggccc gcagtccgtc ggcccgctct ccgttggtcc gcagtccgtt    660
ggcccgctct ccgttggccc gcagtccgtt gacgtttctc cggtgtctta a             711
```

<210> SEQ ID NO 18
<211> LENGTH: 1332
<212> TYPE: DNA
<213> ORGANISM: Leishmania infantum

<400> SEQUENCE: 18

```
atggcgacgt cgagggccgc tctctgcgct gttgcggtcg tgtgcgtggt gcttgcggct     60
gcctgcgcgc ctgcgcgcgc gatatacgtg ggcacgccgg ctgctgcgct gttcgaggag    120
ttcaagcgga cgtaccggcg cgcgtacggg acgctggccg aggagcagca gcggctggcg    180
aacttcgagc gcaacctgga gctgatgcgc gagcatcagg cgaggaaccc acacgcgagg    240
ttcgggatca cgaagttctt cgacctgtcg gaggcggagt tcgccgcgcg ctacctgaac    300
ggcgccgcgt acttcgcagc ggcgaagcag cacgccggcc agcactaccg caaggcgcgc    360
gcggacctgt cggcggtgcc tgatgcggtg gactggcgcg agaagggcgc cgtgacgccg    420
gtgaagaatc aaggcgcgtg cgggtcgtgc tgggcgttct cggcggtcgg caacatcgag    480
tcgcagtggg cccgtgccgg ccacggcttg gtgagcctgt cggagcagca gctggtgagc    540
tgcgatgaca aagacaatgg ctgcaacggc gggctgatgc tgcaggcgtt cgagtggctg    600
ctgcgacaca tgtacgggat cgtgttcacg gagaagagct accccctacac gtccggcaac    660
```

```
ggtgatgtgg ccgagtgctt gaacagcagt aaactcgttc ccggcgcgca aatcgacggc    720
tacgtgatga tcccgagcaa cgaaacggtt atggctgcgt ggcttgcgga gaatggcccc    780
atcgcgattg cggtcgacgc cagctccttc atgtcttacc agagcggcgt gctgaccagc    840
tgcgctggcg atgcactgaa ccacggcgtg ctgctcgtcg ggtacaacaa gaccggtggg    900
gttccgtact gggtgatcaa gaactcgtgg ggtgaggact ggggcgagaa gggctacgtg    960
cgcgtggtca tggggctgaa cgcgtgcctg ctcagtgaat accccgtgtc cgcgcatgtg   1020
ccgcggagtc tcacccctgg cccgggcacg gagagcgagg agcgcgcccc taaacgggtg   1080
acggtggagc agatgatgtg caccgatatg tactgcaggg aggggtgcaa gaagagtctt   1140
ctcaccgcga acgtgtgcta caagaacggg ggaggcggct cctctatgac gaagtgcggt   1200
ccgcagaagg tgctgatgtg ctcgtactcg aaccctcatt gctttggtcc tgggctgtgc   1260
ctcgagactc ctgatggcaa gtgcgcgccg tacttcttgg gctcgatcat gaacacctgc   1320
cagtacacgt ag                                                       1332

<210> SEQ ID NO 19
<211> LENGTH: 1332
<212> TYPE: DNA
<213> ORGANISM: Leishmania donovani

<400> SEQUENCE: 19
atggcgacgt cgagggccgc tctctgcgct gttgcggtcg tgtgcgtggt gcttgcggct     60
gcctgcgcgc ctgcgcgcgc gatatacgtg ggcacgccgg ctgctgcgct gttcgaggag    120
ttcaagcgga cgtaccggcg cgcgtacggg acgctggccg aggagcagca gcggctggcg    180
aacttcgagc gcaacctgga gctgatgcgc gagcatcagg cgaggaaccc acacgcgagg    240
ttcgggatca cgaagttctt cgacctgtcg gaggcggagt tcgccgcgcg ctacctgaac    300
ggcgccgcgt acttcgcagc ggcgaagcag cacgccggcc agcactaccg caaggcgcgc    360
gcggacctgt cggcggtgcc tgatgcgtg gactggcgcg agaagggcgc cgtgacgccg    420
gtgaagaatc aaggcgcgtg cgggtcgtgc tgggcgttct cggcggtcgg caacatcgag    480
tcgcagtggg cccgtgtcgg ccacggcttg gtgagcctgt cggagcagca gctggtgagc    540
tgcgatgaca agacaatgg ctgcaacggc gggctgatgc tgcaggcgtt cgagtggctg    600
ctgcgacaca tgtacgggat cgtgttcacg gagaagagct cccctacac gtccggcaac    660
ggtgatgtgg ccgagtgctt gaacagcagt aaactcgttc ccggcgcgca aatcgacggc    720
tacgtgatga tcccgagcaa cgaaacagtt atggctgcgt ggcttgcgga gaatggcccc    780
atcgcgattg cggtcgacgc cagctccttc atgtcttacc agagcggcgt gctgaccagc    840
tgcgctggcg atgcactgaa ccacggcgtg ctgctcgtcg ggtacaacaa gaccggtggg    900
gttccgtact gggtgatcaa gaactcgtgg ggtgaggact ggggcgagaa gggctacgtg    960
cgcgtggcca tggggaagaa cgcgtgcctg ctcagtgaat accccgtgtc cgcgcatgtg   1020
ccgcggagtc tcacccctgg cccgggcacg gagagcgagg agcgcgctcc taaacgggtg   1080
acggtggagc aggtgatgtg caccgatatg tactgcaggg aggggtgcaa gaagagtctt   1140
ctcaccgcga acgtgtgcta caagaacggg ggaggcggct cctctatgac gaagtgcggt   1200
ccgaagaagg tgctgatgtg ctcgtactcg aaccctcatt gctttggtcc tgggctgtgc   1260
ctcgagactc ctgatggcaa gtgcgcgccg tacttcttgg gctcgatcat gaacacctgc   1320
cagtacacgt ag                                                       1332

<210> SEQ ID NO 20
```

<211> LENGTH: 1332
<212> TYPE: DNA
<213> ORGANISM: Leishmania major

<400> SEQUENCE: 20

```
atggcgacgt cgagggccgc tctctgcgct gttgcggttg tgtgcgtggt gcttgcggct      60
gcctgcgcgc ccgcgcgcgc gatatacgtg ggcacgccgg ctgctgcgct gttcgaggag     120
ttcaagcgga cgtaccagcg cgcgtacggg acgctgaccg aggagcagca gcggctggcg     180
aacttcgagc gcaacctgga gctgatgcgc gagcatcagg cgaggaaccc acacgcgagg     240
ttcgggatca cgaagttctt tgacctgtcg gaggcggagt cgccgcgcg ctacctgaac      300
ggcgccgcgt acttcgcagc ggcgaagcag cacgccggcc agcactaccg caaggcgcgc     360
gcggacctgt cggcggtgcc tgatgcggtg gactggcgcg agaagggcgc cgtgacgccg     420
gtgaagaatc agggtgcgtg cgggtcgtgc tgggcgttct cggcggtcgg caacatcgag     480
tcgcagtggg ccgttgccgg ccacaagctg gtgaggctgt cggagcagca gctggtgagc     540
tgcgatcacg tggacaatgg ttgcggcggc gggctgatgc tgcaggcatt cgagtgggtg     600
ctgcgaaaca tgaacgggac cgtgttcacg gagaagagct accctacgt ctccggcaac      660
ggtgatgtgc ccgagtgctc gaacagcagt gaactcgctc ccggtgcgcg aatcgacggg     720
tacgtgtcga tggaaagcag cgaaagagtt atggctgcgt ggcttgcgaa gaatggcccc     780
atctcgattg cggtcgacgc cagctccttt atgtcttacc atagcggcgt cctgaccagc     840
tgcattggtg agcagctgaa ccacggcgtg ctgctcgttg gtacaacat gactggtgag      900
gttccgtact gggtgatcaa gaactcgtgg ggtgaggact ggggcgagaa gggctacgtg     960
cgcgtgacca tggggtgaa cgcgtgcctg ctcactgggt accccgtgtc cgtgcatgtg    1020
tcgcagagcc ccaccccctgg cccaaacacg accaccacga cgcacgctcc taaacgggtg    1080
acggtgaagc agatcacctg cacggattat ttctgccgaa aggggtgcaa gacgacggtg    1140
atccccacga aagagtgcct gccgaacggg gcaggcggct cttttcagat ggagtgcggt    1200
gaccatcagg tgttgaagct cacctacacc tccatgaatt gcactggtga ggccaagtat    1260
acggtgacaa gggagggtaa gtgcgggata tcgtggtccg gctcgagcaa gagcatttgc    1320
cagtacgtgt ag                                                          1332
```

<210> SEQ ID NO 21
<211> LENGTH: 660
<212> TYPE: PRT
<213> ORGANISM: Artificial Sequence
<220> FEATURE:
<223> OTHER INFORMATION: Amino acid sequence for a KSA fusion polypeptide.

<400> SEQUENCE: 21

```
Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
             20                  25                  30

Asp Lys Pro Asp Glu Ser Thr Leu Ser Pro Glu Met Lys Glu His Tyr
         35                  40                  45

Glu Lys Phe Glu Arg Met Ile Lys Glu His Thr Glu Lys Phe Asn Lys
     50                  55                  60

Lys Met His Glu His Ser Glu His Phe Lys Gln Lys Phe Ala Glu Leu
 65                  70                  75                  80

Leu Glu Gln Gln Lys Ala Ala Gln Tyr Pro Ser Lys Thr Ser Ser Ala
                 85                  90                  95
```

```
Gly Gly Arg Glu Thr Ala Pro Thr Asn Leu Ile Arg Arg Arg Asn Lys
            100                 105                 110

Asp Glu Thr Asn Gly Asp Val Ser Ala Ala Ala Asp Arg Phe Arg Asp
            115                 120                 125

Arg Phe Glu Lys Ala Thr Leu Glu Glu Arg Lys Ala Ala Thr Thr Thr
130                 135                 140

Met Val Asn Glu Tyr Tyr Asp Leu Val Thr Asp Phe Tyr Glu Tyr Gly
145                 150                 155                 160

Trp Gly Gln Asn Phe His Phe Ala Pro Arg Tyr Ala Gly Glu Thr Phe
                165                 170                 175

Phe Glu Ser Leu Ala Arg His Glu Tyr Phe Leu Ala Ala Arg Gly Gly
                180                 185                 190

Phe Met Glu Gly Asp His Ile Val Asp Val Gly Cys Gly Val Gly Gly
            195                 200                 205

Pro Ala Arg Asn Met Val Arg Leu Thr Arg Cys Asn Val Ile Gly Val
210                 215                 220

Asn Asn Asn Asp Tyr Gln Ile Ser Arg Ala Arg Arg His Asp Ala Leu
225                 230                 235                 240

Ala Gly Met Ser Ser Lys Ile Asp Tyr Val Lys Thr Asp Phe Cys Asn
                245                 250                 255

Met Ser Leu Ala Asp Asn Thr Phe Asp Gly Ala Tyr Ala Ile Glu Ala
                260                 265                 270

Thr Cys His Ala Lys Asp Lys Val Lys Cys Tyr Ser Glu Val Phe Arg
            275                 280                 285

Val Ile Lys Pro Gly Thr Cys Phe Val Leu Tyr Glu Trp Cys Met Thr
290                 295                 300

Asp Lys Tyr Asn Pro Asn Asp Glu Tyr His Arg Thr Ile Lys His Arg
305                 310                 315                 320

Ile Glu Leu Gly Asp Gly Leu Pro Glu Met Glu Thr Cys Lys Gln Val
                325                 330                 335

Ile Glu Tyr Met Lys Gln Ala Gly Phe Val Val Glu Glu Ala Ile Asp
                340                 345                 350

Val Ile Ser Gln Phe Glu Ser Ser Pro Ile Lys Ser Ile Pro Trp Tyr
            355                 360                 365

Gln Pro Leu Val Gly Asp Tyr Ser Ser Leu Gln Gly Leu Arg Ser Thr
            370                 375                 380

Pro Ile Gly Arg Ile Leu Thr Asn Val Met Cys Arg Val Leu Glu Phe
385                 390                 395                 400

Val Arg Leu Ala Pro Lys Gly Thr Tyr Lys Ala Thr Glu Ile Leu Glu
                405                 410                 415

Glu Ala Ala Glu Ser Leu Val Val Gly Gly Gln Leu Gly Ile Phe Thr
            420                 425                 430

Pro Ser Phe Tyr Ile Arg Ala Arg Lys Pro Ser Lys Gln Ala Gly Ser
            435                 440                 445

Glu Pro His Lys Ala Ala Val Asp Val Gly Pro Leu Ser Val Gly Pro
            450                 455                 460

Gln Ser Val Gly Pro Leu Ser Val Gly Pro Gln Ala Val Gly Pro Leu
465                 470                 475                 480

Ser Val Gly Pro Gln Ser Val Gly Pro Leu Ser Val Gly Pro Gln Ala
                485                 490                 495

Val Gly Pro Leu Ser Val Gly Pro Gln Ser Val Gly Pro Leu Ser Val
            500                 505                 510

Gly Pro Leu Ser Val Gly Pro Gln Ser Val Gly Pro Leu Ser Val Gly
```

```
        515                 520                 525

Ser Gln Ser Val Gly Pro Leu Ser Val Gly Pro Gln Ser Val Gly Pro
    530                 535                 540

Leu Ser Val Gly Pro Gln Ala Val Gly Pro Leu Ser Val Gly Pro Gln
545                 550                 555                 560
Ser Val Gly Pro Leu Ser Val Gly Pro Gln Ala Val Gly Pro Leu Ser
                565                 570                 575
Val Gly Pro Gln Ser Val Gly Pro Leu Ser Val Gly Pro Gln Ser Val
            580                 585                 590
Gly Pro Leu Ser Val Gly Ser Gln Ser Val Gly Pro Leu Ser Val Gly
        595                 600                 605
Pro Gln Ser Val Gly Pro Leu Ser Val Gly Pro Gln Ser Val Gly Pro
    610                 615                 620
Leu Ser Val Gly Pro Gln Ser Val Gly Pro Leu Ser Val Gly Pro Gln
625                 630                 635                 640
Ser Val Gly Pro Leu Ser Val Gly Pro Gln Ser Val Asp Val Ser Pro
                645                 650                 655

Val Ser Gly Ser
            660
```

<210> SEQ ID NO 22
<211> LENGTH: 1989
<212> TYPE: DNA
<213> ORGANISM: Artificial Sequence
<220> FEATURE:
<223> OTHER INFORMATION: Nucleic acid sequence encoding the KSA fusion polypeptide.

<400> SEQUENCE: 22

```
atggccacca cgtacgagga gttttcggcg aagctggacc gcctggatga ggagttcaac      60
aggaagatgc aggagcagaa cgccaagttc tttgcggaca agccggatga gtcgacgctg     120
tcgcccgaga tgaaggagca ctacgagaag ttcgagcgca tgatcaagga acacacagag     180
aagttcaaca agaagatgca cgagcactcg gagcacttca agcagaagtt cgccgagctg     240
ctcgagcagc agaaggctgc gcagtacccg tccaagacta gttccgccgg tggccgtgag     300
accgcgccga cgaacctgat tcgtcgccgc aacaaggacg agacaaacgg ggatgtcagc     360
gccgccgccg accgcttccg cgaccgcttc gagaaggcaa ccctcgagga gcgcaaggcc     420
gccaccacga cgatggtcaa cgagtactac gacctggtga cggacttcta cgagtacggc     480
tggggccaga acttccattt cgcgccgcgc tacgccggcg agaccttctt cgagtccctc     540
gcgcgccacg agtacttcct ggccgctcgc ggcggcttca tggagggcga ccacatcgtc     600
gacgtgggct gcggcgtcgg cggtccggcg cgcaacatgg ttcgcctcac gcgctgcaac     660
gtcatcggcg tcaacaacaa cgattaccag atcagccgcg ctcgccgtca tgacgcgctc     720
gccggtatga gctccaagat cgactacgtc aagaccgact tctgcaacat gagcttagcc     780
gacaacacct tcgacggcgc ctacgccatc gaggccacct gccacgcaaa ggacaaggtc     840
aagtgctata gcgaggtctt ccgtgtcatc aagcccggca cctgctttgt cctgtacgag     900
tggtgcatga ccgacaagta caaccccaat gacgagtacc accgcacaat caagcaccgc     960
atcgagctgg gcgacggcct gccggagatg gagacgtgca aacaggtgat cgagtacatg    1020
aagcaggccg gcttcgtggt ggaggaggcc atagacgtca tcagtcagtt cgagtccagc    1080
cccatcaaga gtatcccgtg gtaccagccg ctggtcggcg actattcgtc cctgcagggc    1140
ctgcgctcta ccccgattgg ccgcatcctc acgaacgtca tgtgtcgcgt gctggagttc    1200
```

-continued

```
gtgcgcctag ctccgaaggg cacgtacaag gcgacggaga ttttggagga ggctgcggaa   1260
agcctggtgg tgggcggtca gctcggcatc ttcacgccgt ccttctacat ccgcgctcgc   1320
aagccgtcca agcaggctgg atccgagccg cacaaggcgg ccgttgacgt cggcccgctc   1380
tccgttggcc cgcagtccgt cggcccgctc tctgttggcc cgcaggctgt tggcccgctc   1440
tccgttggcc cgcagtccgt cggcccgctc tctgttggcc cgcaggctgt tggcccgctc   1500
tctgttggcc cgcagtccgt tggcccgctc tccgttggcc cgctctccgt tggcccgcag   1560
tctgttggcc cgctctccgt tggctcgcag tccgtcggcc cgctctctgt tggtccgcag   1620
tccgtcggcc cgctctccgt tggcccgcag gctgttggcc cgctctccgt tggcccgcag   1680
tccgtcggcc cgctctctgt tggcccgcag gctgttggcc cgctctctgt tggcccgcag   1740
tccgttggcc cgctctccgt tggcccgcag tctgttggcc cgctctccgt tggctcgcag   1800
tccgtcggcc cgctctctgt tggtccgcag tccgtcggcc cgctctccgt tggcccgcag   1860
tctgtcggcc cgctctccgt tggcccgcag tccgtcggcc cgctctccgt tggtccgcag   1920
tccgttggcc cgctctccgt tggcccgcag tccgttgacg tttctccggt gtctggatcc   1980
gaattctaa                                                           1989
```

<210> SEQ ID NO 23
<211> LENGTH: 978
<212> TYPE: PRT
<213> ORGANISM: Artificial Sequence
<220> FEATURE:
<223> OTHER INFORMATION: Amino acid sequence for a KSAC fusion
      polypeptide.

<400> SEQUENCE: 23

```
Met Ala Thr Thr Tyr Glu Glu Phe Ser Ala Lys Leu Asp Arg Leu Asp
  1               5                  10                  15

Glu Glu Phe Asn Arg Lys Met Gln Glu Gln Asn Ala Lys Phe Phe Ala
             20                  25                  30

Asp Lys Pro Asp Glu Ser Thr Leu Ser Pro Glu Met Lys Glu His Tyr
         35                  40                  45

Glu Lys Phe Glu Arg Met Ile Lys Glu His Thr Glu Lys Phe Asn Lys
     50                  55                  60

Lys Met His Glu His Ser Glu His Phe Lys Gln Lys Phe Ala Glu Leu
 65                  70                  75                  80

Leu Glu Gln Gln Lys Ala Ala Gln Tyr Pro Ser Lys Thr Ser Ser Ala
                 85                  90                  95

Gly Gly Arg Glu Thr Ala Pro Thr Asn Leu Ile Arg Arg Asn Lys
            100                 105                 110

Asp Glu Thr Asn Gly Asp Val Ser Ala Ala Ala Asp Arg Phe Arg Asp
        115                 120                 125

Arg Phe Glu Lys Ala Thr Leu Glu Glu Arg Lys Ala Ala Thr Thr Thr
    130                 135                 140

Met Val Asn Glu Tyr Tyr Asp Leu Val Thr Asp Phe Tyr Glu Tyr Gly
145                 150                 155                 160

Trp Gly Gln Asn Phe His Phe Ala Pro Arg Tyr Ala Gly Glu Thr Phe
                165                 170                 175

Phe Glu Ser Leu Ala Arg His Glu Tyr Phe Leu Ala Ala Arg Gly Gly
            180                 185                 190

Phe Met Glu Gly Asp His Ile Val Asp Val Gly Cys Gly Val Gly Gly
        195                 200                 205

Pro Ala Arg Asn Met Val Arg Leu Thr Arg Cys Asn Val Ile Gly Val
    210                 215                 220
```

-continued

```
Asn Asn Asn Asp Tyr Gln Ile Ser Arg Ala Arg Arg His Asp Ala Leu
225                 230                 235                 240

Ala Gly Met Ser Ser Lys Ile Asp Tyr Val Lys Thr Asp Phe Cys Asn
            245                 250                 255

Met Ser Leu Ala Asp Asn Thr Phe Asp Gly Ala Tyr Ala Ile Glu Ala
                260                 265                 270

Thr Cys His Ala Lys Asp Lys Val Lys Cys Tyr Ser Glu Val Phe Arg
        275                 280                 285

Val Ile Lys Pro Gly Thr Cys Phe Val Leu Tyr Glu Trp Cys Met Thr
    290                 295                 300

Asp Lys Tyr Asn Pro Asn Asp Glu Tyr His Arg Thr Ile Lys His Arg
305                 310                 315                 320

Ile Glu Leu Gly Asp Gly Leu Pro Glu Met Glu Thr Cys Lys Gln Val
                325                 330                 335

Ile Glu Tyr Met Lys Gln Ala Gly Phe Val Val Glu Glu Ala Ile Asp
                340                 345                 350

Val Ile Ser Gln Phe Glu Ser Ser Pro Ile Lys Ser Ile Pro Trp Tyr
        355                 360                 365

Gln Pro Leu Val Gly Asp Tyr Ser Ser Leu Gln Gly Leu Arg Ser Thr
    370                 375                 380

Pro Ile Gly Arg Ile Leu Thr Asn Val Met Cys Arg Val Leu Glu Phe
385                 390                 395                 400

Val Arg Leu Ala Pro Lys Gly Thr Tyr Lys Ala Thr Glu Ile Leu Glu
                405                 410                 415

Glu Ala Ala Glu Ser Leu Val Val Gly Gly Gln Leu Gly Ile Phe Thr
                420                 425                 430

Pro Ser Phe Tyr Ile Arg Ala Arg Lys Pro Ser Lys Gln Ala Gly Ser
        435                 440                 445

Glu Pro His Lys Ala Ala Val Asp Val Gly Pro Leu Ser Val Gly Pro
    450                 455                 460

Gln Ser Val Gly Pro Leu Ser Val Gly Pro Gln Ala Val Gly Pro Leu
465                 470                 475                 480

Ser Val Gly Pro Gln Ser Val Gly Pro Leu Ser Val Gly Pro Gln Ala
                485                 490                 495

Val Gly Pro Leu Ser Val Gly Pro Gln Ser Val Gly Pro Leu Ser Val
                500                 505                 510

Gly Pro Leu Ser Val Gly Pro Gln Ser Val Gly Pro Leu Ser Val Gly
            515                 520                 525

Ser Gln Ser Val Gly Pro Leu Ser Val Gly Pro Gln Ser Val Gly Pro
        530                 535                 540

Leu Ser Val Gly Pro Gln Ala Val Gly Pro Leu Ser Val Gly Pro Gln
545                 550                 555                 560

Ser Val Gly Pro Leu Ser Val Gly Pro Gln Ala Val Gly Pro Leu Ser
                565                 570                 575

Val Gly Pro Gln Ser Val Gly Pro Leu Ser Val Gly Pro Gln Ser Val
            580                 585                 590

Gly Pro Leu Ser Val Gly Ser Gln Ser Val Gly Pro Leu Ser Val Gly
        595                 600                 605

Pro Gln Ser Val Gly Pro Leu Ser Val Gly Pro Gln Ser Val Gly Pro
    610                 615                 620

Leu Ser Val Gly Pro Gln Ser Val Gly Pro Leu Ser Val Gly Pro Gln
625                 630                 635                 640

Ser Val Gly Pro Leu Ser Val Gly Pro Gln Ser Val Asp Val Ser Pro
```

```
                645                 650                 655
Val Ser Gly Ser Glu Phe Asp Ala Val Asp Trp Arg Glu Lys Gly Ala
            660                 665                 670

Val Thr Pro Val Lys Asn Gln Gly Ala Cys Gly Ser Cys Trp Ala Phe
        675                 680                 685

Ser Ala Val Gly Asn Ile Glu Ser Gln Trp Ala Arg Ala Gly His Gly
    690                 695                 700

Leu Val Ser Leu Ser Glu Gln Gln Leu Val Ser Cys Asp Asp Lys Asp
705                 710                 715                 720

Asn Gly Cys Asn Gly Gly Leu Met Leu Gln Ala Phe Glu Trp Leu Leu
            725                 730                 735

Arg His Met Tyr Gly Ile Val Phe Thr Glu Lys Ser Tyr Pro Tyr Thr
        740                 745                 750

Ser Gly Asn Gly Asp Val Ala Glu Cys Leu Asn Ser Lys Leu Val
    755                 760                 765

Pro Gly Ala Gln Ile Asp Gly Tyr Val Met Ile Pro Ser Asn Glu Thr
    770                 775                 780

Val Met Ala Ala Trp Leu Ala Glu Asn Gly Pro Ile Ala Ile Ala Val
785                 790                 795                 800

Asp Ala Ser Ser Phe Met Ser Tyr Gln Ser Gly Val Leu Thr Ser Cys
            805                 810                 815

Ala Gly Asp Ala Leu Asn His Gly Val Leu Leu Val Gly Tyr Asn Lys
        820                 825                 830

Thr Gly Gly Val Pro Tyr Trp Val Ile Lys Asn Ser Trp Gly Glu Asp
    835                 840                 845

Trp Gly Glu Lys Gly Tyr Val Arg Val Val Met Gly Leu Asn Ala Cys
850                 855                 860

Leu Leu Ser Glu Tyr Pro Val Ser Ala His Val Pro Arg Ser Leu Thr
            865                 870                 875                 880

Pro Gly Pro Gly Thr Glu Ser Glu Glu Arg Ala Pro Lys Arg Val Thr
        885                 890                 895

Val Glu Gln Met Met Cys Thr Asp Met Tyr Cys Arg Glu Gly Cys Lys
    900                 905                 910

Lys Ser Leu Leu Thr Ala Asn Val Cys Tyr Lys Asn Gly Gly Gly Gly
        915                 920                 925

Ser Ser Met Thr Lys Cys Gly Pro Gln Lys Val Leu Met Cys Ser Tyr
    930                 935                 940

Ser Asn Pro His Cys Phe Gly Pro Gly Leu Cys Leu Glu Thr Pro Asp
945                 950                 955                 960

Gly Lys Cys Ala Pro Tyr Phe Leu Gly Ser Ile Met Asn Thr Cys Gln
            965                 970                 975

Tyr Thr

<210> SEQ ID NO 24
<211> LENGTH: 2937
<212> TYPE: DNA
<213> ORGANISM: Artificial Sequence
<220> FEATURE:
<223> OTHER INFORMATION: Nucleic acid sequence encoding the KSAC fusion
      polypeptide.

<400> SEQUENCE: 24
atggccacca cgtacgagga gttttcggcg aagctggacc gcctggatga ggagttcaac      60
aggaagatgc aggagcagaa cgccaagttc tttgcggaca gccggatga gtcgacgctg     120 tcgcccgaga tgaaggagca ctacgagaag ttcgagcgca tgatcaagga acacacagag    180
```

```
aagttcaaca agaagatgca cgagcactcg gagcacttca agcagaagtt cgccgagctg    240
ctcgagcagc agaaggctgc gcagtacccg tccaagacta gttccgccgg tggccgtgag    300
accgcgccga cgaacctgat tcgtcgccgc aacaaggacg agacaaacgg ggatgtcagc    360
gccgccgccg accgcttccg cgaccgcttc gagaaggcaa ccctcgagga gcgcaaggcc    420
gccaccacga cgatggtcaa cgagtactac gacctggtga cggacttcta cgagtacggc    480
tggggccaga acttccattt cgcgccgcgc tacgccggcg agaccttctt cgagtccctc    540
gcgcgccacg agtacttcct ggccgctcgc ggcggcttca tggagggcga ccacatcgtc    600
gacgtgggct gcggcgtcgg cggtccggcg cgcaacatgg ttcgcctcac gcgctgcaac    660
gtcatcggcg tcaacaacaa cgattaccag atcagccgcg ctcgccgtca tgacgcgctc    720
gccggtatga gctccaagat cgactacgtc aagaccgact tctgcaacat gagcttagcc    780
gacaacacct tcgacggcgc ctacgccatc gaggccacct gccacgcaaa ggacaaggtc    840
aagtgctata gcgaggtctt ccgtgtcatc aagcccggca cctgctttgt cctgtacgag    900
tggtgcatga ccgacaagta caaccccaat gacgagtacc accgcacaat caagcaccgc    960
atcgagctgg gcgacggcct gccggagatg gagacgtgca acaggtgat cgagtacatg    1020 aagcaggccg gcttcgtggt ggaggaggcc atagacgtca tcagtcagtt cgagtccagc    1080
cccatcaaga gtatcccgtg gtaccagccg ctggtcggcg actattcgtc cctgcagggc    1140
ctgcgctcta ccccgattgg ccgcatcctc acgaacgtca tgtgtcgcgt gctggagttc    1200
gtgcgcctag ctccgaaggg cacgtacaag gcgacggaga ttttggagga ggctgcggaa    1260
agcctggtgg tgggcggtca gctcggcatc ttcacgccgt ccttctacat ccgcgctcgc    1320
aagccgtcca agcaggctgg atccgagccg cacaaggcgg ccgttgacgt cggcccgctc    1380
tccgttggcc cgcagtccgt cggcccgctc tctgttggcc cgcaggctgt tggcccgctc    1440
tccgttggcc cgcagtccgt cggcccgctc tctgttggcc cgcaggctgt tggcccgctc    1500
tctgttggcc cgcagtccgt tggcccgctc tccgttggcc cgctctccgt tggcccgcag    1560
tctgttggcc cgctctccgt tggctcgcag tccgtcggcc cgctctctgt tggtccgcag    1620
tccgtcggcc cgctctccgt tggcccgcag gctgttggcc cgctctccgt tggcccgcag    1680
tccgtcggcc cgctctctgt tggcccgcag gctgttggcc cgctctctgt tggcccgcag    1740
tccgttggcc cgctctccgt tggcccgcag tctgttggcc cgctctccgt tggctcgcag    1800
tccgtcggcc cgctctctgt tggtccgcag tccgtcggcc cgctctccgt tggcccgcag    1860
tctgtcggcc cgctctccgt tggcccgcag tccgtcggcc cgctctccgt tggtccgcag    1920
tccgttggcc cgctctccgt tggcccgcag tccgttgacg tttctccggt gtctggatcc    1980
gaattcgatg cggtggactg gcgcgagaag ggcgccgtga cgccggtgaa gaatcaaggc    2040
gcgtgcgggt cgtgctgggc gttctcggcg gtcggcaaca tcgagtcgca gtgggcccgt    2100
gccggccacg gcttggtgag cctgtcggag cagcagctgg tgagctgcga tgacaaagac    2160
aatggctgca acggcgggct gatgctgcag gcgttcgagt ggctgctgcg acacatgtac    2220
gggatcgtgt tcacggagaa gagctacccc tacacgtccg gcaacggtga tgtggccgag    2280
tgcttgaaca gcagtaaaact cgttcccggc gcgcaaatcg acggctacgt gatgatcccg    2340
agcaacgaaa cggttatggc tgcgtggctt gcggagaatg gccccatcgc gattgcggtc    2400
gacgccagct ccttcatgtc ttaccagagc ggcgtgctga ccagctgcgc tggcgatgca    2460
ctgaaccacg gcgtgctgct cgtcgggtac aacaagaccg gtggggttcc gtactgggtg    2520
atcaagaact cgtgggtga ggactggggc gagaagggct acgtgcgcgt ggtcatgggg    2580
```

```
ctgaacgcgt gcctgctcag tgaataccc gtgtccgcgc atgtgccgcg gagtctcacc    2640
cctggcccgg gcacggagag cgaggagcgc gcccctaaac gggtgacggt ggagcagatg    2700
atgtgcaccg atatgtactg cagggagggg tgcaagaaga gtcttctcac cgcgaacgtg    2760
tgctacaaga acgggggagg cggctcctct atgacgaagt gcggtccgca gaaggtgctg    2820
atgtgctcgt actcgaaccc tcattgcttt ggtcctgggc tgtgcctcga gactcctgat    2880
ggcaagtgcg cgccgtactt cttgggctcg atcatgaaca cctgccagta cacgtaa      2937
```

<210> SEQ ID NO 25
<211> LENGTH: 92
<212> TYPE: PRT
<213> ORGANISM: Artificial Sequence
<220> FEATURE:
<223> OTHER INFORMATION: Amino acid sequence for an immunogenic portion of a KMP11 polypeptide.

<400> SEQUENCE: 25

```
Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
            20                  25                  30

Asp Lys Pro Asp Glu Ser Thr Leu Ser Pro Glu Met Lys Glu His Tyr
        35                  40                  45

Glu Lys Phe Glu Arg Met Ile Lys Glu His Thr Glu Lys Phe Asn Lys
    50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys
                85                  90
```

<210> SEQ ID NO 26
<211> LENGTH: 352
<212> TYPE: PRT
<213> ORGANISM: Artificial Sequence
<220> FEATURE:
<223> OTHER INFORMATION: Amino acid sequence for an immunogenic portion of a SMP polypeptide.

<400> SEQUENCE: 26

```
Ser Ala Gly Gly Arg Glu Thr Ala Pro Thr Asn Leu Ile Arg Arg Arg
 1               5                  10                  15

Asn Lys Asp Glu Thr Asn Gly Asp Val Ser Ala Ala Asp Arg Phe
            20                  25                  30

Arg Asp Arg Phe Glu Lys Ala Thr Leu Glu Glu Arg Lys Ala Ala Thr
        35                  40                  45

Thr Thr Met Val Asn Glu Tyr Tyr Asp Leu Val Thr Asp Phe Tyr Glu
    50                  55                  60

Tyr Gly Trp Gly Gln Asn Phe His Phe Ala Pro Arg Tyr Ala Gly Glu
65                  70                  75                  80

Thr Phe Phe Glu Ser Leu Ala Arg His Glu Tyr Phe Leu Ala Ala Arg
                85                  90                  95

Gly Gly Phe Met Glu Gly Asp His Ile Val Asp Val Gly Cys Gly Val
            100                 105                 110

Gly Gly Pro Ala Arg Asn Met Val Arg Leu Thr Arg Cys Asn Val Ile
        115                 120                 125

Gly Val Asn Asn Asn Asp Tyr Gln Ile Ser Arg Ala Arg Arg His Asp
    130                 135                 140
```

-continued

Ala Leu Ala Gly Met Ser Ser Lys Ile Asp Tyr Val Lys Thr Asp Phe
145                 150                 155                 160

Cys Asn Met Ser Leu Ala Asp Asn Thr Phe Asp Gly Ala Tyr Ala Ile
                165                 170                 175

Glu Ala Thr Cys His Ala Lys Asp Lys Val Lys Cys Tyr Ser Glu Val
            180                 185                 190

Phe Arg Val Ile Lys Pro Gly Thr Cys Phe Val Leu Tyr Glu Trp Cys
        195                 200                 205

Met Thr Asp Lys Tyr Asn Pro Asn Asp Glu Tyr His Arg Thr Ile Lys
210                 215                 220

His Arg Ile Glu Leu Gly Asp Gly Leu Pro Glu Met Glu Thr Cys Lys
225                 230                 235                 240

Gln Val Ile Glu Tyr Met Lys Gln Ala Gly Phe Val Val Glu Glu Ala
                245                 250                 255

Ile Asp Val Ile Ser Gln Phe Glu Ser Ser Pro Ile Lys Ser Ile Pro
            260                 265                 270

Trp Tyr Gln Pro Leu Val Gly Asp Tyr Ser Ser Leu Gln Gly Leu Arg
        275                 280                 285

Ser Thr Pro Ile Gly Arg Ile Leu Thr Asn Val Met Cys Arg Val Leu
290                 295                 300

Glu Phe Val Arg Leu Ala Pro Lys Gly Thr Tyr Lys Ala Thr Glu Ile
305                 310                 315                 320

Leu Glu Glu Ala Ala Glu Ser Leu Val Val Gly Gln Leu Gly Ile
                325                 330                 335

Phe Thr Pro Ser Phe Tyr Ile Arg Ala Arg Lys Pro Ser Lys Gln Ala
                340                 345                 350

<210> SEQ ID NO 27
<211> LENGTH: 210
<212> TYPE: PRT
<213> ORGANISM: Artificial Sequence
<220> FEATURE:
<223> OTHER INFORMATION: Amino acid sequence for an immunogenic portion
      of an A2 polypeptide.

<400> SEQUENCE: 27

Glu Pro His Lys Ala Ala Val Asp Val Gly Pro Leu Ser Val Gly Pro
1               5                   10                  15

Gln Ser Val Gly Pro Leu Ser Val Gly Pro Gln Ala Val Gly Pro Leu
                20                  25                  30

Ser Val Gly Pro Gln Ser Val Gly Pro Leu Ser Val Gly Pro Gln Ala
            35                  40                  45

Val Gly Pro Leu Ser Val Gly Pro Gln Ser Val Gly Pro Leu Ser Val
        50                  55                  60

Gly Pro Leu Ser Val Gly Pro Gln Ser Val Gly Pro Leu Ser Val Gly
65                  70                  75                  80

Ser Gln Ser Val Gly Pro Leu Ser Val Gly Pro Gln Ser Val Gly Pro
                85                  90                  95

Leu Ser Val Gly Pro Gln Ala Val Gly Pro Leu Ser Val Gly Pro Gln
            100                 105                 110

Ser Val Gly Pro Leu Ser Val Gly Pro Gln Ala Val Gly Pro Leu Ser
        115                 120                 125

Val Gly Pro Gln Ser Val Gly Pro Leu Ser Val Gly Pro Gln Ser Val
    130                 135                 140

Gly Pro Leu Ser Val Gly Ser Gln Ser Val Gly Pro Leu Ser Val Gly
145                 150                 155                 160

```
Pro Gln Ser Val Gly Pro Leu Ser Val Gly Pro Gln Ser Val Gly Pro
                165                 170                 175

Leu Ser Val Gly Pro Gln Ser Val Gly Pro Leu Ser Val Gly Pro Gln
            180                 185                 190

Ser Val Gly Pro Leu Ser Val Gly Pro Gln Ser Val Asp Val Ser Pro
            195                 200                 205

Val Ser
    210

<210> SEQ ID NO 28
<211> LENGTH: 316
<212> TYPE: PRT
<213> ORGANISM: Artificial Sequence
<220> FEATURE:
<223> OTHER INFORMATION: Amino acid sequence for an immunogenic portion
      of a CBP polypeptide.

<400> SEQUENCE: 28

Asp Ala Val Asp Trp Arg Glu Lys Gly Ala Val Thr Pro Val Lys Asn
 1               5                  10                  15

Gln Gly Ala Cys Gly Ser Cys Trp Ala Phe Ser Ala Val Gly Asn Ile
             20                  25                  30

Glu Ser Gln Trp Ala Arg Ala Gly His Gly Leu Val Ser Leu Ser Glu
         35                  40                  45

Gln Gln Leu Val Ser Cys Asp Asp Lys Asp Asn Gly Cys Asn Gly Gly
 50                  55                  60

Leu Met Leu Gln Ala Phe Glu Trp Leu Leu Arg His Met Tyr Gly Ile
 65                  70                  75                  80

Val Phe Thr Glu Lys Ser Tyr Pro Tyr Thr Ser Gly Asn Gly Asp Val
                 85                  90                  95

Ala Glu Cys Leu Asn Ser Ser Lys Leu Val Pro Gly Ala Gln Ile Asp
            100                 105                 110

Gly Tyr Val Met Ile Pro Ser Asn Glu Thr Val Met Ala Ala Trp Leu
        115                 120                 125

Ala Glu Asn Gly Pro Ile Ala Ile Ala Val Asp Ala Ser Ser Phe Met
130                 135                 140

Ser Tyr Gln Ser Gly Val Leu Thr Ser Cys Ala Gly Asp Ala Leu Asn
145                 150                 155                 160

His Gly Val Leu Leu Val Gly Tyr Asn Lys Thr Gly Val Pro Tyr Tyr
                165                 170                 175

Trp Val Ile Lys Asn Ser Trp Gly Glu Asp Trp Gly Leu Lys Gly Tyr
            180                 185                 190

Val Arg Val Val Met Gly Leu Asn Ala Cys Leu Leu Ser Glu Tyr Pro
        195                 200                 205

Val Ser Ala His Val Pro Arg Ser Leu Thr Pro Gly Pro Gly Thr Glu
210                 215                 220

Ser Glu Glu Arg Ala Pro Lys Arg Val Thr Val Glu Gln Met Met Cys
225                 230                 235                 240

Thr Asp Met Tyr Cys Arg Glu Gly Cys Lys Lys Ser Leu Leu Thr Ala
                245                 250                 255

Asn Val Cys Tyr Lys Asn Gly Gly Gly Ser Ser Met Thr Lys Cys
            260                 265                 270

Gly Pro Gln Lys Val Leu Met Cys Ser Tyr Ser Asn Pro His Cys Phe
        275                 280                 285

Gly Pro Gly Leu Cys Leu Glu Thr Pro Asp Gly Lys Cys Ala Pro Tyr
        290                 295                 300
```

```
Phe Leu Gly Ser Ile Met Asn Thr Cys Gln Tyr Thr
305                 310                 315
```

<210> SEQ ID NO 29
<211> LENGTH: 276
<212> TYPE: DNA
<213> ORGANISM: Artificial Sequence
<220> FEATURE:
<223> OTHER INFORMATION: Nucleic acid sequence encoding the KMP11
      polypeptide.

<400> SEQUENCE: 29

```
atggccacca cgtacgagga gttttcggcg aagctggacc gcctggatga ggagttcaac      60
aggaagatgc aggagcagaa cgccaagttc tttgcggaca gccggatga gtcgacgctg     120
tcgcccgaga tgaaggagca ctacgagaag ttcgagcgca tgatcaagga acacacagag    180
aagttcaaca agaagatgca cgagcactcg gagcacttca gcagaagtt cgccgagctg     240
ctcgagcagc agaaggctgc gcagtacccg tccaag                              276
```

<210> SEQ ID NO 30
<211> LENGTH: 1056
<212> TYPE: DNA
<213> ORGANISM: Artificial Sequence
<220> FEATURE:
<223> OTHER INFORMATION: Nucleic acid sequence encoding the SMP
      polypeptide.

<400> SEQUENCE: 30

```
tccgccggtg gccgtgagac cgcgccgacg aacctgattc gtcgccgcaa caaggacgag      60
acaaacgggg atgtcagcgc cgccgccgac cgcttccgcg accgcttcga gaaggcaacc    120
ctcgaggagc gcaaggccgc caccacgacg atggtcaacg agtactacga cctggtgacg    180
gacttctacg agtacggctg gggccagaac ttccatttcg cgccgcgcta cgccggcgag    240
accttcttcg agtccctcgc gcgccacgag tacttcctgg ccgctcgcgg cggcttcatg    300
gagggcgacc acatcgtcga cgtgggctgc ggcgtcggcg gtccggcgcg caacatggtt    360
cgcctcacgc gctgcaacgt catcggcgtc aacaacaacg attaccagat cagccgcgct    420
cgccgtcatg acgcgctcgc cggtatgagc tccaagatcg actacgtcaa gaccgacttc    480
tgcaacatga gcttagccga caacaccttc gacggcgcct acgccatcga ggccacctgc    540
cacgcaaagg acaaggtcaa gtgctatagc gaggtcttcc gtgtcatcaa gcccggcacc    600
tgctttgtcc tgtacgagtg gtgcatgacc gacaagtaca cccccaatga cgagtaccac    660
cgcacaatca agcaccgcat cgagctgggc gacggcctgc cggagatgga gacgtgcaaa    720
caggtgatcg agtacatgaa gcaggccggc ttcgtggtgg aggaggccat agacgtcatc    780
agtcagttcg agtccagccc catcaagagt atcccgtggt accagccgct ggtcggcgac    840
tattcgtccc tgcagggcct gcgctctacc ccgattggcc gcatcctcac gaacgtcatg    900
tgtcgcgtgc tggagttcgt gcgcctagct ccgaagggca cgtacaaggc gacggagatt    960
ttggaggagg ctgcggaaag cctggtggtg ggcggtcagc tcggcatctt cacgccgtcc   1020
ttctacatcc gcgctcgcaa gccgtccaag caggct                             1056
```

<210> SEQ ID NO 31
<211> LENGTH: 629
<212> TYPE: DNA
<213> ORGANISM: Artificial Sequence
<220> FEATURE:
<223> OTHER INFORMATION: Nucleic acid sequence encoding the A2
      polypeptide.

-continued

<400> SEQUENCE: 31

```
gagccgcaca aggcggccgt tgacgtcggc ccgctctccg ttggcccgca gtccgtcggc      60
ccgctctctg ttggcccgca ggctgttggc ccgctctccg ttggcccgca gtccgtcggc     120
ccgctctctg ttggcccgca ggctgttggc ccgctctctg ttggcccgca gtccgttggc     180
ccgctctccg ttggcccgct ctccgttggc ccgcagtctg ttggcccgct ctccgttggc     240
tcgcagtccg tcggcccgct ctctgttggt ccgcagtccg tcggcccgct ctccgttggc     300
ccgcaggctg ttggcccgct ctccgttggc ccgcagtccg tcggcccgct ctctgttggc     360
ccgcaggctg ttggcccgct ctctgttggc ccgcagtccg ttggcccgct ctccgttggc     420
ccgcagtctg ttggcccgct ctccgttggc tcgcagtccg tcggcccgct ctctgttggt     480
ccgcagtccg tcggcccgct ctccgttggc ccgcagtctg tcggcccgct ctccgttggc     540
ccgcagtccg tcggcccgct ctccgttggt ccgcagtccg ttggcccgct ctccgttggc     600
ccgcagtccg ttgacgtttc tccggtgtc                                        629
```

<210> SEQ ID NO 32
<211> LENGTH: 948
<212> TYPE: DNA
<213> ORGANISM: Artificial Sequence
<220> FEATURE:
<223> OTHER INFORMATION: Nucleic acid sequence encoding the CBP polypeptide.

<400> SEQUENCE: 32

```
gatgcggtgg actggcgcga aagggcgcc gtgacgccgg tgaagaatca aggcgcgtgc       60
gggtcgtgct gggcgttctc ggcggtcggc aacatcgagt cgcagtgggc ccgtgccggc     120
cacggcttgg tgagcctgtc ggagcagcag ctggtgagct cgatgacaa agacaatggc     180
tgcaacggcg ggctgatgct gcaggcgttc gagtggctgc tgcgacacat gtacgggatc     240
gtgttcacgg agaagagcta cccctacacg tccggcaacg tgatgtggc cgagtgcttg     300
aacagcagta aactcgttcc cggcgcgcaa atcgacggct acgtgatgat cccgagcaac     360
gaaacggtta tggctgcgtg gcttgcggag aatggcccca tcgcgattgc ggtcgacgcc     420
agctccttca tgtcttacca gagcggcgtg ctgaccagct gcgctggcga tgcactgaac     480
cacggcgtgc tgctcgtcgg gtacaacaag accggtgggg ttccgtactg ggtgatcaag     540
aactcgtggg gtgaggactg gggcgagaag ggctacgtgc gcgtggtcat ggggctgaac     600
gcgtgcctgc tcagtgaata ccccgtgtcc gcgcatgtgc gcggagtct cacccctggc     660
ccgggcacgg agagcgagga gcgcgcccct aaacgggtga cggtggagca gatgatgtgc     720
accgatatgt actgcaggga ggggtgcaag aagagtcttc tcaccgcgaa cgtgtgctac     780
aagaacgggg gaggcggctc ctctatgacg aagtgcggtc cgcagaaggt gctgatgtgc     840
tcgtactcga accctcattg ctttggtcct gggctgtgcc tcgagactcc tgatggcaag     900
tgcgcgccgt acttcttggg ctcgatcatg aacacctgcc agtacacg                  948
```

<210> SEQ ID NO 33
<211> LENGTH: 1003
<212> TYPE: PRT
<213> ORGANISM: Artificial Sequence
<220> FEATURE:
<223> OTHER INFORMATION: Amino acid sequence for the KSAC fusion polypeptide

<400> SEQUENCE: 33

```
Met Ala Thr Thr Tyr Glu Glu Phe Ser Ala Lys Leu Asp Arg Leu Asp
1               5                   10                  15
```

```
Glu Glu Phe Asn Arg Lys Met Gln Glu Gln Asn Ala Lys Phe Phe Ala
             20                  25                  30

Asp Lys Pro Asp Glu Ser Thr Leu Ser Pro Glu Met Lys Glu His Tyr
         35                  40                  45

Glu Lys Phe Glu Arg Met Ile Lys Glu His Thr Glu Lys Phe Asn Lys
     50                  55                  60

Lys Met His Glu His Ser Glu His Phe Lys Gln Lys Phe Ala Glu Leu
 65                  70                  75                  80

Leu Glu Gln Gln Lys Ala Ala Gln Tyr Pro Ser Lys Thr Ser Ser Ala
                 85                  90                  95

Gly Gly Arg Glu Thr Ala Pro Thr Asn Leu Ile Arg Arg Asn Lys
             100                 105                 110

Asp Glu Thr Asn Gly Asp Val Ser Ala Ala Asp Arg Phe Arg Asp
         115                 120                 125

Arg Phe Glu Lys Ala Thr Leu Glu Glu Arg Lys Ala Ala Thr Thr Thr
    130                 135                 140

Met Val Asn Glu Tyr Tyr Asp Leu Val Thr Asp Phe Tyr Glu Tyr Gly
145                 150                 155                 160

Trp Gly Gln Asn Phe His Phe Ala Pro Arg Tyr Ala Gly Glu Thr Phe
                165                 170                 175

Phe Glu Ser Leu Ala Arg His Glu Tyr Phe Leu Ala Ala Arg Gly Gly
            180                 185                 190

Phe Met Glu Gly Asp His Ile Val Asp Val Gly Cys Gly Val Gly Gly
            195                 200                 205

Pro Ala Arg Asn Met Val Arg Leu Thr Arg Cys Asn Val Ile Gly Val
    210                 215                 220

Asn Asn Asn Asp Tyr Gln Ile Ser Arg Ala Arg Arg His Asp Ala Leu
225                 230                 235                 240

Ala Gly Met Ser Ser Lys Ile Asp Tyr Val Lys Thr Asp Phe Cys Asn
                245                 250                 255

Met Ser Leu Ala Asp Asn Thr Phe Asp Gly Ala Tyr Ala Ile Glu Ala
            260                 265                 270

Thr Cys His Ala Lys Asp Lys Val Lys Cys Tyr Ser Glu Val Phe Arg
            275                 280                 285

Val Ile Lys Pro Gly Thr Cys Phe Val Leu Tyr Glu Trp Cys Met Thr
    290                 295                 300

Asp Lys Tyr Asn Pro Asn Asp Glu Tyr His Arg Thr Ile Lys His Arg
305                 310                 315                 320

Ile Glu Leu Gly Asp Gly Leu Pro Glu Met Glu Thr Cys Lys Gln Val
                325                 330                 335

Ile Glu Tyr Met Lys Gln Ala Gly Phe Val Val Glu Glu Ala Ile Asp
            340                 345                 350

Val Ile Ser Gln Phe Glu Ser Ser Pro Ile Lys Ser Ile Pro Trp Tyr
    355                 360                 365

Gln Pro Leu Val Gly Asp Tyr Ser Ser Leu Gly Leu Arg Ser Thr
370                 375                 380

Pro Ile Gly Arg Ile Leu Thr Asn Val Met Cys Arg Val Leu Glu Phe
385                 390                 395                 400

Val Arg Leu Ala Pro Lys Gly Thr Tyr Lys Ala Thr Glu Ile Leu Glu
            405                 410                 415

Glu Ala Ala Glu Ser Leu Val Val Gly Gly Gln Leu Gly Ile Phe Thr
            420                 425                 430

Pro Ser Phe Tyr Ile Arg Ala Arg Lys Pro Ser Lys Gln Ala Gly Ser
```

```
                435                 440                 445
Lys Ile Arg Ser Val Arg Pro Leu Val Leu Leu Val Cys Val Ala
450                 455                 460

Ala Val Leu Ala Leu Ser Ala Ser Ala Glu Pro His Lys Ala Val
465                 470                 475                 480

Asp Val Gly Pro Leu Ser Val Gly Pro Gln Ser Val Gly Pro Leu Ser
                485                 490                 495

Val Gly Pro Gln Ala Val Gly Pro Leu Ser Val Gly Pro Gln Ser Val
            500                 505                 510

Gly Pro Leu Ser Val Gly Pro Gln Ala Val Gly Pro Leu Ser Val Gly
        515                 520                 525

Pro Gln Ser Val Gly Pro Leu Ser Val Gly Pro Leu Ser Val Gly Pro
    530                 535                 540

Gln Ser Val Gly Pro Leu Ser Val Gly Ser Gln Ser Val Gly Pro Leu
545                 550                 555                 560

Ser Val Gly Pro Gln Ser Val Gly Pro Leu Ser Val Gly Pro Gln Ala
                565                 570                 575

Val Gly Pro Leu Ser Val Gly Pro Gln Ser Val Gly Pro Leu Ser Val
            580                 585                 590

Gly Pro Gln Ala Val Gly Pro Leu Ser Val Gly Pro Gln Ser Val Gly
        595                 600                 605

Pro Leu Ser Val Gly Pro Gln Ser Val Gly Pro Leu Ser Val Gly Ser
    610                 615                 620

Gln Ser Val Gly Pro Leu Ser Val Gly Pro Gln Ser Val Gly Pro Leu
625                 630                 635                 640

Ser Val Gly Pro Gln Ser Val Gly Pro Leu Ser Val Gly Pro Gln Ser
                645                 650                 655

Val Gly Pro Leu Ser Val Gly Pro Gln Ser Val Gly Pro Leu Ser Val
            660                 665                 670

Gly Pro Gln Ser Val Asp Val Ser Pro Val Ser Gly Ser Glu Phe Asp
        675                 680                 685

Ala Val Asp Trp Arg Glu Lys Gly Ala Val Thr Pro Val Lys Asn Gln
    690                 695                 700

Gly Ala Cys Gly Ser Cys Trp Ala Phe Ser Ala Val Gly Asn Ile Glu
705                 710                 715                 720

Ser Gln Trp Ala Arg Ala Gly His Gly Leu Val Ser Leu Ser Glu Gln
                725                 730                 735

Gln Leu Val Ser Cys Asp Asp Lys Asp Asn Gly Cys Asn Gly Gly Leu
            740                 745                 750

Met Leu Gln Ala Phe Glu Trp Leu Leu Arg His Met Tyr Gly Ile Val
        755                 760                 765

Phe Thr Glu Lys Ser Tyr Pro Tyr Thr Ser Gly Asn Gly Asp Val Ala
    770                 775                 780

Glu Cys Leu Asn Ser Ser Lys Leu Val Pro Gly Ala Gln Ile Asp Gly
785                 790                 795                 800

Tyr Val Met Ile Pro Ser Asn Glu Thr Val Met Ala Ala Trp Leu Ala
                805                 810                 815

Glu Asn Gly Pro Ile Ala Ile Ala Val Asp Ala Ser Ser Phe Met Ser
            820                 825                 830

Tyr Gln Ser Gly Val Leu Thr Ser Cys Ala Gly Asp Ala Leu Asn His
        835                 840                 845

Gly Val Leu Leu Val Gly Tyr Asn Lys Thr Gly Val Pro Tyr Trp
    850                 855                 860
```

```
Val Ile Lys Asn Ser Trp Gly Glu Asp Trp Gly Glu Lys Gly Tyr Val
865                 870                 875                 880

Arg Val Val Met Gly Leu Asn Ala Cys Leu Leu Ser Glu Tyr Pro Val
            885                 890                 895

Ser Ala His Val Pro Arg Ser Leu Thr Pro Gly Pro Gly Thr Glu Ser
        900                 905                 910

Glu Glu Arg Ala Pro Lys Arg Val Thr Val Glu Gln Met Met Cys Thr
    915                 920                 925

Asp Met Tyr Cys Arg Glu Gly Cys Lys Lys Ser Leu Leu Thr Ala Asn
    930                 935                 940

Val Cys Tyr Lys Asn Gly Gly Gly Ser Ser Met Thr Lys Cys Gly
945                 950                 955                 960

Pro Gln Lys Val Leu Met Cys Ser Tyr Ser Asn Pro His Cys Phe Gly
            965                 970                 975

Pro Gly Leu Cys Leu Glu Thr Pro Asp Gly Lys Cys Ala Pro Tyr Phe
        980                 985                 990

Leu Gly Ser Ile Met Asn Thr Cys Gln Tyr Thr
        995                 1000
```

<210> SEQ ID NO 34
<211> LENGTH: 3021
<212> TYPE: DNA
<213> ORGANISM: Artificial Sequence
<220> FEATURE:
<223> OTHER INFORMATION: Nucleic acid sequence encoding the KSAC fusion
      polypeptide

<400> SEQUENCE: 34

```
catatggcca ccacgtacga ggagttttcg gcgaagctgg accgcctgga tgaggagttc      60
aacaggaaga tgcaggagca gaacgccaag ttctttgcgg acaagccgga tgagtcgacg     120
ctgtcgcccg agatgaagga gcactacgag aagttcgagc gcatgatcaa ggaacacaca     180
gagaagttca acaagaagat gcacgagcac tcggagcact tcaagcagaa gttcgccgag     240
ctgctcgagc agcagaaggc tgcgcagtac ccgtccaaga ctagttccgc cggtggccgt     300
gagaccgcgc cgacgaacct gattcgtcgc cgcaacaagg acgagacaaa cggggatgtc     360
agcgccgccg ccgaccgctt ccgcgaccgc ttcgagaagg caaccctcga ggagcgcaag     420
gccgccacca cgacgatggt caacgagtac tacgacctgg tgacggactt ctacgagtac     480
ggctggggcc agaacttcca tttcgcgccg cgctacgccg cgagaccttt cttcgagtcc     540
ctcgcgcgcc acgagtactt cctggccgct cgcggcggct tcatggaggg cgaccacatc     600
gtcgacgtgg gctgcggcgt cggcggtccg gcgcgcaaca tggttcgcct cacgcgctgc     660
aacgtcatcg gcgtcaacaa caacgattac cagatcagcc gcgctcgccg tcatgacgcg     720
ctcgccggta tgagctccaa gatcgactac gtcaagaccg acttctgcaa catgagctta     780
gccgacaaca ccttcgacgg cgcctacgcc atcgaggcca cctgccacgc aaaggacaag     840
gtcaagtgct atagcgaggt cttccgtgtc atcaagcccg gcacctgctt tgtcctgtac     900
gagtggtgca tgaccgacaa gtacaacccc aatgacgagt accaccgcac aatcaagcac     960
cgcatcgagc tgggcgacgg cctgccggag atggagacgt gcaaacaggt gatcgagtac    1020
atgaagcagg ccggcttcgt ggtggaggag gccatagacg tcatcagtca gttcgagtcc    1080
agccccatca agagtatccc gtggtaccag ccgctggtcg gcgactattc gtccctgcag    1140
ggcctgcgct ctaccccgat tggccgcatc ctcacgaacg tcatgtgtcg cgtgctggag    1200
ttcgtgcgcc tagctccgaa gggcacgtac aaggcgacgg agattttgga ggaggctgcg    1260
```

-continued

```
gaaagcctgg tggtgggcgg tcagctcggc atcttcacgc cgtccttcta catccgcgct   1320
cgcaagccgt ccaagcaggc tggatccaag atccgcagcg tgcgtccgct tgtggtgttg   1380
ctggtgtgcg tcgcggcggt gctcgcactc agcgcctccg ctgagccgca aaggcggcc    1440
gttgacgtcg gcccgctgag cgttggcccg cagagcgtcg gcccgctgag cgttggcccg   1500
caggcggttg gcccgctgag cgttggcccg cagagcgtcg gcccgctgag cgttggcccg   1560
caggcggttg gcccgctgag cgttggcccg cagagcgttg gcccgctgag cgttggcccg   1620
ctgagcgttg gcccgcagag cgttggcccg ctgagcgttg gcagccagag cgtcggcccg   1680
ctgagcgttg gtccgcagag cgtcggcccg ctgagcgttg gcccgcaggc ggttggcccg   1740
ctgagcgttg gcccgcagag cgttggcccg ctgagcgttg gcccgcaggc ggttggcccg   1800
ctgagcgttg gcccgcagag cgttggcccg ctgagcgttg gcccgcagag cgttggcccg   1860
ctgagcgttg gcagccagag cgtcggcccg ctgagcgttg gtccgcagag cgtcggcccg   1920
ctgagcgttg gcccgcagag cgtcggcccg ctgagcgttg gcccgcagag cgtcggcccg   1980
ctgagcgttg gtccgcagag cgttggcccg ctgagcgttg gcccgcagag cgttgacgtt   2040
agcccggtga gcggatccga attcgatgcg gtggactggc gcgagaaggg cgccgtgacg   2100
ccggtgaaga atcaaggcgc gtgcgggtcg tgctgggcgt tctcggcggt cggcaacatc   2160
gagtcgcagt gggcccgtgc cggccacggc ttggtgagcc tgtcggagca gcagctggtg   2220
agctgcgatg acaaagacaa tggctgcaac ggcgggctga tgctgcaggc gttcgagtgg   2280
ctgctgcgac acatgtacgg gatcgtgttc acggagaaga gctacccta cacgtccggc   2340
aacggtgatg tggccgagtg cttgaacagc agtaaactcg ttcccggcgc gcaaatcgac   2400
ggctacgtga tgatcccgag caacgaaacg gttatggctg cgtggcttgc ggagaatggc   2460
cccatcgcga ttgcggtcga cgccagctcc ttcatgtctt accagagcgg cgtgctgacc   2520
agctgcgctg gcgatgcact gaaccacggc gtgctgctcg tcgggtacaa caagaccggt   2580
ggggttccgt actgggtgat caagaactcg tggggtgagg actggggcga aagggctac    2640
gtgcgcgtgg tcatggggct gaacgcgtgc ctgctcagtg ataccccgt gtccgcgcat    2700
gtgccgcgga gtctcacccc tggcccgggc acggagagcg aggagcgcgc ccctaaacgg   2760
gtgacggtgg agcagatgat gtgcaccgat atgtactgca gggagggggtg caagaagagt   2820
cttctcaccg cgaacgtgtg ctacaagaac ggggaggcg gctcctctat gacgaagtgc    2880
ggtccgcaga aggtgctgat gtgctcgtac tcgaaccctc attgctttgg tcctgggctg   2940
tgcctcgaga ctcctgatgg caagtgcgcg ccgtacttct tgggctcgat catgaacacc   3000
tgccagtaca cgtaaaagct t                                             3021
```

<210> SEQ ID NO 35
<211> LENGTH: 660
<212> TYPE: PRT
<213> ORGANISM: Artificial Sequence
<220> FEATURE:
<223> OTHER INFORMATION: Amino acid sequence for a KSA (no Cys) fusion
      polypeptide

<400> SEQUENCE: 35

```
Met Ala Thr Thr Tyr Glu Glu Phe Ser Ala Lys Leu Asp Arg Leu Asp
 1               5                   10                  15

Glu Glu Phe Asn Arg Lys Met Gln Glu Gln Asn Ala Lys Phe Phe Ala
             20                  25                  30

Asp Lys Pro Asp Glu Ser Thr Leu Ser Pro Glu Met Lys Glu His Tyr
         35                  40                  45
```

-continued

```
Glu Lys Phe Glu Arg Met Ile Lys Glu His Thr Gln Lys Phe Asn Lys
 50                  55                  60
Lys Met His Glu His Ser Glu His Phe Lys Gln Lys Phe Ala Glu Leu
 65                  70                  75                  80
Leu Glu Gln Gln Lys Ala Ala Gln Tyr Pro Ser Lys Thr Ser Ser Ala
                 85                  90                  95
Gly Gly Arg Glu Thr Ala Pro Thr Asn Leu Ile Arg Arg Asn Lys
            100                 105                 110
Asp Glu Thr Asn Gly Asp Val Ser Ala Ala Asp Arg Phe Arg Asp
            115                 120                 125
Arg Phe Glu Lys Ala Thr Leu Glu Glu Arg Lys Ala Thr Thr Thr
        130                 135                 140
Met Val Asn Glu Tyr Tyr Asp Leu Val Thr Asp Phe Tyr Glu Tyr Gly
145                 150                 155                 160
Trp Gly Gln Asn Phe His Phe Ala Pro Arg Tyr Ala Gly Glu Thr Phe
                165                 170                 175
Phe Glu Ser Leu Ala Arg His Glu Tyr Phe Leu Ala Ala Arg Gly Gly
            180                 185                 190
Phe Met Glu Gly Asp His Ile Val Asp Val Gly Ser Gly Val Gly Gly
        195                 200                 205
Pro Ala Arg Asn Met Val Arg Leu Thr Arg Ser Asn Val Ile Gly Val
    210                 215                 220
Asn Asn Asn Asp Tyr Gln Ile Ser Arg Ala Arg Arg His Asp Ala Leu
225                 230                 235                 240
Ala Gly Met Ser Ser Lys Ile Asp Tyr Val Lys Thr Asp Phe Ser Asn
                245                 250                 255
Met Ser Leu Ala Asp Asn Thr Phe Asp Gly Ala Tyr Ala Ile Glu Ala
            260                 265                 270
Thr Ser His Ala Lys Asp Lys Val Lys Ser Tyr Ser Glu Val Phe Arg
        275                 280                 285
Val Ile Lys Pro Gly Thr Ser Phe Val Leu Tyr Glu Trp Ser Met Thr
    290                 295                 300
Asp Lys Tyr Asn Pro Asn Asp Glu Tyr His Arg Thr Ile Lys His Arg
305                 310                 315                 320
Ile Glu Leu Gly Asp Gly Leu Pro Glu Met Glu Thr Ser Lys Gln Val
                325                 330                 335
Ile Glu Tyr Met Lys Gln Ala Gly Phe Val Val Glu Glu Ala Ile Asp
            340                 345                 350
Val Ile Ser Gln Phe Glu Ser Ser Pro Ile Lys Ser Ile Pro Trp Tyr
        355                 360                 365
Gln Pro Leu Val Gly Asp Tyr Ser Ser Leu Gly Leu Arg Ser Thr
    370                 375                 380
Pro Ile Gly Arg Ile Leu Thr Asn Val Met Ser Arg Val Leu Glu Phe
385                 390                 395                 400
Val Arg Leu Ala Pro Lys Gly Thr Tyr Lys Ala Thr Glu Ile Leu Glu
                405                 410                 415
Glu Ala Ala Glu Ser Leu Val Val Gly Gly Gln Leu Gly Ile Phe Thr
            420                 425                 430
Pro Ser Phe Tyr Ile Arg Ala Arg Lys Pro Ser Lys Gln Ala Gly Ser
        435                 440                 445
Glu Pro His Lys Ala Ala Val Asp Val Gly Pro Leu Ser Val Gly Pro
    450                 455                 460
Gln Ser Val Gly Pro Leu Ser Val Gly Pro Gln Ala Val Gly Pro Leu
465                 470                 475                 480
```

```
Ser Val Gly Pro Gln Ser Val Gly Pro Leu Ser Val Gly Pro Gln Ala
            485                 490                 495
Val Gly Pro Leu Ser Val Gly Pro Gln Ser Val Gly Pro Leu Ser Val
            500                 505                 510
Gly Pro Leu Ser Val Gly Pro Gln Ser Val Gly Pro Leu Ser Val Gly
            515                 520                 525
Ser Gln Ser Val Gly Pro Leu Ser Val Gly Pro Gln Ser Val Gly Pro
            530                 535                 540
Leu Ser Val Gly Pro Gln Ala Val Gly Pro Leu Ser Val Gly Pro Gln
545                 550                 555                 560
Ser Val Gly Pro Leu Ser Val Gly Pro Gln Ala Val Gly Pro Leu Ser
            565                 570                 575
Val Gly Pro Gln Ser Val Gly Pro Leu Ser Val Gly Pro Gln Ser Val
            580                 585                 590
Gly Pro Leu Ser Val Gly Ser Gln Ser Val Gly Pro Leu Ser Val Gly
            595                 600                 605
Pro Gln Ser Val Gly Pro Leu Ser Val Gly Pro Gln Ser Val Gly Pro
            610                 615                 620
Leu Ser Val Gly Pro Gln Ser Val Gly Pro Leu Ser Val Gly Pro Gln
625                 630                 635                 640
Ser Val Gly Pro Leu Ser Val Gly Pro Gln Ser Val Asp Val Ser Pro
            645                 650                 655
Val Ser Gly Ser
            660

<210> SEQ ID NO 36
<211> LENGTH: 1990
<212> TYPE: DNA
<213> ORGANISM: Artificial Sequence
<220> FEATURE:
<223> OTHER INFORMATION: Nucleotide sequence of KSA (no cys) Cloned in
      NdeI/EcoRI in pET29

<400> SEQUENCE: 36
catatggcca ccacgtacga ggagtttagc gcgaagctgg accgcctgga tgaggagttc      60
aaccgcaaga tgcaggagca gaacgccaag ttctttgcgg acaagccgga tgagagcacg     120
ctgagcccgg agatgaagga gcactacgag aagttcgagc gcatgatcaa ggaacacacc     180
gagaagttca acaagaagat gcacgagcac agcgagcact tcaagcagaa gttcgccgag     240
ctgctggagc agcagaaggc ggcgcagtac ccgagcaaga ctagtagcgc cggtggccgt     300
gagaccgcgc cgacgaacct gattcgtcgc cgcaacaagg acgagaccaa cggcgatgtc     360
agcgccgccg ccgaccgctt ccgcgaccgc ttcgagaagg caaccctgga ggagcgcaag     420
gccgccacca cgacgatggt caacgagtac tacgacctgg tgacggactt ctacgagtac     480
ggctggggcc agaacttcca tttcgcgccg cgctacgccg cgagaccctt cttcgagagc     540
ctggcgcgcc acgagtactt cctggccgcg cgcggcggct tcatggaggg cgaccacatc     600
gtcgacgtgg gcagcggcgt cggcggtccg gcgcgcaaca tggttcgcct gacgcgcagc     660
aacgtcatcg gcgtcaacaa caacgattac cagatcagcc gcgcgcgccg tcatgacgcg     720
ctggccggta tgagcagcaa gatcgactac gtcaagaccg acttcagcaa catgagcctg     780
gccgacaaca ccttcgacgg cgcctacgcc atcgaggcca ccagccacgc aaaggacaag     840
gtcaagagct atagcgaggt cttccgtgtc atcaagccgg gcaccagctt tgtcctgtac     900
gagtggagca tgaccgacaa gtacaacccg aatgacgagt accaccgcac catcaagcac     960
```

```
cgcatcgagc tgggcgacgg cctgccggag atggagacga gcaaacaggt gatcgagtac    1020
atgaagcagg ccggcttcgt ggtggaggag gccattgacg tcatcagcca gttcgagagc    1080
agcccgatca agagcatccc gtggtaccag ccgctggtcg gcgactatag cagcctgcag    1140
ggcctgcgca gcaccccgat tggccgcatc ctgacgaacg tcatgagccg cgtgctggag    1200
ttcgtgcgcc tggcgccgaa gggcacgtac aaggcgacgg agattctgga ggaggcggcg    1260
gaaagcctgg tggtgggcgg tcagctgggc atcttcacgc cgagcttcta catccgcgcg    1320
cgcaagccga gcaagcaggc gggatccgag ccgcacaagg cggccgttga cgtcggcccg    1380
ctgagcgttg gcccgcagag cgtcggcccg ctgagcgttg gcccgcaggc ggttggcccg    1440
ctgagcgttg gcccgcagag cgtcggcccg ctgagcgttg gcccgcaggc ggttggcccg    1500
ctgagcgttg gcccgcagag cgttggcccg ctgagcgttg gcccgctgag cgttggcccg    1560
cagagcgttg gcccgctgag cgttggcagc cagagcgtcg gcccgctgag cgttggtccg    1620
cagagcgtcg gcccgctgag cgttggcccg caggcggttg gcccgctgag cgttggcccg    1680
cagagcgtcg gcccgctgag cgttggcccg caggcggttg gcccgctgag cgttggcccg    1740
cagagcgttg gcccgctgag cgttggcccg cagagcgttg gcccgctgag cgttggcagc    1800
cagagcgtcg gcccgctgag cgttggtccg cagagcgtcg gcccgctgag cgttggcccg    1860
cagagcgtcg gcccgctgag cgttggcccg cagagcgtcg gcccgctgag cgttggtccg    1920
cagagcgttg gcccgctgag cgttggcccg cagagcgttg acgttagccc ggtgagcgga    1980
tcctgaattc                                                           1990

<210> SEQ ID NO 37
<211> LENGTH: 978
<212> TYPE: PRT
<213> ORGANISM: Artificial Sequence
<220> FEATURE:
<223> OTHER INFORMATION: Amino acid sequence of original KSAC (no cys)
      polyprotein fusion

<400> SEQUENCE: 37

Met Ala Thr Thr Tyr Glu Glu Phe Ser Ala Lys Leu Asp Arg Leu Asp
 1               5                  10                  15

Glu Glu Phe Asn Arg Lys Met Gln Glu Gln Asn Ala Lys Phe Phe Ala
                20                  25                  30

Asp Lys Pro Asp Glu Ser Thr Leu Ser Pro Glu Met Lys Glu His Tyr
            35                  40                  45

Glu Lys Phe Glu Arg Met Ile Lys Glu His Thr Glu Lys Phe Asn Lys
        50                  55                  60

Lys Met His Glu His Ser Glu His Phe Lys Gln Lys Phe Ala Glu Leu
65                  70                  75                  80

Leu Glu Gln Gln Lys Ala Ala Gln Tyr Pro Ser Lys Thr Ser Ser Ala
                85                  90                  95

Gly Gly Arg Glu Thr Ala Pro Thr Asn Leu Ile Arg Arg Arg Asn Lys
            100                 105                 110

Asp Glu Thr Asn Gly Asp Val Ser Ala Ala Asp Arg Phe Arg Asp
        115                 120                 125

Arg Phe Glu Lys Ala Thr Leu Glu Glu Arg Lys Ala Ala Thr Thr Thr
    130                 135                 140

Met Val Asn Glu Tyr Tyr Asp Leu Val Thr Asp Phe Tyr Glu Tyr Gly
145                 150                 155                 160

Trp Gly Gln Asn Phe His Phe Ala Pro Arg Tyr Ala Gly Glu Thr Phe
                165                 170                 175
```

-continued

```
Phe Glu Ser Leu Ala Arg His Glu Tyr Phe Leu Ala Ala Arg Gly
                180                 185                 190
Phe Met Glu Gly Asp His Ile Val Asp Val Gly Ser Gly Val Gly Gly
        195                 200                 205
Pro Ala Arg Asn Met Val Arg Leu Thr Arg Ser Asn Val Ile Gly Val
210                 215                 220
Asn Asn Asn Asp Tyr Gln Ile Ser Arg Ala Arg Arg His Asp Ala Leu
225                 230                 235                 240
Ala Gly Met Ser Ser Lys Ile Asp Tyr Val Lys Thr Asp Phe Ser Asn
            245                 250                 255
Met Ser Leu Ala Asp Asn Thr Phe Asp Gly Ala Tyr Ala Ile Glu Ala
        260                 265                 270
Thr Ser His Ala Lys Asp Lys Val Lys Ser Tyr Ser Glu Val Phe Arg
    275                 280                 285
Val Ile Lys Pro Gly Thr Ser Phe Val Leu Tyr Glu Trp Ser Met Thr
290                 295                 300
Asp Lys Tyr Asn Pro Asn Asp Glu Tyr His Arg Thr Ile Lys His Arg
305                 310                 315                 320
Ile Glu Leu Gly Asp Gly Leu Pro Glu Met Glu Thr Ser Lys Gln Val
            325                 330                 335
Ile Glu Tyr Met Lys Gln Ala Gly Phe Val Val Glu Glu Ala Ile Asp
        340                 345                 350
Val Ile Ser Gln Phe Glu Ser Ser Pro Ile Lys Ser Ile Pro Trp Tyr
    355                 360                 365
Gln Pro Leu Val Gly Asp Tyr Ser Ser Leu Gln Gly Leu Arg Ser Thr
370                 375                 380
Pro Ile Gly Arg Ile Leu Thr Asn Val Met Ser Arg Val Leu Glu Phe
385                 390                 395                 400
Val Arg Leu Ala Pro Lys Gly Thr Tyr Lys Ala Thr Glu Ile Leu Glu
            405                 410                 415
Glu Ala Ala Glu Ser Leu Val Val Gly Gly Gln Leu Gly Ile Phe Thr
        420                 425                 430
Pro Ser Phe Tyr Ile Arg Ala Arg Lys Pro Ser Lys Gln Ala Gly Ser
    435                 440                 445
Glu Pro His Lys Ala Ala Val Asp Val Gly Pro Leu Ser Val Gly Pro
450                 455                 460
Gln Ser Val Gly Pro Leu Ser Val Gly Pro Gln Ala Val Gly Pro Leu
465                 470                 475                 480
Ser Val Gly Pro Gln Ser Val Gly Pro Leu Ser Val Gly Pro Gln Ala
            485                 490                 495
Val Gly Pro Leu Ser Val Gly Pro Gln Ser Val Gly Pro Leu Ser Val
        500                 505                 510
Gly Pro Leu Ser Val Gly Pro Gln Ser Val Gly Pro Leu Ser Val Gly
    515                 520                 525
Ser Gln Ser Val Gly Pro Leu Ser Val Gly Pro Gln Ser Val Gly Pro
530                 535                 540
Leu Ser Val Gly Pro Gln Ala Val Gly Pro Leu Ser Val Gly Pro Gln
545                 550                 555                 560
Ser Val Gly Pro Leu Ser Val Gly Pro Gln Ala Val Gly Pro Leu Ser
            565                 570                 575
Val Gly Pro Gln Ser Val Gly Pro Leu Ser Val Gly Pro Gln Ser Val
        580                 585                 590
Gly Pro Leu Ser Val Gly Ser Gln Ser Val Gly Pro Leu Ser Val Gly
    595                 600                 605
```

```
Pro Gln Ser Val Gly Pro Leu Ser Val Gly Pro Gln Ser Val Gly Pro
        610                 615                 620

Leu Ser Val Gly Pro Gln Ser Val Gly Pro Leu Ser Val Gly Pro Gln
625                 630                 635                 640

Ser Val Gly Pro Leu Ser Val Gly Pro Gln Ser Val Asp Val Ser Pro
            645                 650                 655

Val Ser Gly Ser Glu Phe Asp Ala Val Asp Trp Arg Glu Lys Gly Ala
        660                 665                 670

Val Thr Pro Val Lys Asn Gln Gly Ala Ser Gly Ser Trp Ala Phe
        675                 680                 685

Ser Ala Val Gly Asn Ile Glu Ser Gln Trp Ala Arg Ala Gly His Gly
        690                 695                 700

Leu Val Ser Leu Ser Glu Gln Gln Leu Val Ser Ser Asp Asp Lys Asp
705                 710                 715                 720

Asn Gly Ser Asn Gly Gly Leu Met Leu Gln Ala Phe Glu Trp Leu Leu
                725                 730                 735

Arg His Met Tyr Gly Ile Val Phe Thr Glu Lys Ser Tyr Pro Tyr Thr
            740                 745                 750

Ser Gly Asn Gly Asp Val Ala Glu Ser Leu Asn Ser Lys Leu Val
        755                 760                 765

Pro Gly Ala Gln Ile Asp Gly Tyr Val Met Ile Pro Ser Asn Glu Thr
770                 775                 780

Val Met Ala Ala Trp Leu Ala Glu Asn Gly Pro Ile Ala Ile Ala Val
785                 790                 795                 800

Asp Ala Ser Ser Phe Met Ser Tyr Gln Ser Gly Val Leu Thr Ser Ser
                805                 810                 815

Ala Gly Asp Ala Leu Asn His Gly Val Leu Val Gly Tyr Asn Lys
            820                 825                 830

Thr Gly Gly Val Pro Tyr Trp Val Ile Lys Asn Ser Trp Gly Glu Asp
            835                 840                 845

Trp Gly Glu Lys Gly Tyr Val Arg Val Val Met Gly Leu Asn Ala Ser
850                 855                 860

Leu Leu Ser Glu Tyr Pro Val Ser Ala His Val Pro Arg Ser Leu Thr
865                 870                 875                 880

Pro Gly Pro Gly Thr Glu Ser Glu Glu Arg Ala Pro Lys Arg Val Thr
                885                 890                 895

Val Glu Gln Met Met Ser Thr Asp Met Tyr Ser Arg Glu Gly Ser Lys
                900                 905                 910

Lys Ser Leu Leu Thr Ala Asn Val Ser Tyr Lys Asn Gly Gly Gly
        915                 920                 925

Ser Ser Met Thr Lys Ser Gly Pro Gln Lys Val Leu Met Ser Ser Tyr
        930                 935                 940

Ser Asn Pro His Ser Phe Gly Pro Gly Leu Ser Leu Glu Thr Pro Asp
945                 950                 955                 960

Gly Lys Ser Ala Pro Tyr Phe Leu Gly Ser Ile Met Asn Thr Ser Gln
                965                 970                 975

Tyr Thr

<210> SEQ ID NO 38
<211> LENGTH: 2946
<212> TYPE: DNA
<213> ORGANISM: Artificial Sequence
<220> FEATURE:
<223> OTHER INFORMATION: Nucleotide sequence of original KSAC (no cys)
      Cloned in NdeI/HindIII in pET29
```

```
<400> SEQUENCE: 38
catatggcca ccacgtacga ggagtttagc gcgaagctgg accgcctgga tgaggagttc      60
aaccgcaaga tgcaggagca gaacgccaag ttctttgcgg acaagccgga tgagagcacg     120
ctgagcccgg agatgaagga gcactacgag aagttcgagc gcatgatcaa ggaacacacc     180
gagaagttca acaagaagat gcacgagcac agcgagcact tcaagcagaa gttcgccgag     240
ctgctggagc agcagaaggc ggcgcagtac ccgagcaaga ctagtagcgc cggtggccgt     300
gagaccgcgc cgacgaacct gattcgtcgc cgcaacaagg acgagaccaa cggcgatgtc     360
agcgccgccg ccgaccgctt ccgcgaccgc ttcgagaagg caaccctgga ggagcgcaag     420
gccgccacca cgacgatggt caacgagtac tacgacctgg tgacggactt ctacgagtac     480
ggctggggcc agaacttcca tttcgcgccg cgctacgccg gcgagacctt cttcgagagc     540
ctggcgcgcc acgagtactt cctggccgcg cgcggcggct tcatggaggg cgaccacatc     600
gtcgacgtgg gcagcggcgt cggcggtccg gcgcgcaaca tggttcgcct gacgcgcagc     660
aacgtcatcg gcgtcaacaa caacgattac cagatcagcc gcgcgcgccg tcatgacgcg     720
ctggccggta tgagcagcaa gatcgactac gtcaagaccg acttcagcaa catgagcctg     780
gccgacaaca ccttcgacgg cgcctacgcc atcgaggcca ccagccacgc aaaggacaag     840
gtcaagagct atagcgaggt cttccgtgtc atcaagccgg gcaccagctt tgtcctgtac     900
gagtggagca tgaccgacaa gtacaacccg aatgacgagt accaccgcac catcaagcac     960
cgcatcgagc tgggcgacgg cctgccggag atggagacga gcaaacaggt gatcgagtac    1020
atgaagcagg ccggcttcgt ggtggaggag gccattgacg tcatcagcca gttcgagagc    1080
agcccgatca agagcatccc cgtggtaccag ccgctggtcg gcgactatag cagcctgcag    1140
ggcctgcgca gcaccccgat tggccgcatc ctgacgaacg tcatgagccg cgtgctggag    1200
ttcgtgcgcc tggcgccgaa gggcacgtac aaggcgacgg agattctgga ggaggcggcg    1260
gaaagcctgg tggtgggcgg tcagctgggc atcttcacgc cgagcttcta catccgcgcg    1320
cgcaagccga gcaagcaggc gggatccgag ccgcacaagg cggccgttga cgtcggcccg    1380
ctgagcgttg gcccgcagag cgtcggcccg ctgagcgttg gccgcaggc ggttggcccg     1440 ctgagcgttg gcccgcagag cgtcggcccg ctgagcgttg gccgcaggc ggttggcccg     1500 ctgagcgttg gcccgcagag cgttggcccg ctgagcgttg gccgctgag cgttggcccg     1560 cagagcgttg gccgctgag cgttggcagc cagagcgtcg gccgctgag cgttggtccg     1620 cagagcgtcg gccgctgag cgttggcccg caggcgttg gccgctgag cgttggcccg      1680 cagagcgtcg gccgctgag cgttggcccg caggcgttg gccgctgag cgttggcccg      1740 cagagcgttg gccgctgag cgttggcccg cagagcgttg gccgctgag cgttggcagc     1800 cagagcgtcg gccgctgag cgttggtccg cagagcgtcg gccgctgag cgttggcccg     1860 cagagcgtcg gccgctgag cgttggcccg cagagcgtcg gccgctgag cgttggtccg     1920 cagagcgttg gccgctgag cgttggcccg cagagcgttg acgttagccc ggtgagcgga    1980
tccgaattcg atgcggtgga ctggcgcgag aagggcgccg tgacgccggt gaagaatcaa    2040
ggcgcgagcg gcagcagctg ggcgttcagc gcggtcggca acatcgagag ccagtgggcc    2100
cgtgccggcc acggcctggt gagcctgagc gagcagcagc tggtgagcag cgatgacaaa    2160
gacaatggca gcaacggcgg cctgatgctg caggcgttcg agtggctgct gcgccacatg    2220
tacggcatcg tgttcacgga gaagagctac ccgtacacga gcggcaacgg tgatgtggcc    2280
gagagcctga acagcagcaa actggttccg ggcgcgcaaa tcgacggcta cgtgatgatc    2340
```

```
ccgagcaacg aaacggttat ggcggcgtgg ctggcggaga atggcccgat cgcgattgcg    2400
gtcgacgcca gcagcttcat gagctaccag agcggcgtgc tgaccagcag cgcgggcgat    2460
gcactgaacc acggcgtgct gctggtcggc tacaacaaga ccggtggcgt tccgtactgg    2520
gtgatcaaga acagctgggg tgaggactgg ggcgagaagg gctacgtgcg cgtggtcatg    2580
ggcctgaacg cgagcctgct gagcgaatac ccggtgagcg cgcatgtgcc gcgcagcctg    2640
accccgggcc cgggcacgga gagcgaggag cgcgccccga aacgcgtgac ggtggagcag    2700
atgatgagca ccgatatgta cagccgcgag ggcagcaaga agagcctgct gaccgcgaac    2760
gtgagctaca agaacggcgg cggcggcagc agcatgacga agagcggtcc gcagaaggtg    2820
ctgatgagca gctacagcaa cccgcatagc tttggtccgg gcctgagcct ggagaccccg    2880
gatggcaaga gcgcgccgta cttcctgggc agcatcatga acaccagcca gtacacgtaa    2940
aagctt                                                              2946
```